(12) United States Patent
Speeg et al.

(10) Patent No.: US 9,877,706 B2
(45) Date of Patent: Jan. 30, 2018

(54) BIOPSY DEVICE

(71) Applicant: Devicor Medical Products, Inc., Cincinnati, OH (US)

(72) Inventors: Trevor W. V. Speeg, Williamsburg, OH (US); Edward A. Rhad, Fairfield, OH (US); Emmanuel V. Tanghal, Mason, OH (US); Morgan R. Hunter, Cincinnati, OH (US); Jessica P. Leimbach, Cincinnati, OH (US); Andrew P. Nock, Centerville, OH (US); Kevin M. Fiebig, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 160 days.

(21) Appl. No.: 14/208,354

(22) Filed: Mar. 13, 2014

(65) Prior Publication Data

US 2014/0275999 A1  Sep. 18, 2014

Related U.S. Application Data

(60) Provisional application No. 61/790,020, filed on Mar. 15, 2013.

(51) Int. Cl.
*A61B 10/00* (2006.01)
*A61B 10/02* (2006.01)
(Continued)

(52) U.S. Cl.
CPC .......... *A61B 10/0096* (2013.01); *A61B 10/02* (2013.01); *A61B 10/0266* (2013.01);
(Continued)

(58) Field of Classification Search
CPC ......................................... A61B 2017/320064
See application file for complete search history.

(56) References Cited

U.S. PATENT DOCUMENTS

| 5,526,822 A | 6/1996 | Burbank et al. |
| 5,928,164 A | 7/1999 | Burbank et al. |

(Continued)

FOREIGN PATENT DOCUMENTS

| EP | 1642534 A2 | 4/2006 |
| EP | 1932482 A1 | 6/2008 |

(Continued)

OTHER PUBLICATIONS

U.S. Appl. No. 61/566,793, filed Dec. 5, 2011.
(Continued)

*Primary Examiner* — Katherine Fernandez
*Assistant Examiner* — Michael Kellogg
(74) *Attorney, Agent, or Firm* — Frost Brown Todd LLC

(57) ABSTRACT

A biopsy device includes a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and a arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

17 Claims, 59 Drawing Sheets

(51) Int. Cl.
    *A61B 6/12*      (2006.01)
    *A61B 17/32*      (2006.01)
    *B01L 3/00*      (2006.01)

(52) U.S. Cl.
    CPC ............. *A61B 6/12* (2013.01); *A61B 10/0283* (2013.01); *A61B 2010/0225* (2013.01); *A61B 2017/320064* (2013.01); *B01L 3/505* (2013.01); *B01L 3/5055* (2013.01)

(56) References Cited

U.S. PATENT DOCUMENTS

| | | | |
|---|---|---|---|
| 6,017,316 | A | 1/2000 | Ritchart et al. |
| 6,086,544 | A | 4/2000 | Hibner et al. |
| 6,162,187 | A | 12/2000 | Buzzard et al. |
| 6,228,055 | B1 | 5/2001 | Foerster et al. |
| 6,371,904 | B1 | 4/2002 | Sirimanne et al. |
| 6,432,065 | B1 | 8/2002 | Burdorff et al. |
| 6,485,436 | B1 | 11/2002 | Truckai et al. |
| 6,626,849 | B2 | 9/2003 | Huitema et al. |
| 6,752,768 | B2 | 6/2004 | Burdorff et al. |
| 6,993,375 | B2 | 1/2006 | Burbank et al. |
| 6,996,433 | B2 | 2/2006 | Burbank et al. |
| 7,044,957 | B2 | 5/2006 | Foerster et al. |
| 7,047,063 | B2 | 5/2006 | Burbank et al. |
| 7,229,417 | B2 | 6/2007 | Foerster et al. |
| 7,442,171 | B2 | 10/2008 | Stephens et al. |
| 7,465,279 | B2 | 12/2008 | Beckman et al. |
| 7,648,466 | B2 | 1/2010 | Stephens et al. |
| 7,837,632 | B2 | 11/2010 | Stephens et al. |
| 7,854,706 | B2 | 12/2010 | Hibner |
| 7,914,464 | B2 | 3/2011 | Burdorff et al. |
| 7,918,803 | B2 | 4/2011 | Ritchart et al. |
| 7,918,804 | B2 | 4/2011 | Monson et al. |
| 7,938,786 | B2 | 5/2011 | Ritchie et al. |
| 8,002,785 | B2 | 8/2011 | Weiss et al. |
| 8,083,687 | B2 | 12/2011 | Parihar |
| 8,118,755 | B2 | 2/2012 | Hibner et al. |
| 8,206,316 | B2 | 6/2012 | Hibner et al. |
| 8,241,226 | B2 | 8/2012 | Hibner et al. |
| 8,371,443 | B2 | 2/2013 | Nock et al. |
| 8,454,531 | B2 | 6/2013 | Speeg et al. |
| 8,532,747 | B2 | 9/2013 | Nock et al. |
| 8,532,748 | B2 | 9/2013 | Leimbach et al. |
| 8,622,924 | B2 | 1/2014 | Speeg et al. |
| 8,622,927 | B2 | 1/2014 | Parihar et al. |
| 8,961,431 | B2 | 2/2015 | Roe et al. |
| 2003/0052074 | A1* | 3/2003 | Chang ................. B01L 3/50825 215/247 |
| 2004/0164045 | A1* | 8/2004 | Kelley ................. B65D 1/0223 215/373 |
| 2006/0074345 | A1 | 4/2006 | Hibner |
| 2008/0146962 | A1 | 6/2008 | Ritchie et al. |
| 2008/0214955 | A1 | 9/2008 | Speeg et al. |
| 2009/0131821 | A1 | 5/2009 | Speeg et al. |
| 2009/0209854 | A1 | 8/2009 | Parihar et al. |
| 2010/0152610 | A1 | 6/2010 | Parihar et al. |
| 2010/0155282 | A1* | 6/2010 | Govil ................... A61F 2/0095 206/438 |
| 2010/0160819 | A1 | 6/2010 | Parihar et al. |
| 2010/0160824 | A1 | 6/2010 | Parihar et al. |
| 2011/0071391 | A1 | 3/2011 | Speeg |
| 2011/0071423 | A1 | 3/2011 | Speeg et al. |
| 2011/0295153 | A1 | 12/2011 | Lai et al. |
| 2012/0109007 | A1 | 5/2012 | Rhad et al. |
| 2012/0265095 | A1 | 10/2012 | Fiebig |
| 2012/0283563 | A1 | 11/2012 | Moore et al. |
| 2012/0310110 | A1 | 12/2012 | Rhad et al. |
| 2013/0041256 | A1 | 2/2013 | Fiebig et al. |
| 2013/0053724 | A1* | 2/2013 | Fiebig ................. A61B 10/0275 600/567 |
| 2013/0218047 | A1 | 8/2013 | Fiebig et al. |
| 2013/0324882 | A1 | 12/2013 | Mescher |

FOREIGN PATENT DOCUMENTS

| | | |
|---|---|---|
| JP | H09-510638 A | 10/1997 |
| JP | 2012-510851 A | 5/2012 |
| JP | 2013-505747 | 2/2013 |
| WO | WO 1998/033436 | 8/1998 |
| WO | WO 2000/030531 | 6/2000 |
| WO | WO 2012/074885 | 6/2012 |
| WO | WO 2012/123391 A1 * | 9/2012 ............. B29C 51/00 |

OTHER PUBLICATIONS

U.S. Appl. No. 61/682,418, filed Aug. 13, 2012.
U.S. Appl. No. 61/727,889, filed Nov. 19, 2012.
U.S. Appl. No. 61/771,212, filed Mar. 1, 2013.
U.S. Appl. No. 61/790,020, filed Mar. 15, 2013.
International Preliminary Report on Patentability for Application No. PCT/US2014/026091, 7 pages.
Extended European Search Report dated Oct. 18, 2016 for Application No. EP 14768633.1, 8 pgs.
Japanese Office Action dated Oct. 3, 2017 for Application No. 2016-502048, 4 pgs.

* cited by examiner

BIOPSY DEVICE

PRIORITY

This application claims priority to U.S. Provisional Patent App. No. 61/790,020, entitled "Tissue Sample Holder with Flexing Member," filed Mar. 15, 2013, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009; U.S. Pat. Pub. No. 2009/0216152, entitled "Needle Tip for Biopsy Device," published Aug. 27, 2009; U.S. Pat. Pub. No. 2010/0113973, entitled "Biopsy Device with Rotatable Tissue Sample Holder," published May 6, 2010; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010; U.S. Pat. Pub. No. 2010/0317997, entitled "Tetherless Biopsy Device with Reusable Portion," published Dec. 16, 2010; U.S. Pat. Pub. No. 2012/0109007, entitled "Handheld Biopsy Device with Needle Firing," published May 3, 2012; U.S. Pat. Pub. No. 2012/0265095, entitled "Biopsy Device with Motorized Needle Firing," published Oct. 18, 2012; U.S. Pat. Pub. No. 2012/0283563, entitled "Biopsy Device with Manifold Alignment Feature and Tissue Sensor," published Nov. 8, 2012; U.S. Pat. Pub. No. 2012/0310110, entitled "Needle Assembly and Blade Assembly for Biopsy Device," published Dec. 6, 2012; U.S. Pat. Pub. No. 2013/0041256, entitled "Access Chamber and Markers for Biopsy Device," published Feb. 14, 2013; U.S. Pat. Pub. No. 2013/0053724, entitled "Biopsy Device Tissue Sample Holder with Bulk Chamber and Pathology Chamber," published Feb. 28, 2013; U.S. Provisional Patent App. No. 61/566,793, entitled "Biopsy Device With Slide-In Probe," filed Dec. 5, 2011; U.S. Non-Provisional patent application Ser. No. 13/483,235, entitled "Control for Biopsy Device," filed May 30, 2012; U.S. Non-Provisional patent application Ser. No. 13/765,931, entitled "Biopsy Device Valve Assembly," filed Feb. 13, 2013; U.S. Provisional Patent App. No. 61/682,418, entitled "Biopsy System with Graphical User Interface," filed Aug. 13, 2012; U.S. Provisional Patent App. No. 61/727,889, entitled "Biopsy System with Graphical User Interface," filed Nov. 19, 2012; and U.S. Provisional Patent App. No. 61/771,212, entitled "Biopsy System with Graphical User Interface," filed Mar. 1, 2013. The disclosure of each of the above-cited U.S. patent application Publications, U.S. Non-Provisional patent applications, and U.S. Provisional patent applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. patents and U.S. patent application Publications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
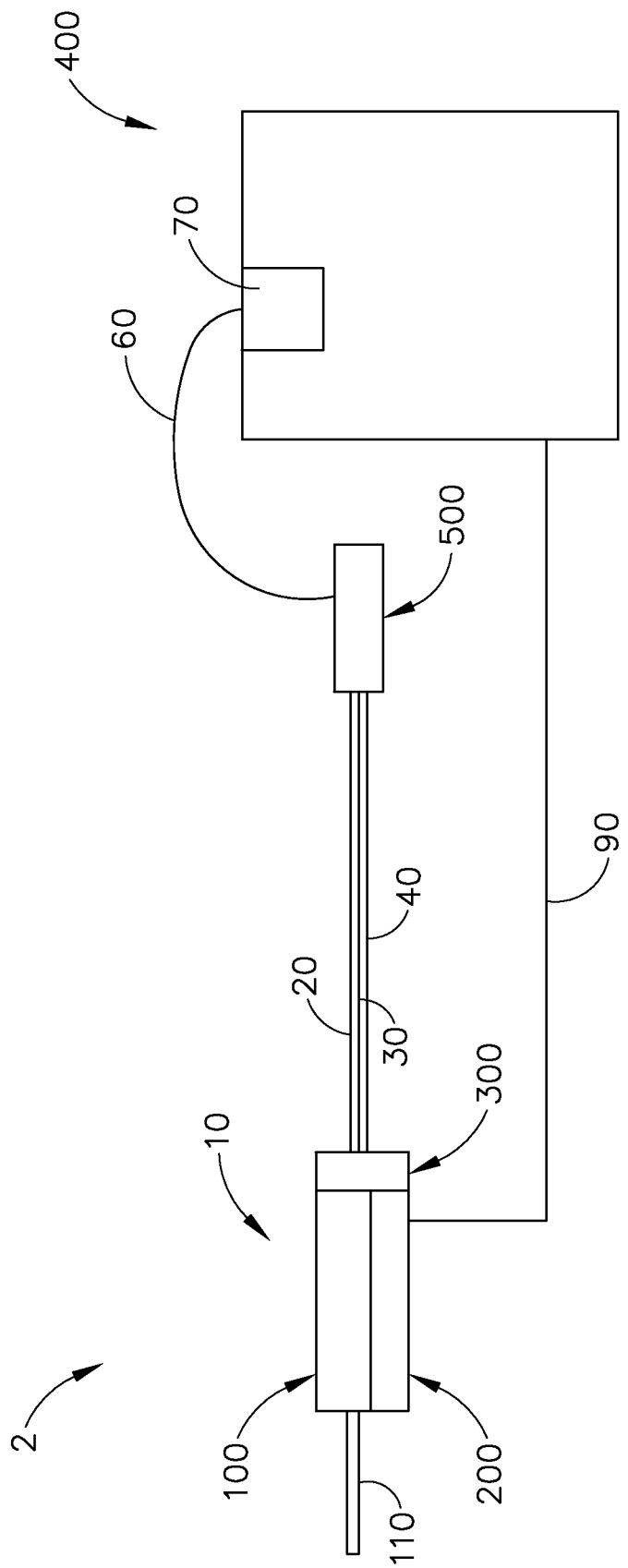
FIG. 1 depicts a schematic view of an exemplary biopsy system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

Figure 2:
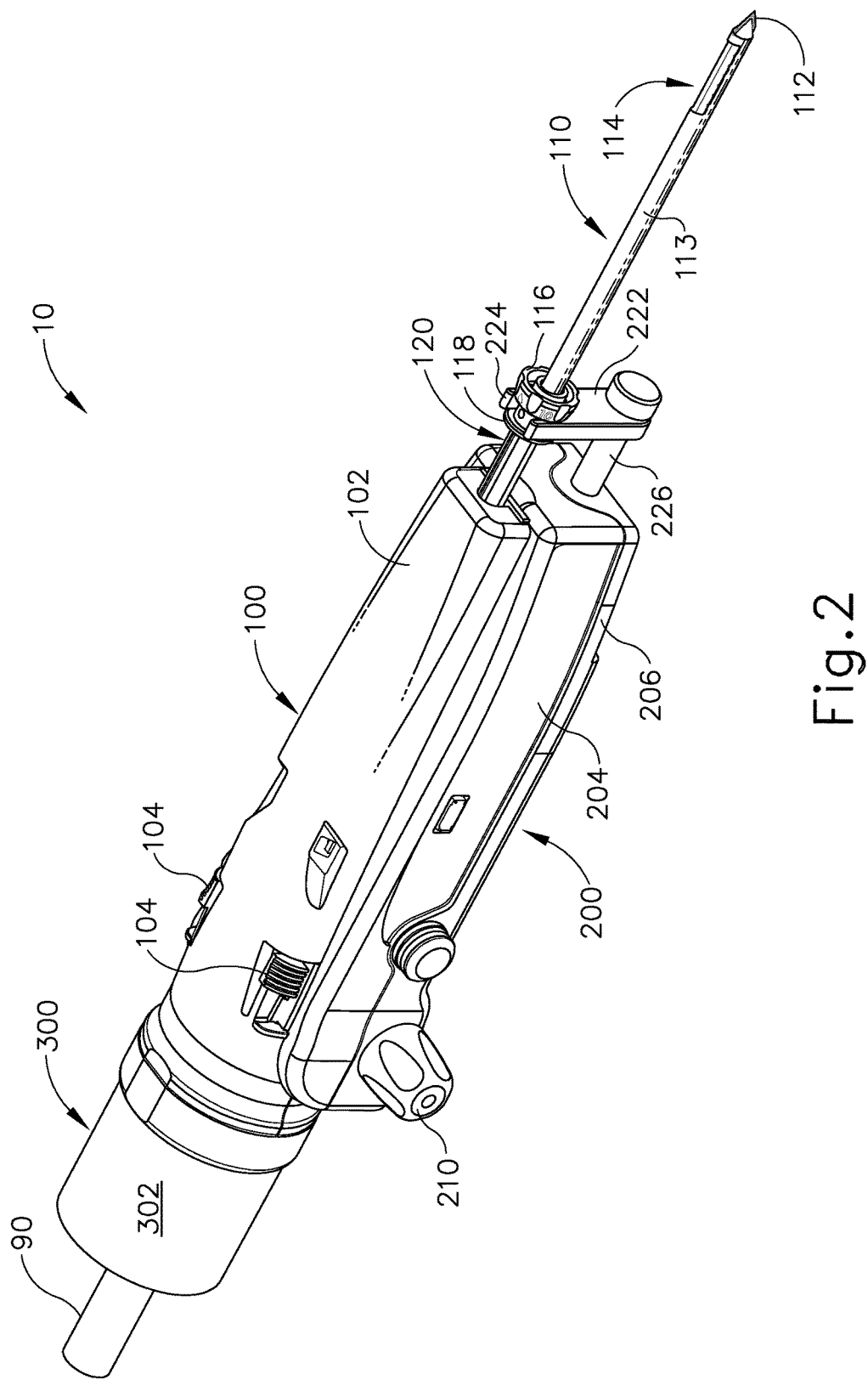
FIG. 2 depicts a perspective view of an exemplary biopsy device of the biopsy system of FIG. 1, including an exemplary probe coupled with an exemplary holster.
Figure 3:
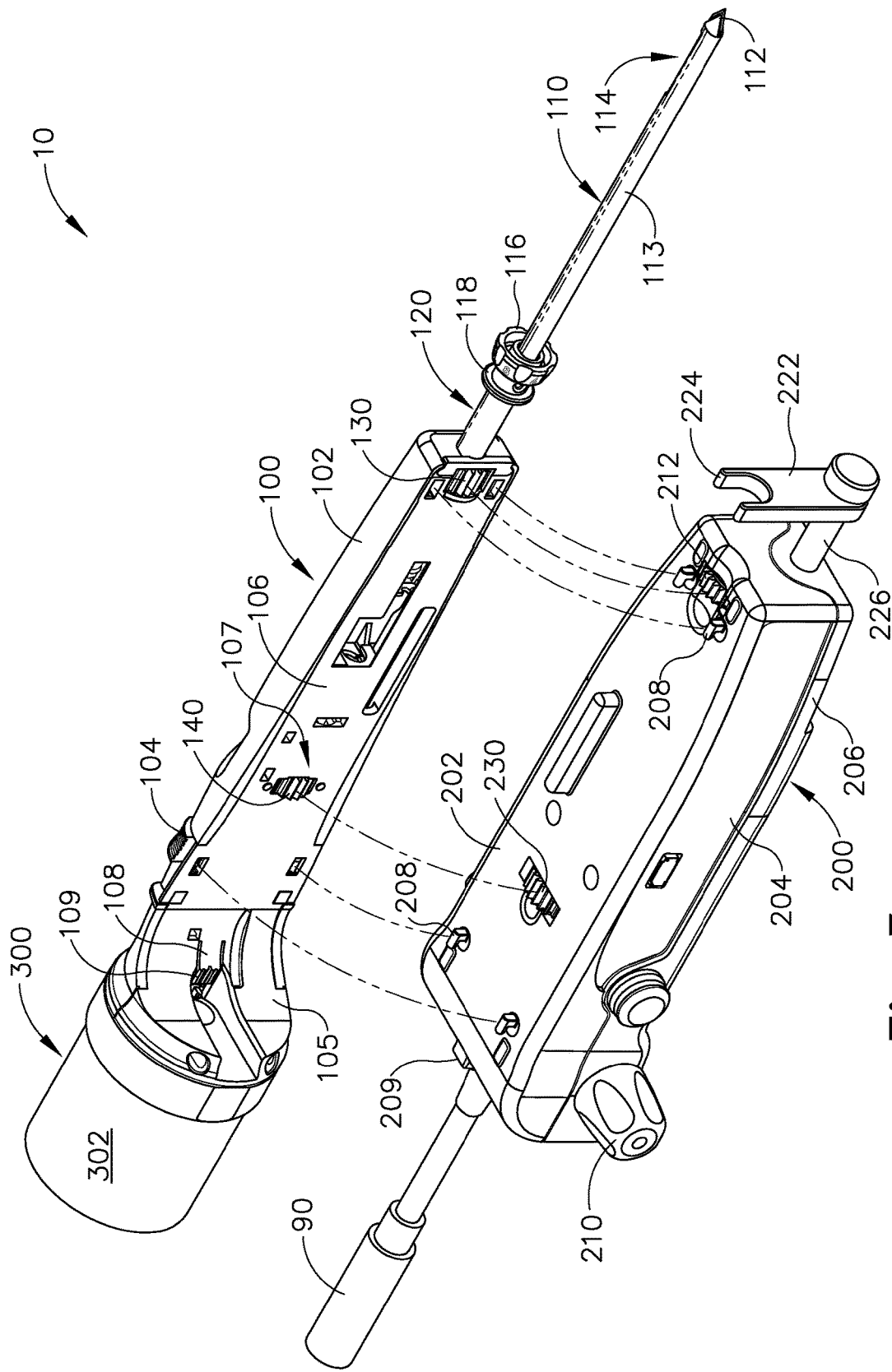
FIG. 3 depicts a perspective view of the biopsy device of FIG. 2, with the probe decoupled from the holster.

FIG. 1 depicts an exemplary biopsy system (2) comprising a biopsy device (10) and a vacuum control module (400). Biopsy device (10) of this example comprises a probe (100) and a holster (200), as shown in FIGS. 2-3. A needle (110) extends distally from probe (100), and is inserted into a patient's tissue to obtain tissue samples. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Holster

As shown in FIG. 3, holster (200) of the present example includes a top housing cover (202), side panels (204), and a housing base (206), which are fixedly secured together. Gears (212, 230) are exposed through top housing cover (202), and mesh with gears (130, 140) of probe (100) when probe (100) and holster (200) are coupled together. In particular, gears (230, 140) drive the actuation assembly of a cutter (150) within needle (110); while gears (212, 130) are employed to rotate needle (110). Gear (240) is located at the proximal end of holster (200) and meshes with gear (182) of probe (100) to rotate a manifold (310) of tissue sample holder (300).

As noted above, rotation of gear (212) provides rotation of needle (110) relative to probe (100). In the present example, gear (212) is rotated by rotating knob (210). In particular, knob (210) is coupled with gear (212) by a series of gears (not shown) and shafts (not shown), such that rotation of knob (210) rotates gear (212). A second knob (210) extends from the other side of holster (200). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating thumbwheel (116). Various other suitable ways in which rotation of needle (110) may be provided will be apparent to those of ordinary skill in the art in view of the teachings herein. It should also be understood that some versions may provide no rotation of needle (110).

Holster (200) also includes a firing rod (226) and fork (222), which couple with needle (110) and fire needle (110) distally. By way of example only, such firing may be useful in instances where biopsy device (10) is mounted to a stereotactic table fixture or other fixture, with tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

In the present example, the needle firing mechanism is coupled with needle (110) via a firing rod (226) and a firing fork (222). Firing rod (226) and firing fork (222) are unitarily secured together. Firing fork (222) includes a pair of prongs (224) that receive hub member (120) of needle (110) therebetween. Prongs (224) are positioned between annular flange (118) and thumbwheel (116), such that needle (110) will translate unitarily with firing rod (226) and fork (222). Prongs (224) nevertheless removably receive hub member (120), such that fork (222) may be readily secured to hub member (120) when probe (100) is coupled with holster (200); and such that hub member (120) may be readily removed from fork (222) when probe (100) is decoupled from holster (200). Prongs (224) are also configured to permit hub member (120) to rotate between prongs (224). Other suitable components, configurations, and relationships will be apparent to those of ordinary skill in the art in view of the teachings herein. The internal components of the needle firing mechanism of the present example are configured and arranged as described in U.S. Non-Provisional patent application Ser. No. 13/086,567, entitled "Biopsy Device with Motorized Needle Firing," filed Apr. 14, 2011, the disclosure of which is incorporated by reference herein.

Holster (200) includes motors (not shown) to drive gears (230, 240) to thereby rotate and translate cutter (150) and rotate manifold (310) of tissue sample holder (300). Holster (200) also includes a motor (not shown) that is operable to drive firing rod (226), to thereby arm and fire needle (110). All motors referred to herein are contained within holster (200) in the present example and receive power from vacuum control module (400) via cable (90). In addition, data may be communicated between vacuum control module (400) and holster (200) via cable (90). In some other versions, one or more motors are powered by one or more batteries located within holster (200) and/or probe (100). It should therefore be understood that, as with other components described herein, cable (90) is merely optional. As yet another merely illustrative variation, motors may be powered pneumatically, such that cable (90) may be substituted with a conduit communicating a pressurized fluid medium to holster (200). As still other merely illustrative variation, cable (90) may include one or more rotary drive cables that are driven by motors that are located external to holster (200). It should also be understood that two or three of the motors may be combined as a single motor. Other suitable ways in which various the motors may be driven will be apparent to those of ordinary skill in the art in view of the teachings herein.

III. Exemplary Probe

Probe (100) of the present example includes a needle (110) extending distally from probe (100) that is inserted into a patient's tissue to obtain tissue samples. These tissue samples are deposited in a tissue sample holder (300) at the proximal end of probe (100). As shown in FIG. 1, vacuum control module (400) is coupled with probe (100) via a valve assembly (500) and tubes (20, 30, 40, 60), which is operable to selectively provide vacuum, saline, atmospheric air, and venting to probe (100). The internal components of the valve assembly of the present example are configured and arranged as described in U.S. Non-Provisional patent application Ser. No. 13/765,931, entitled "Biopsy Device Valve Assembly," filed Feb. 13, 2013, the disclosure of which is incorporated by reference herein.

As shown in FIGS. 1-6, probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together.

A. Exemplary Needle Assembly

Needle (110) of the present example comprises a cannula (113) having a tissue piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Non-Provisional patent application Ser. No. 13/150,950, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Provisional Pat. App. No. 61/566,793, entitled "Biopsy Device with Slide-In Probe," filed Dec. 5, 2011, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
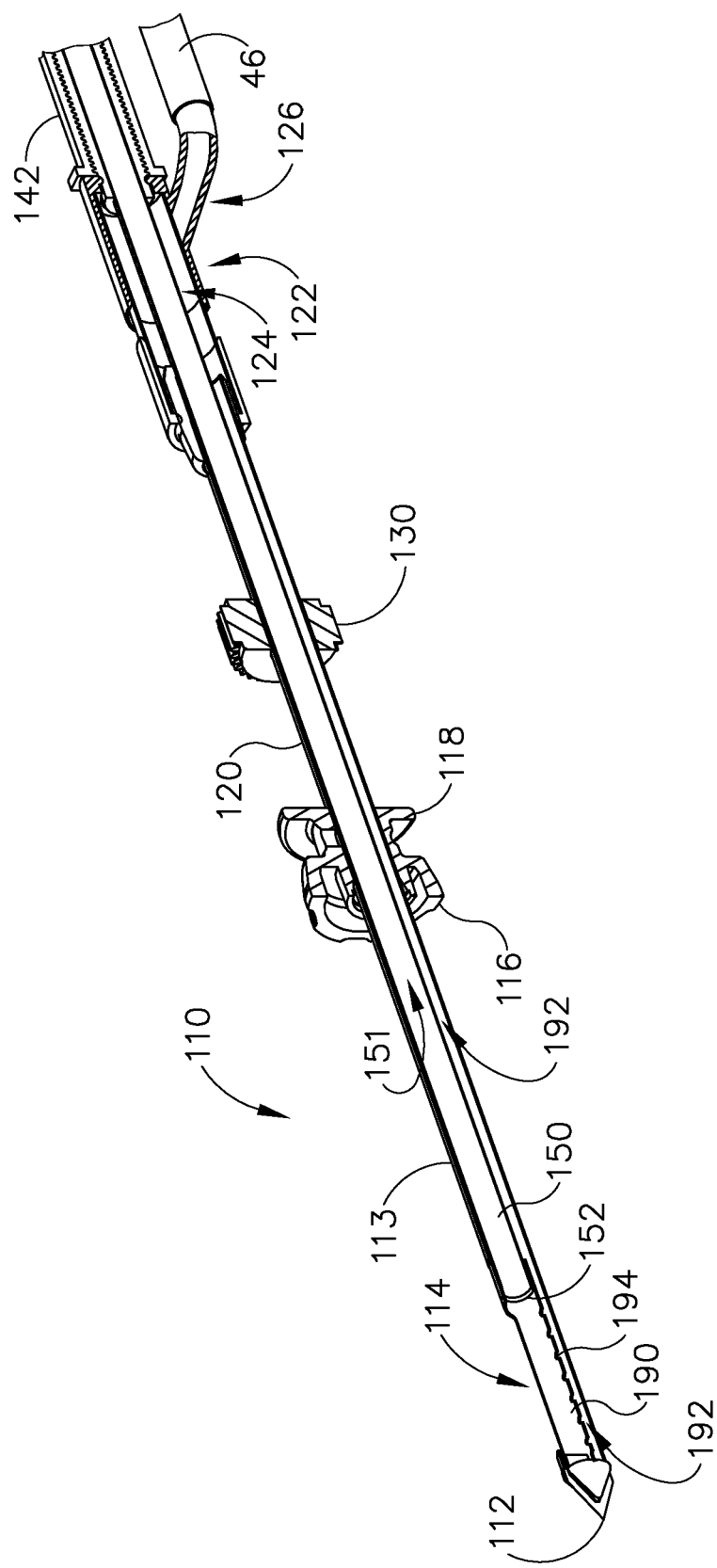
FIG. 6 depicts a cross-sectional view of a needle assembly of the probe of FIG. 4.

As best seen in FIG. 6, needle (110) also includes a longitudinal wall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion (150) of hub member (120) and is keyed to hub member (120), such that rotation of gear (130) will rotate hub member (120) and needle (110); yet hub member (120) and needle (110) may translate relative to gear (130). Gear (130) is rotatably driven by gear (212). Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As shown in FIGS. 4-7, a manifold (122) is provided at the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively.

Figure 4:
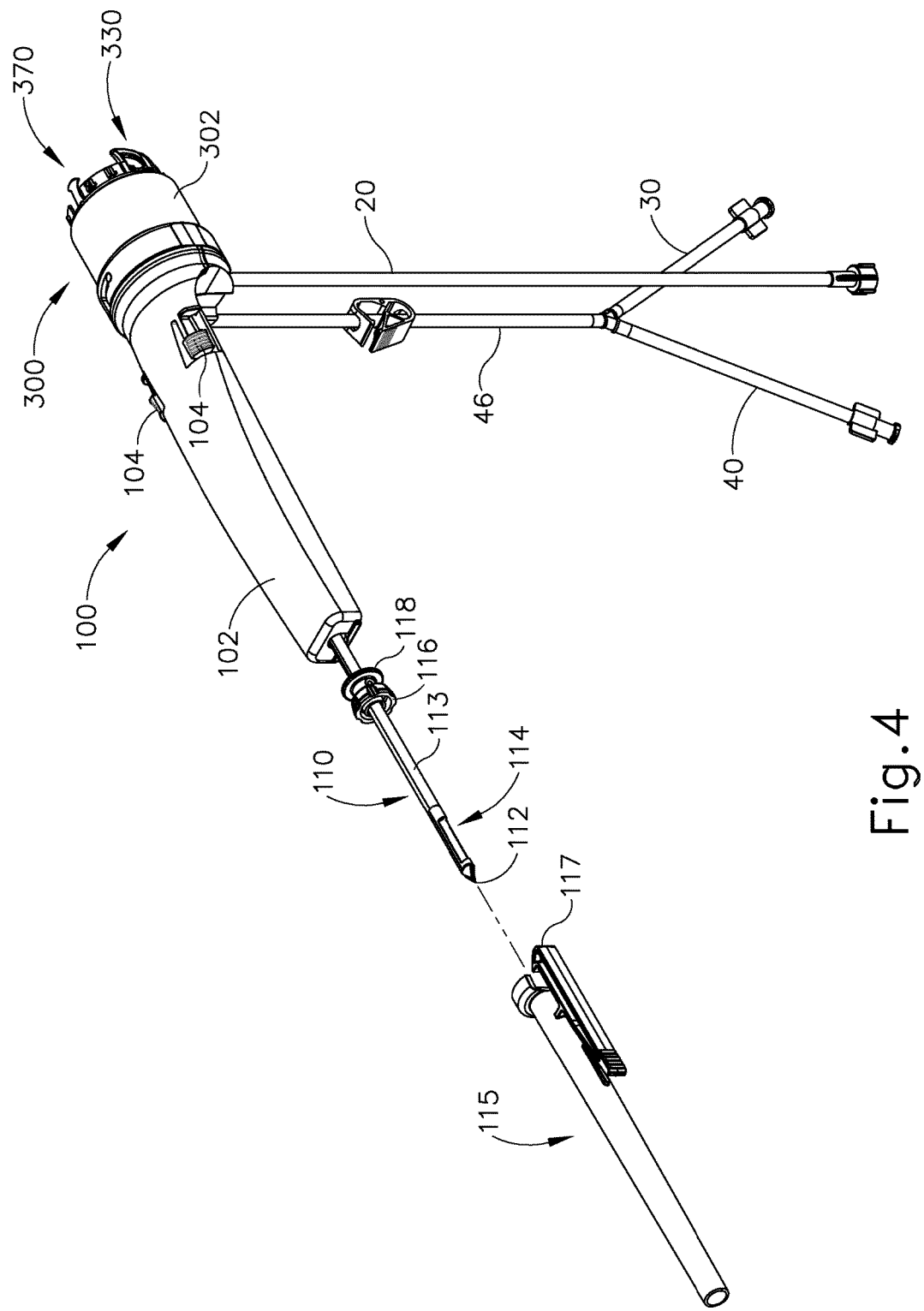
FIG. 4 depicts a perspective view of the probe of the biopsy device of FIG. 2.

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Provisional Pat. App. No. 61/566,793, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pub. No. 2008/0214955, the disclosure of which is incorporated by reference herein, and/or in accordance with the teachings of any other reference cited herein.

B. Exemplary Cutter Assembly

Figure 5:
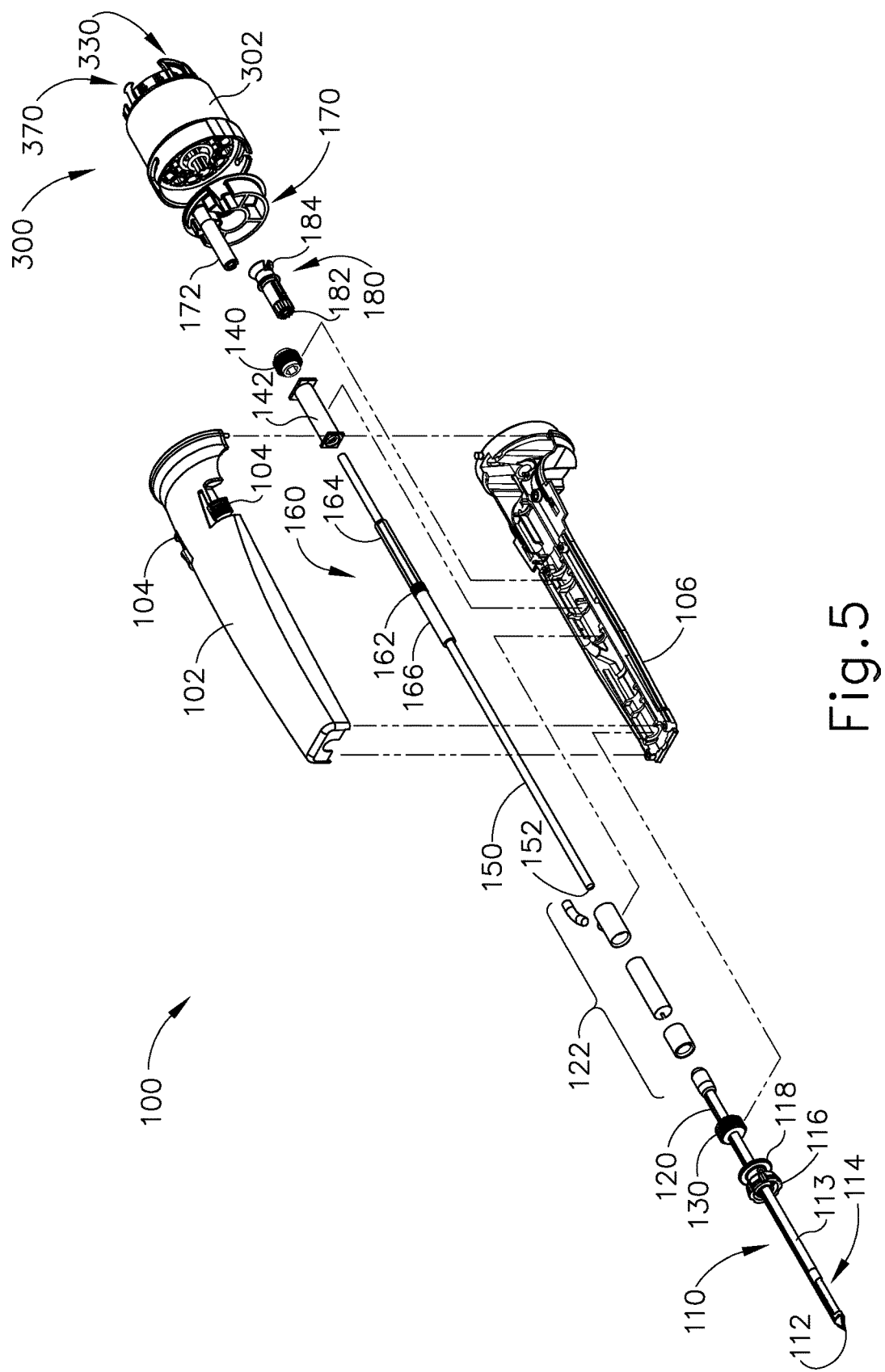
FIG. 5 depicts an exploded view of the probe of FIG. 4.
Figure 7:
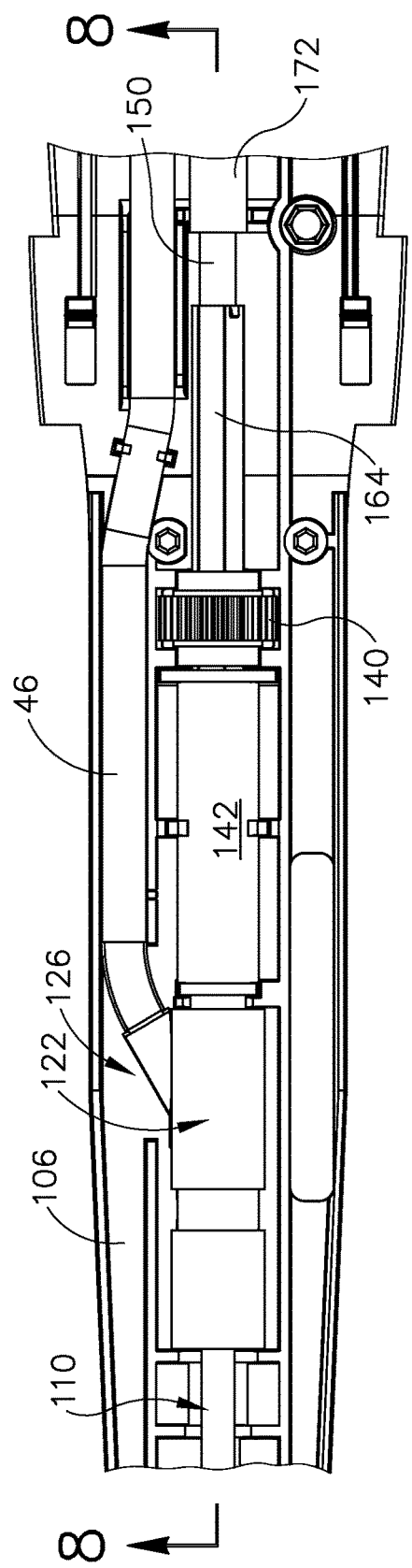
FIG. 7 depicts a partial top plan view of components of the probe of FIG. 4, with a top housing piece removed.

As noted above, cutter (150) is operable to simultaneously translate and rotate relative to needle (110) to sever a tissue sample from tissue protruding through lateral aperture (114). As best seen in FIGS. 5-7 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) such that manifold (122) maintains the fluid tight coupling between second lumen (192) and tube (46) even when cutter (150) is translated and rotated relative to manifold (122).

Figure 8:
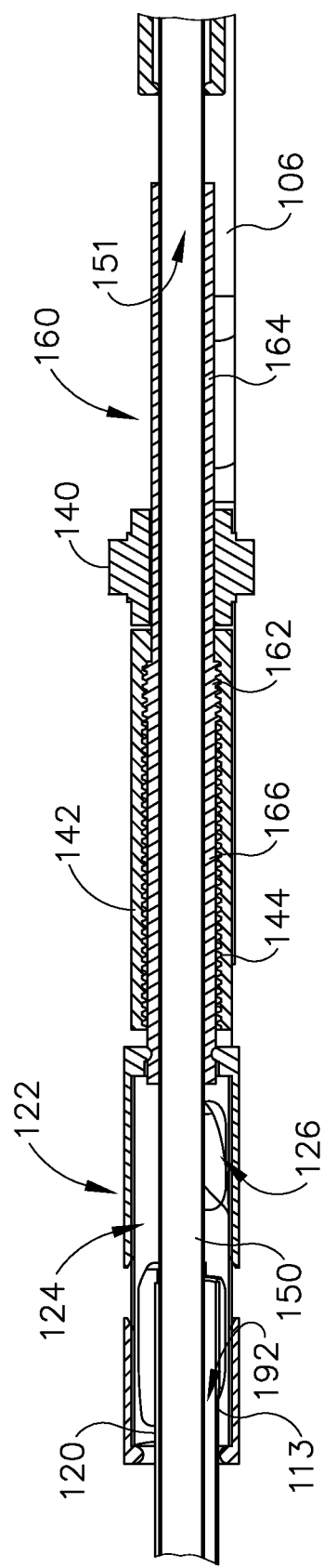
FIG. 8 depicts a side cross-sectional view of the components of FIG. 7, taken along line 8-8 of FIG. 7.

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (160) despite gear (140) being longitudinally fixed relative to chassis (160). Gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pat. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Assembly

Tissue sample holder (300) of the present example provides a plurality of discrete chambers that are configured to receive tissue samples that are severed by cutter (150) and communicated proximally through lumen (151) of cutter (150). In particular, and as will be described in greater detail below, tissue sample holder (300) includes tissue receiving trays (330) that are removably engaged with a manifold (310). Manifold (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate manifold (310) to index tissue chambers relative to lumen (151) of cutter (150) as will be described in greater detail below. A transparent cover (302) is positioned about manifold (310) and is removably secured to chassis (106). While bayonet features provide coupling between cover (302) and chassis (106), it should be understood that any suitable type of coupling may be used. Manifold (310) is freely rotatable within cover (302). However, manifold (310) is engaged with cover (302) such that manifold (310) will decouple relative to chassis (106) when cover (302) is removed from chassis (106). In other words, manifold (310) may be selectively coupled with and removed relative to chassis (106) by coupling and removing cover (302) from chassis (106).

1. Exemplary Manifold

Figure 12:
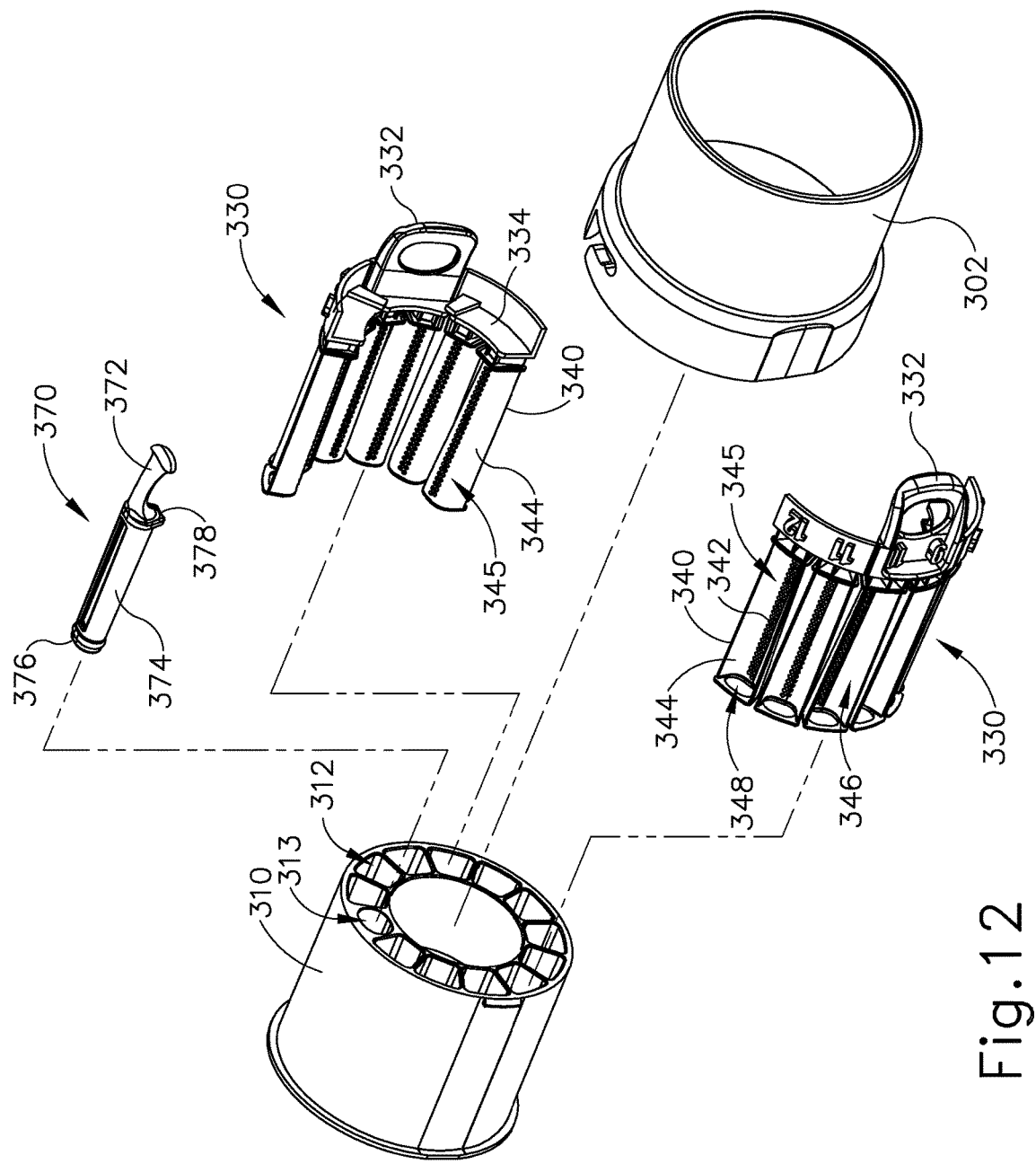
FIG. 12 depicts an exploded view of components of rotatable components of the tissue sample holder assembly of FIG. 9
Figure 13:
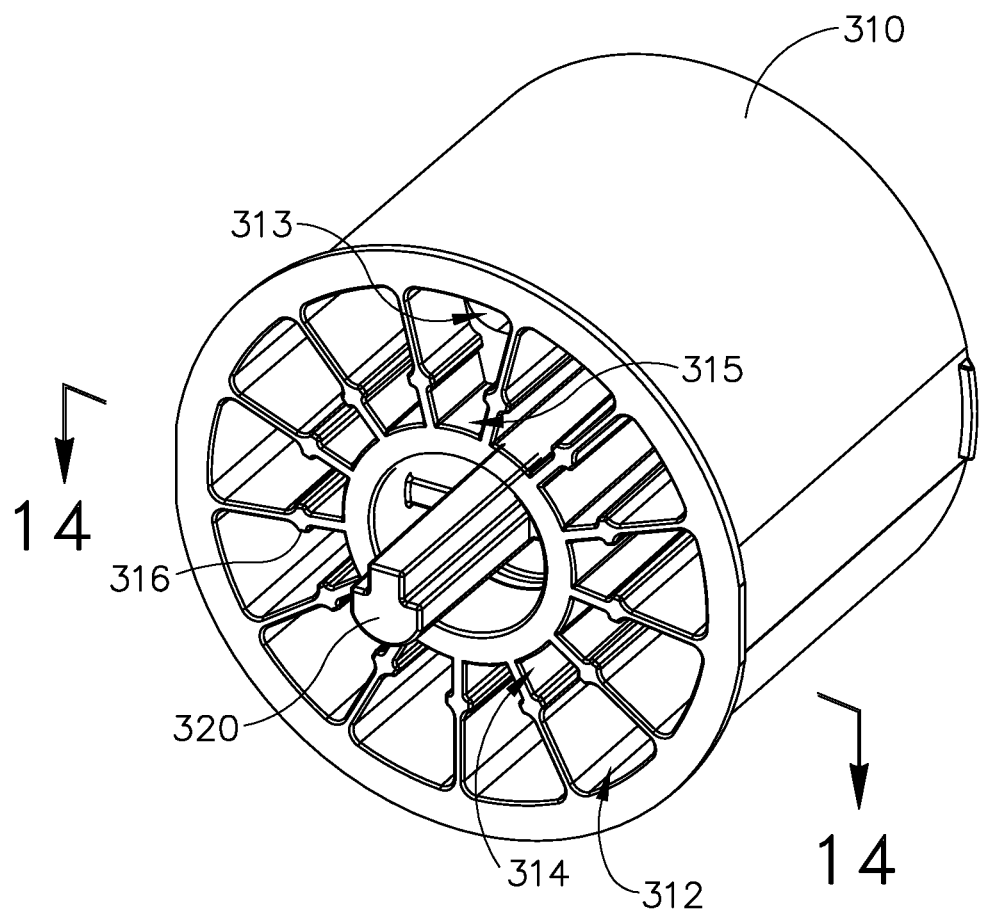
FIG. 13 depicts a perspective view of a rotatable manifold of the tissue sample holder assembly of FIG. 9.
Figure 14:
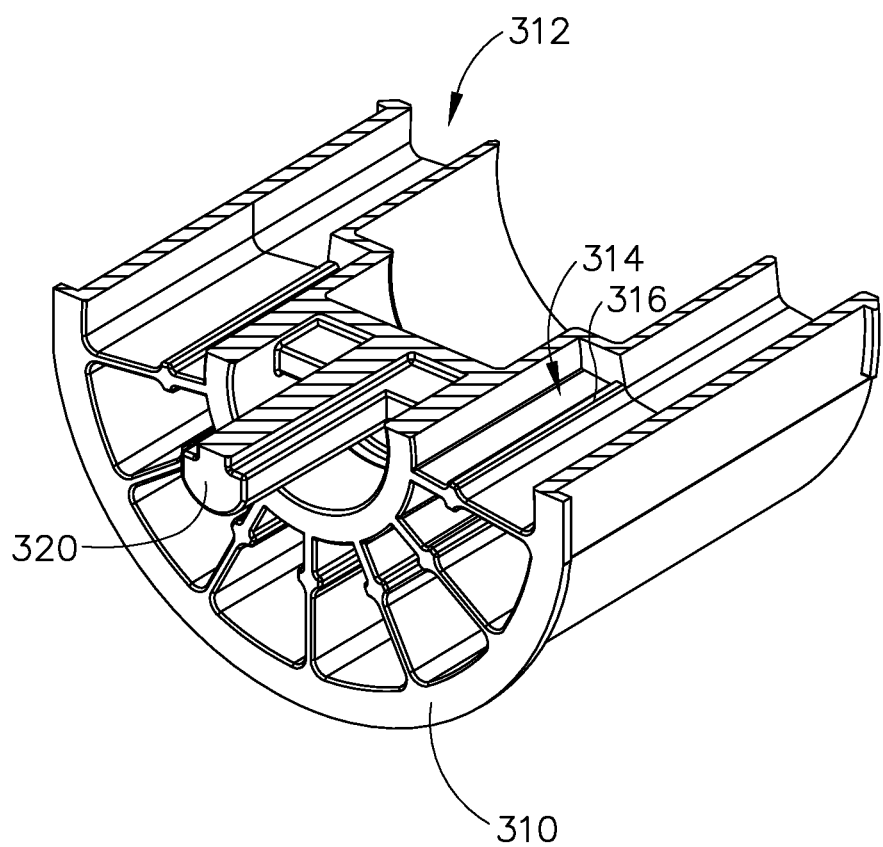
FIG. 14 depicts a cross-sectional view of the manifold of FIG. 13, taken along line 14-14 of FIG. 13.

As best seen in FIGS. 12-14, manifold (310) of the present example defines a plurality of chambers in the form of passages (312) that extend longitudinally through manifold (310) and that are angularly arrayed about the central axis of manifold (310). As best seen in FIG. 14, a lateral recess (314) is associated with a distal portion of each passage (312). Shelves (316) demarcate boundaries between each passage (312) and the associate lateral recess (314). As will be described in greater detail below, passages (312) receive trays (330) while recesses (314) provide pneumatic passages. An additional passage (313) and recess (315) are associated with a plug (370), as will also be described in greater detail below. Manifold (310) also includes a central shaft (320), which is configured to removably engage grasping feature (184). Central shaft (320) couples with grasping feature (184) upon coupling of cover (302) with chassis (106), as described above. Engagement between central shaft (320) and grasping feature (184) provides rotation of manifold (310) upon rotation of gear (182).

Figure 9:
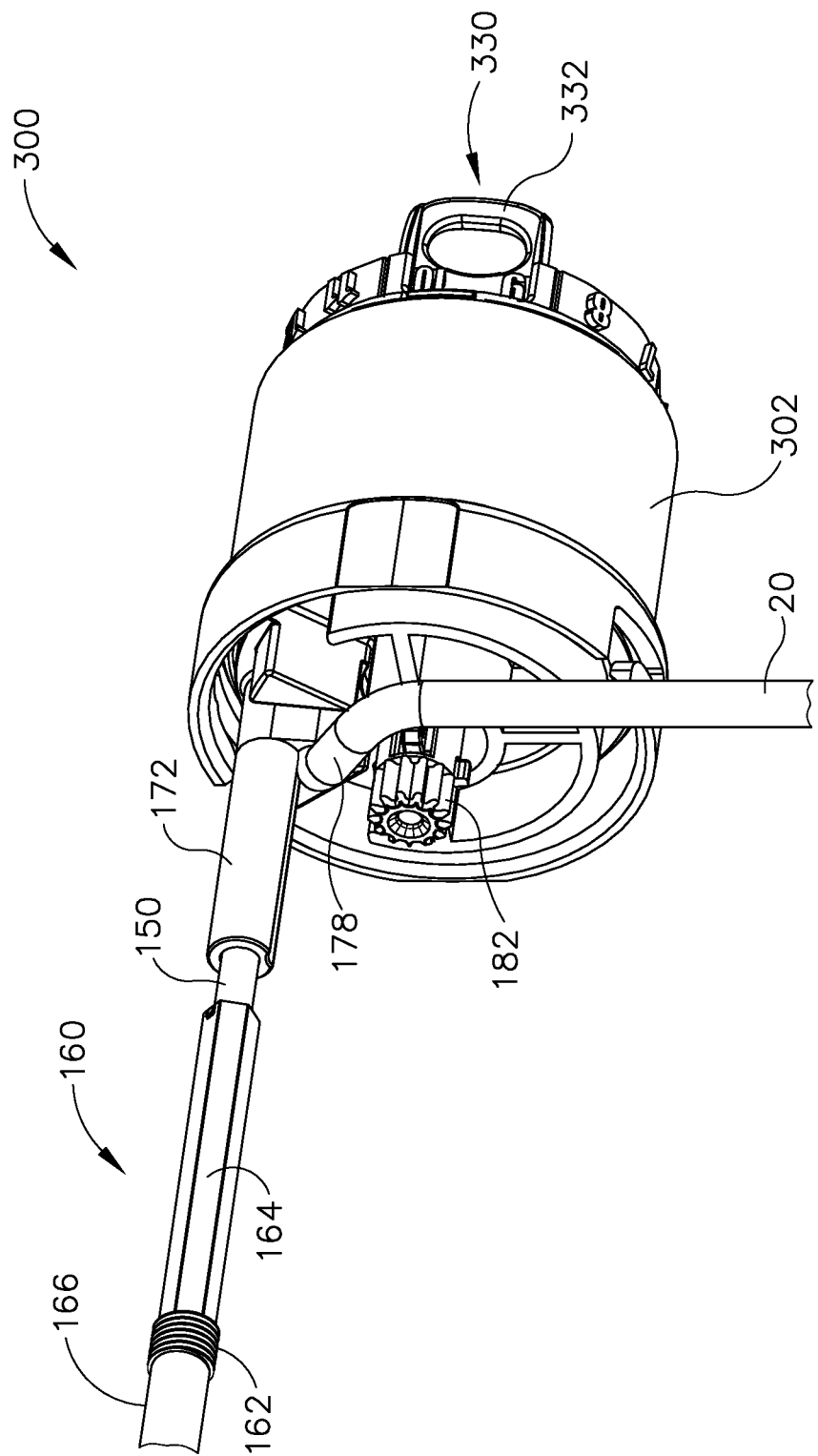
FIG. 9 depicts a perspective view of a tissue sample holder assembly of the probe of FIG. 4.
Figure 10:
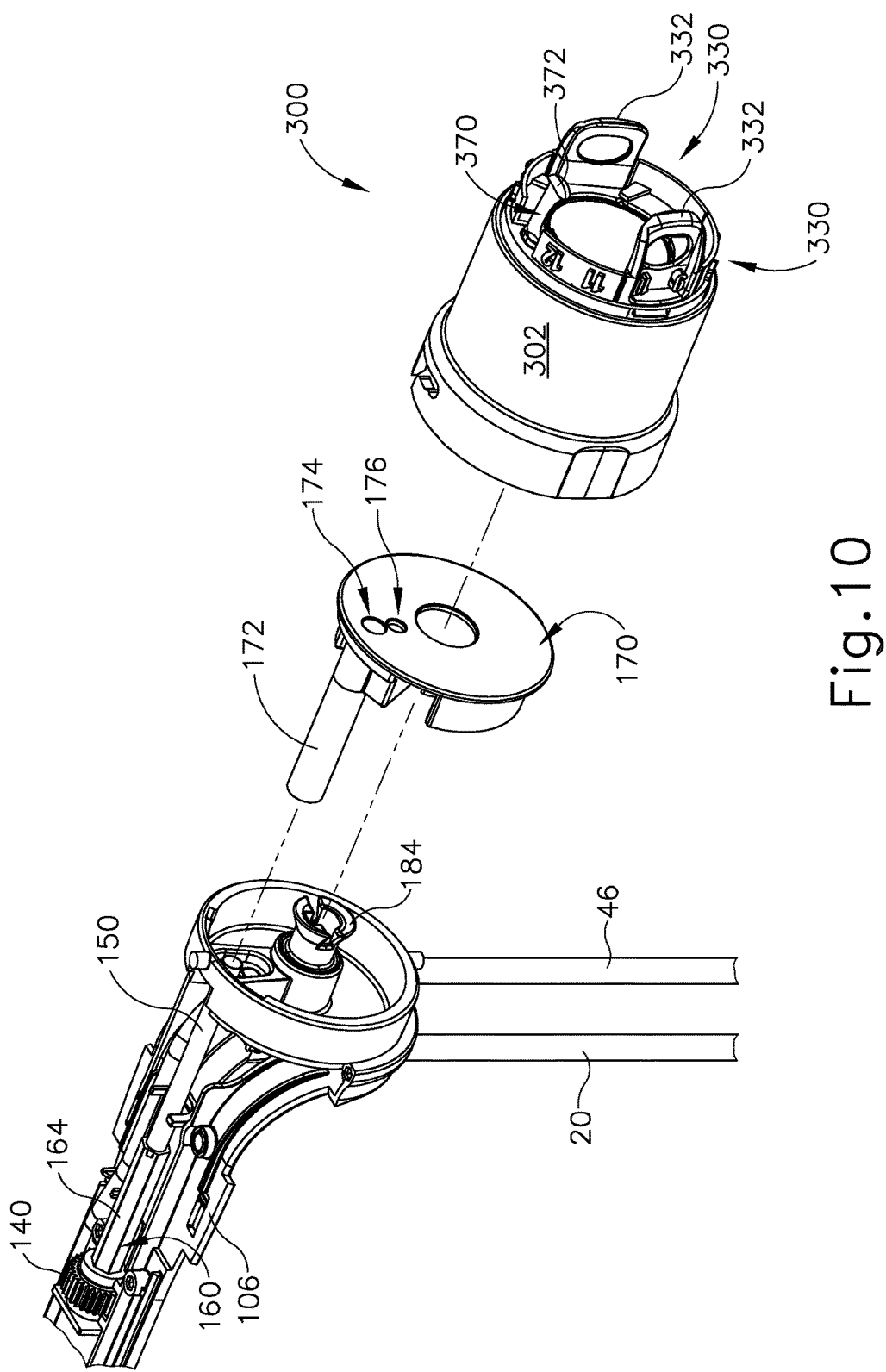
FIG. 10 depicts an exploded view of the tissue sample holder assembly of FIG. 9.
Figure 11:
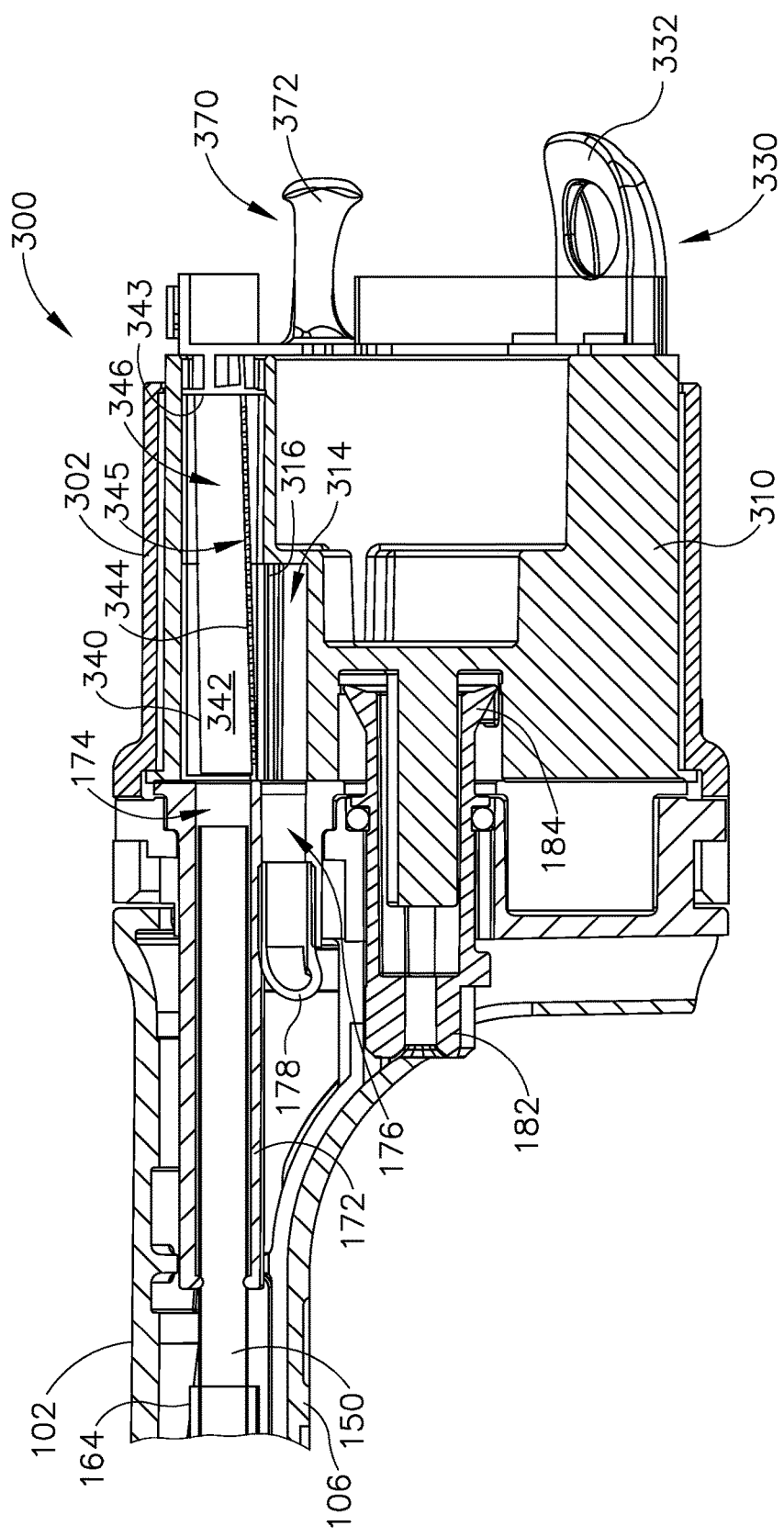
FIG. 11 depicts a side cross-sectional view of the tissue sample holder assembly of FIG. 9, with a tissue sample chamber aligned with the cutter.

As best seen in FIGS. 10-11, a sealing member (170) is provided at the proximal end of chassis (106) and interfaces with the distal face of manifold (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position. Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, manifold (310) further provides fluid communication between such recess (314, 315) and the associated passage (312, 313) at the 12 o'clock position; and thereby further to lumen (151) of cutter (150). In other words, sealing member (170) and manifold (310) cooperate to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of manifold (310), even as manifold (310) is rotated relative to sealing member (170).

2. Exemplary Tissue Holder Trays

Figure 15:
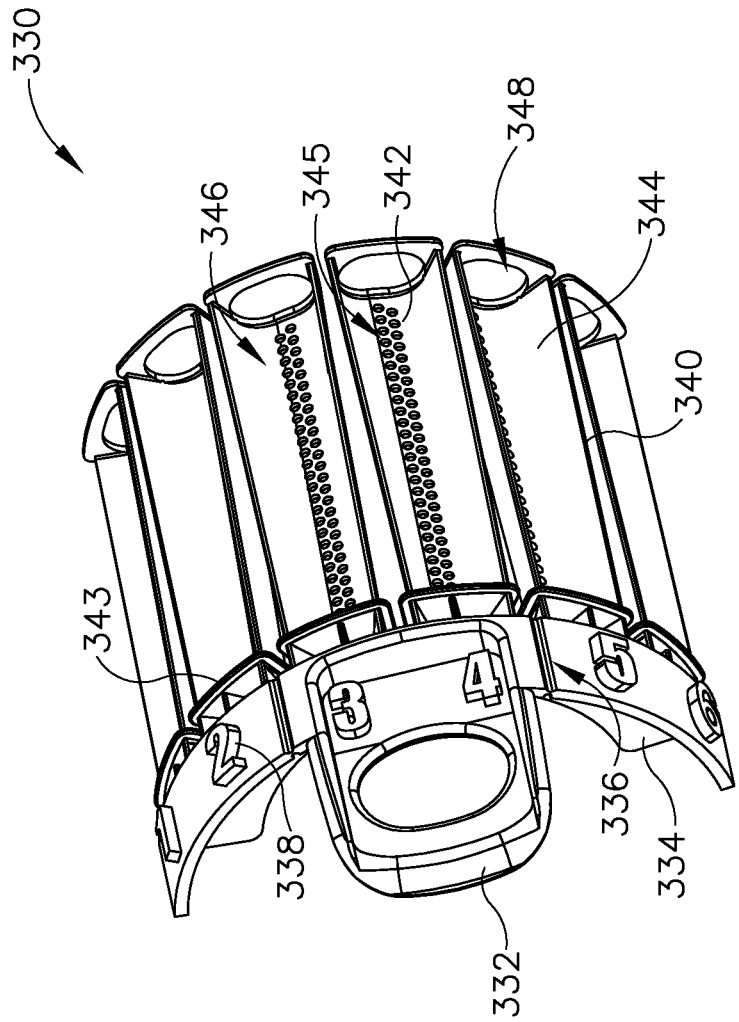
FIG. 15 depicts a perspective view of an tissue sample tray of the tissue sample holder assembly of FIG. 9.
Figure 16:
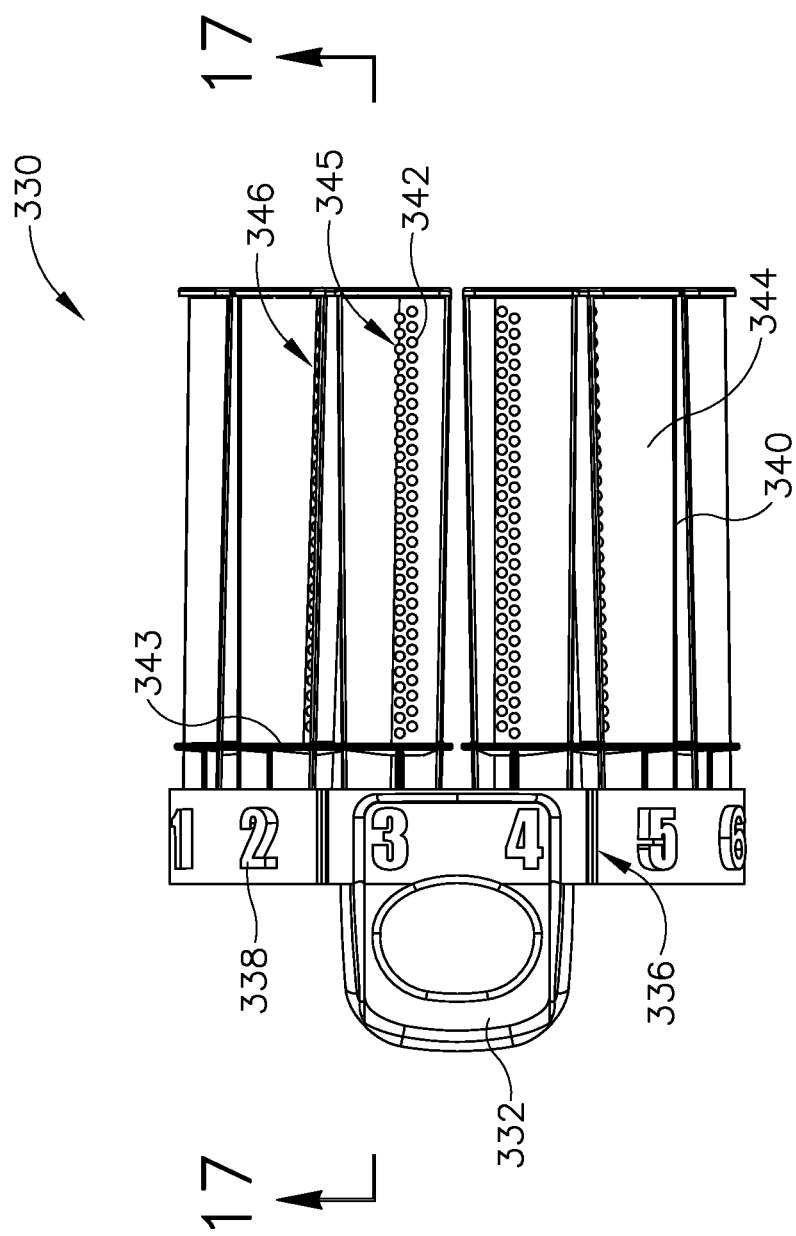
FIG. 16 depicts a top plan view of the tray of FIG. 15.
Figure 17:
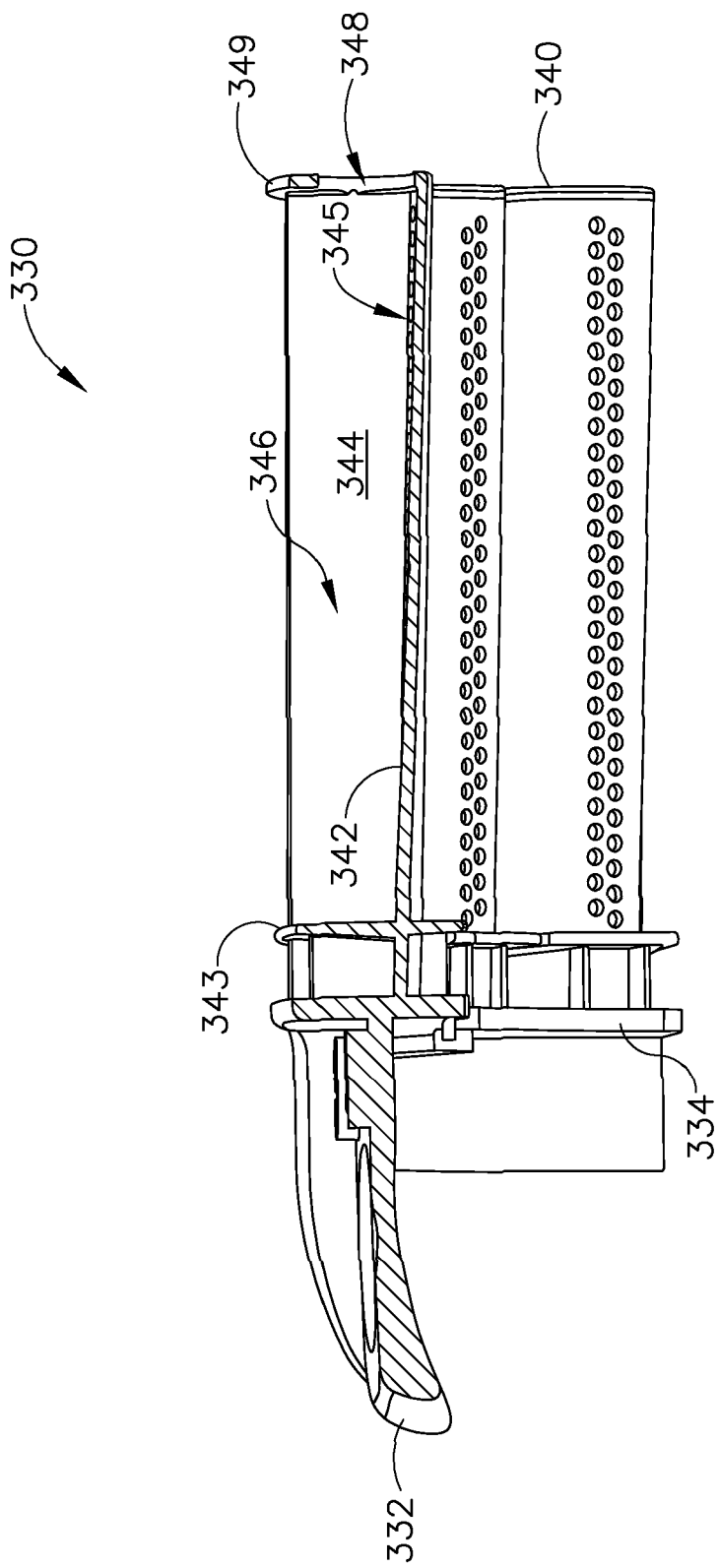
FIG. 17 depicts a cross-sectional view of the tray of FIG. 15, taken along line 17-17 of FIG. 16.

As noted above, tissue sample holder trays (330) are configured to removably engage manifold (310). As best seen in FIGS. 15-17, each tissue sample holder tray (330) of the present example includes a grip (332), a proximal wall (334), and a plurality of strips (340) extending distally from proximal wall (334). Strips (340) are sized and configured for insertion into associated passages (312) of manifold (310). Each strip (340) includes a pair of sidewalls (344) and a floor (342). Each pair of sidewalls (344) and floor (342) together define a corresponding tissue sample chamber (346). An opening (348) is provided at the distal end of each tissue sample chamber (346). Opening is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of manifold (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346). During operation of biopsy device (10), tissue samples severed by distal edge (152) of cutter (150) are communicated proximally through the lumen (151) of cutter (150) and are then deposited into the tissue sample chamber (346) that is aligned with lumen (151) of cutter (150). Manifold (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

Each strip (340) also includes a pair of wiper seals (343, 349) that seal against the interior of passage (312) when strip (340) is fully inserted into passage (312). Wiper seals (343, 349) provide a fluid tight seal for tissue sample chambers (346) and further provide frictional resistance to removal of strips (340) from manifold (310). Grips (332) are configured to facilitate removal of strips (340) from manifold (310), such as during or after a biopsy procedure to retrieve or otherwise directly observe tissue samples deposited in tissue sample chambers (346). Trays (330) also include numerical indicia (338) associated with each tissue sample chamber (346). In addition, trays (330) include pinched regions (336) that facilitate flattening of trays (330). In particular, pinched regions (336) provide sufficient flexibility to enable trays (330) to form an arcuate configuration for insertion into manifold (310); while also enabling trays (330) to form a generally flat configuration such as after trays (330) are removed from manifold (310) for inspection of tissue samples in trays (330).

Figure 18:
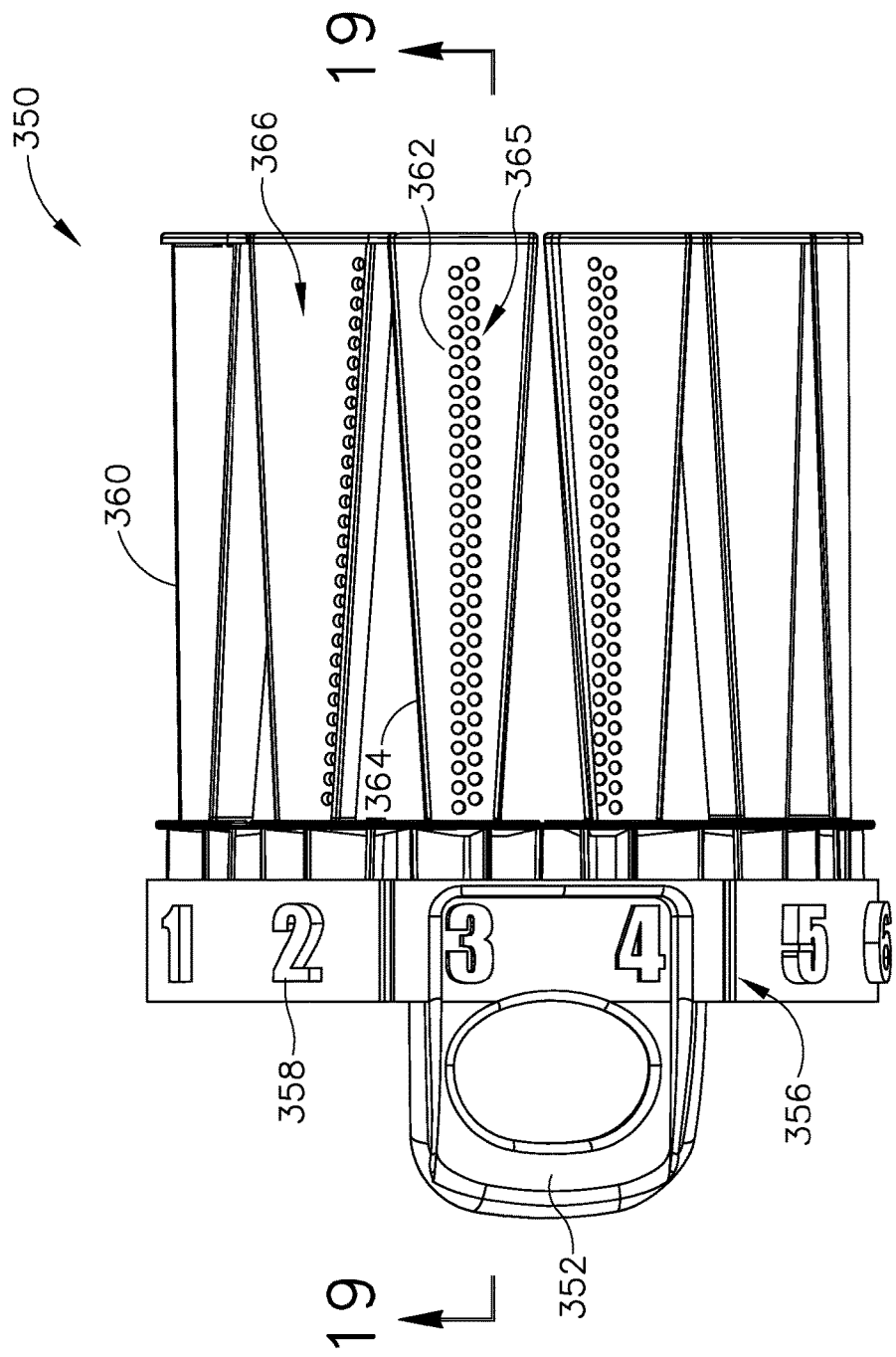
FIG. 18 depicts a top plan view of an exemplary alternative tissue sample tray.
Figure 19:
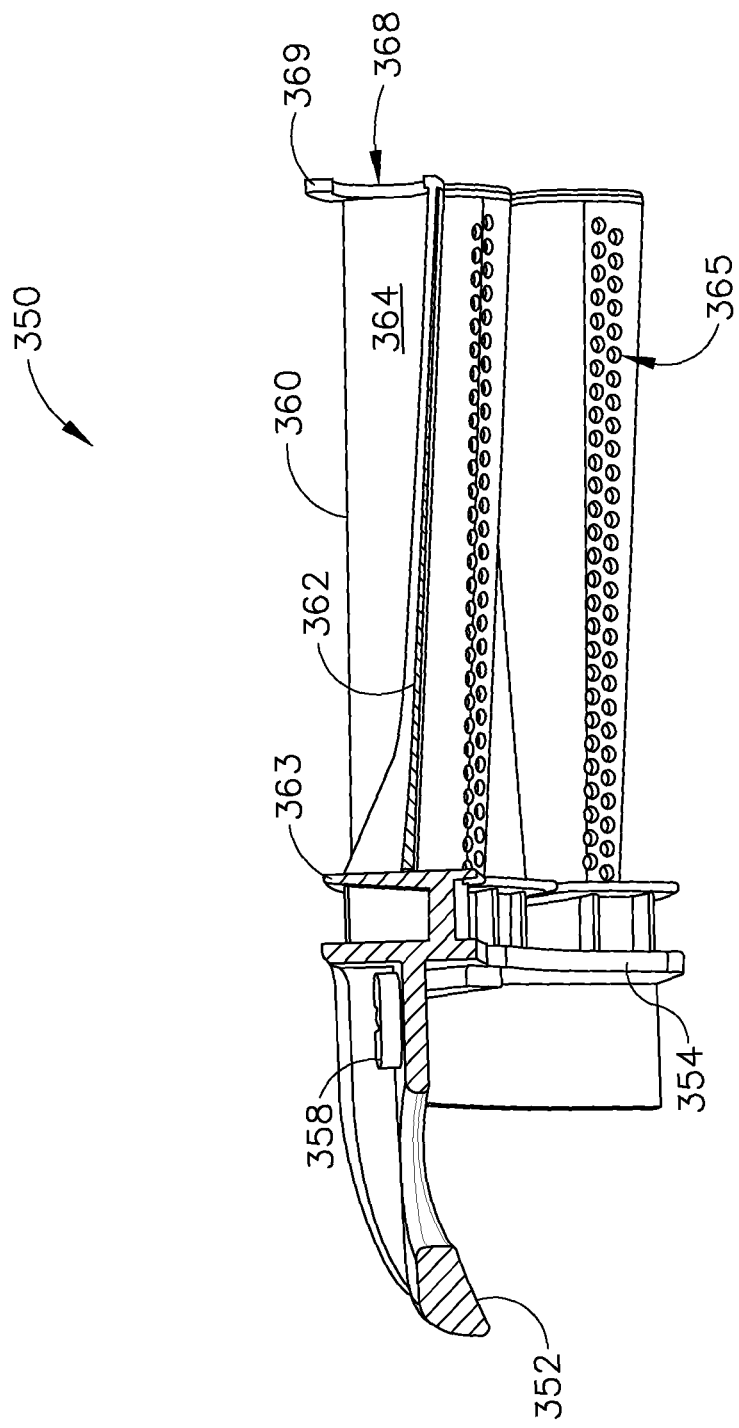
FIG. 19 depicts a cross-sectional view of the tray of FIG. 18, taken along line 19-19 of FIG. 18.

FIGS. 18-19 show an exemplary alternative tissue sample holder tray (350) that may removably engage manifold (310). Each tissue sample holder tray (350) of this example includes a grip (352), a proximal wall (354), and a plurality of strips (360) extending distally from proximal wall (354). Strips (360) are sized and configured for insertion into associated passages (312) of manifold (310). Each strip (360) includes a pair of sidewalls (364) and a floor (362). Each pair of sidewalls (364) and floor (362) together define a corresponding tissue sample chamber (366). An opening (368) is provided at the distal end of each tissue sample chamber (366). Each floor (362) includes a plurality of openings (365) that provide fluid communication between tissue sample chamber (366) of strip (360) and lateral recess (314) of the passage (312) associated with strip (360). Thus, vacuum, atmospheric air, etc. that is communicated to opening (176) via tube (20) is further communicated to lumen (151) of cutter (150) via lateral recess (314), openings (365), and tissue sample chamber (366).

Each strip (360) also includes a pair of wiper seals (363, 369) that seal against the interior of passage (312) when strip (360) is fully inserted into passage (312). Wiper seals (363, 369) provide a fluid tight seal for tissue sample chambers (366) and further provide frictional resistance to removal of strips (360) from manifold (310). Grips (352) are configured to facilitate removal of strips (360) from manifold (310), such as during or after a biopsy procedure to retrieve or otherwise directly observe tissue samples deposited in tissue sample chambers (366). Trays (350) also include numerical indicia (358) associated with each tissue sample chamber (366). In addition, trays (350) include pinched regions (356) that facilitate flattening of trays (350). In particular, pinched regions (356) provide sufficient flexibility to enable trays (350) to form an arcuate configuration for insertion into manifold (310); while also enabling trays (350) to form a generally flat configuration such as after trays (350) are removed from manifold (310) for inspection of tissue samples in trays (350).

It should be understood from the foregoing that trays (330) are substantially similar to trays (350). However, significant differences include the configurations of floor (364) and sidewall (362) as compared to the configurations of floor (344) and sidewall (342). In particular, as best seen by comparing FIG. 18 to FIG. 16, sidewalls (362) form a relatively aggressive taper along the length of strips (360), as compared to strips (340). This taper provides width at the proximal end of chamber (366) that is significantly less than the width at the distal end of chamber (366). As best seen in FIG. 18, this taper is also augmented by floor (364), which angles upwardly along the length of strip (360). Angled floor (364) provides a height at the proximal end of chamber (366) that is significantly less than the height at the distal end of chamber (366). It should therefore be understood that the angled orientations of floor (364) and sidewalls (342) provide a cross-sectional area of chamber (366) that reduces along the length of chamber (366), with the cross-sectional area of chamber (366) being significantly smaller at the proximal end of chamber (366) as compared to the cross-sectional area at the distal end of chamber (366). By contrast, the cross-sectional area of chambers (346) in tray (330) is relatively more consistent along its length. While a slight taper is provided by walls (342) and floor (344), that taper is far less aggressive than the taper provided by walls (362) and floor (364).

In some versions, trays (330) are used with biopsy devices (10) having needles (110) with a relatively large diameter while trays (360) re used with biopsy devices (10) having needles (110) with a relatively small diameter. For instance, trays (330) may be configured for use with 8 gauge needles (110) while trays (350) are configured for use with 10 gauge needles (110). The relatively aggressive taper provided within chambers (366) may assist in keeping relatively thin severed tissue samples substantially straight when such relatively thin tissue samples are deposited in chambers. For instance, the aggressive taper in chambers (366) may assist in providing a more gradual deceleration of tissue samples as they are deposited in chambers (366), thereby reducing a tendency that such tissues samples might otherwise have to become smashed, curled up, or otherwise disfigured if they were to enter chambers (346) at a relatively higher speed due to the lack of such an aggressive taper.

It should be understood that manifold (310) and/or trays (330, 350) may be configured in numerous other ways. By way of example only, manifold (310) and/or trays (330, 350) may be configured in accordance with at least some of the teachings of U.S. Pat. Pub. No. 2008/0214955, the disclosure of which is incorporated by reference herein. As another merely illustrative example, manifold (310) and/or trays (330, 350) may be configured in accordance with at least some of the teachings of U.S. Pat. Pub. No. 2010/0160824, the disclosure of which is incorporated by reference herein. It should also be understood that tissue sample holder (300) need not necessarily position chambers (346, 366) coaxially with lumen (151) of cutter (150). Tissue sample holder (300) may index chambers (346, 366) relative to cutter (150) in any other suitable fashion. For instance, chambers (346, 366) may extend along axes that are always offset from the axis of lumen (151), along axes that are oblique or perpendicular relative to the axis of lumen (151), or along other axes. Similarly, it should be understood that manifold (310) may rotate about an axis that is oblique or perpendicular relative to the axis of lumen (151). Still other suitable configurations will be apparent to those of ordinary skill in the art in view of the teachings herein.

3. Exemplary Flexible Tissue Holder Trays

Figure 22:
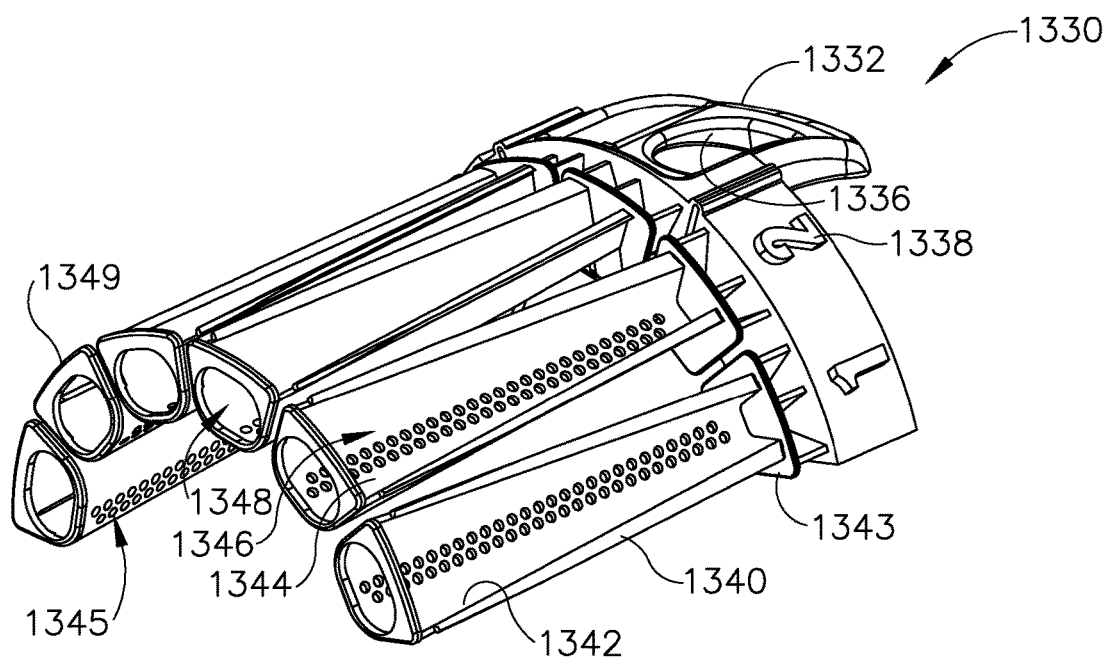
FIG. 22 depicts a top perspective view of an exemplary alternative tissue sample tray.
Figure 23:
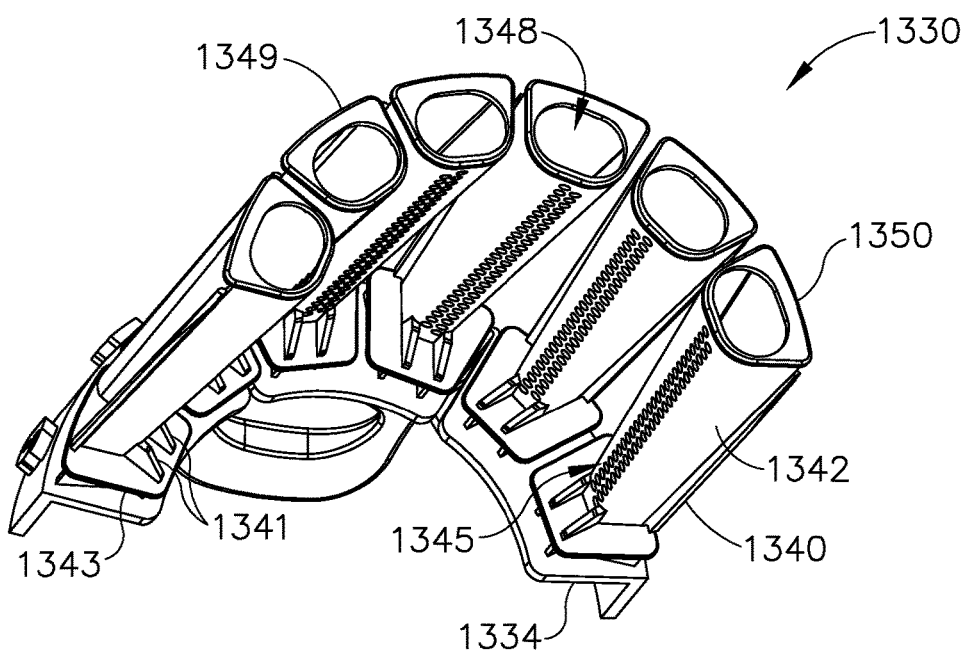
FIG. 23 depicts a bottom perspective view of the tissue sample tray of FIG. 22.

In some instances, it may be desirable for tissue sample holder trays (310, 350) to be flexible to facilitate visualization of the tissue samples after tissue sample holder trays (310, 350) are removed from manifold (310). FIGS. 22-23 show an exemplary alternative tissue sample holder tray (1330), similar to tissue sample holder tray (330), except that tissue sample holder tray (1330) includes additional flexible features. Each tissue sample holder tray (1330) of this example includes a grip (1332), a proximal wall (1334), and a plurality of strips (1350) extending distally from proximal wall (1334). Strips (1350) are sized and configured for insertion into associated passages (312) of manifold (310). Each strip (1350) includes a pair of sidewalls (1342) and a floor (1344). Each pair of sidewalls (1342) and floor (1344) together define a corresponding tissue sample chamber (1346). An opening (1348) is provided at the distal end of each tissue sample chamber (1346). Each floor (1344) includes a plurality of openings (1345) that provide fluid communication between tissue sample chamber (1346) of strip (1350) and lateral recess (314) of the passage (312) associated with strip (360). Thus, vacuum, atmospheric air, etc. that is communicated to opening (176) via tube (20) is further communicated to lumen (151) of cutter (150) via lateral recess (314), openings (1345), and tissue sample chamber (1346).

Each strip (1350) also includes a pair of wiper seals (1343, 1349) that seal against the interior of passage (312) when strip (1350) is fully inserted into passage (312). Wiper seals (1343, 1349) provide a fluid tight seal for tissue sample chambers (1346) and further provide frictional resistance to removal of strips (1350) from manifold (310). As best seen in FIG. 23, a pair of ribs (1341) extends from floor (1344) of each strip (1350) to each wiper seal (1343). This may prevent the sealing surface of wiper seal (1343) from flexing when strip (1350) is inserted within the interior of passage (312) to maintain the seal against passage (312). Although two ribs (1341) are shown in the present example, any other suitable number of ribs (1341) may be used with each strip (1350).

Figure 24:
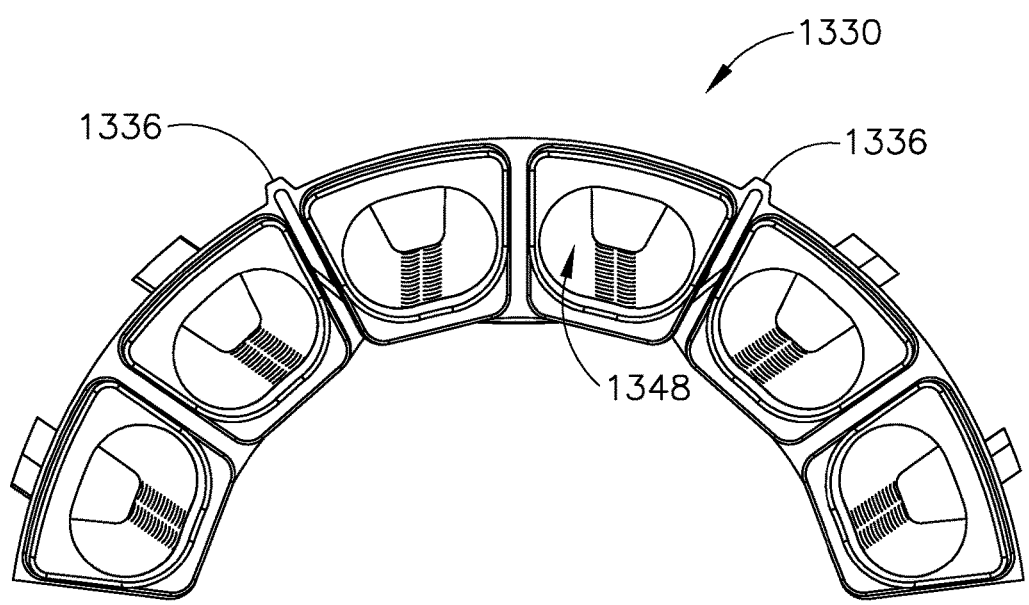
FIG. 24 depicts a front view of the tissue sample tray of FIG. 22.
Figure 25:
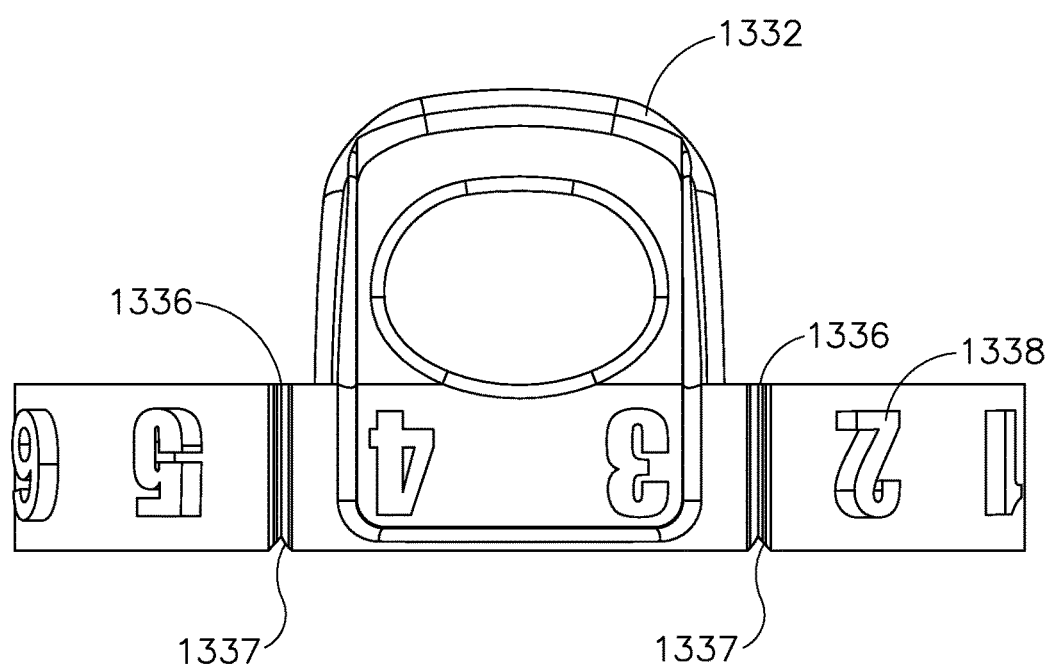
FIG. 25 depicts a top plan view of a grip of the tissue sample tray of FIG. 22.
Figure 26:
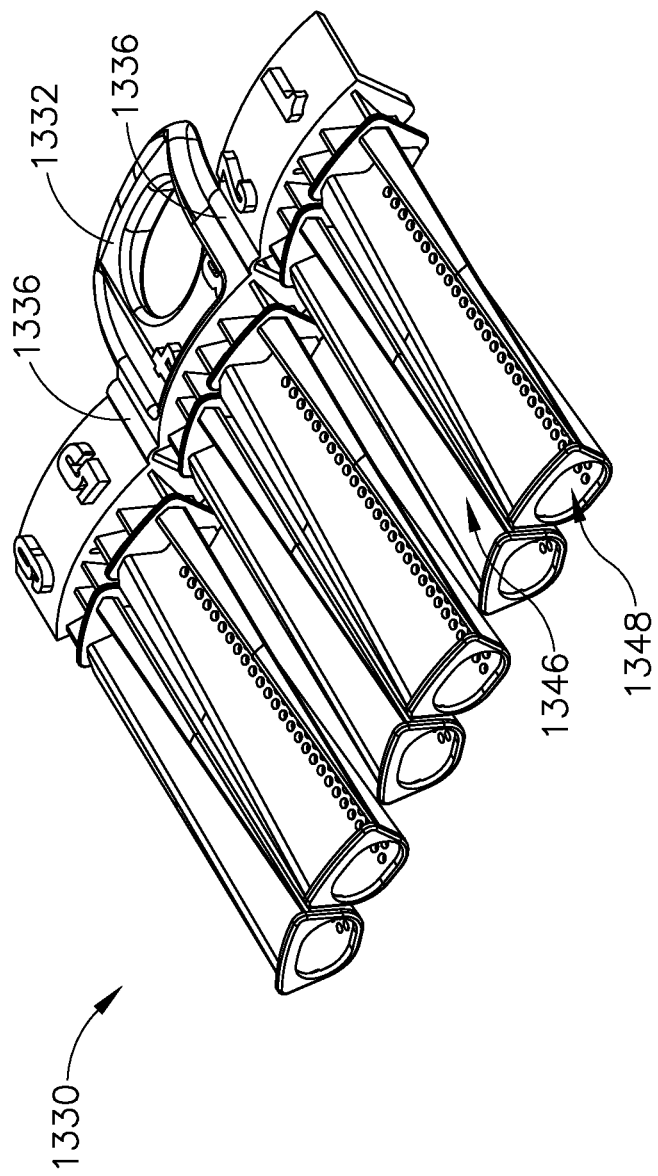
FIG. 26 depicts a perspective view of the tissue sample tray of FIG. 22 in a flattened position.

Grips (1332) are configured to facilitate removal of strips (1350) from manifold (310), such as during or after a biopsy procedure to retrieve or otherwise directly observe tissue samples deposited in tissue sample chambers (1346). Trays (1330) also include numerical indicia (1338) associated with each tissue sample chamber (1346). In addition, trays (1330) include living hinges (1336) that facilitate flattening of trays (1330), as shown in FIGS. 24-25. In particular, living hinges (1336) provide sufficient flexibility to enable trays (1330) to form an arcuate configuration for insertion into manifold (310); while also enabling trays (1330) to form a generally flat configuration such as after trays (1330) are removed from manifold (310) for inspection of tissue samples in trays (1330), as shown in FIG. 26. In the present example, living hinges (1336) extend between each pair of strips (1350). However, living hinges (1336) may be positioned between each strip (1350) or in any other suitable pattern as will be apparent to one with ordinary skill in the art based on the teachings herein. Of course, living hinges (1336) may be comprised of any other structure suitable to facilitate flattening of trays (1330) such as pin hinges, or a notch as described above. As best seen in FIG. 25, each living hinge (1336) comprises a notch (1337) at a distal end of each hinge (1336). Accordingly, notches (1337) allow hinges (1336) to flex outwardly to splay strips (1350) outwardly when tray (1350) is flexed to the flattened configuration.

Figure 27:
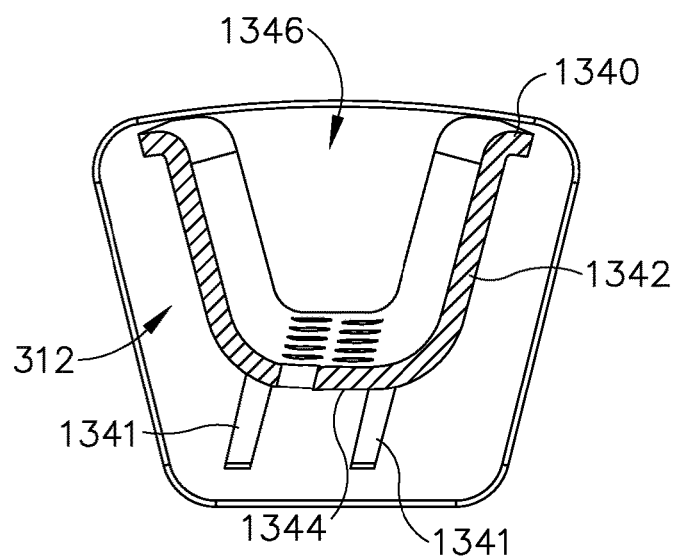
FIG. 27 depicts a cross-sectional view of a tray of the tissue sample tray of FIG. 22 within a manifold chamber.
Figure 28:
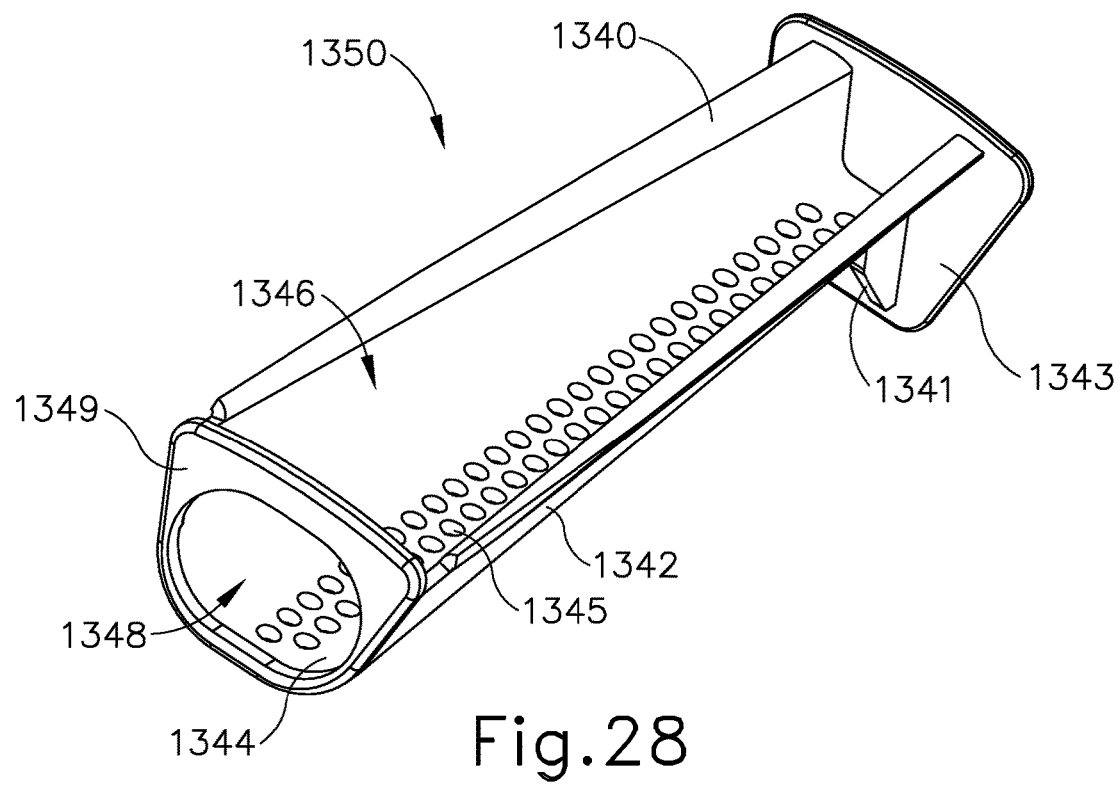
FIG. 28 depicts a perspective view of the tray of FIG. 27.

Each strip (1350) further comprises a wing (1340) extending outwardly from side walls (1342), as shown in FIGS. 27-28. Wings (1340) extend substantially along the length of side walls (1342), as shown in FIG. 28. Side walls (1342) of tray (1330) are longer than side walls (342) of tray (330) such that side walls (1342) extend within passage (312) of manifold (310) to allow wings (1340) to engage the top surface of passage (312), as shown in FIG. 27. Wings (1340) thereby create a seal around the top/outer portion of each chamber (1346) within passage (312) of manifold (310), such that openings (1345) provide the only fluid communication passage for chamber (1346). Strips (1350) may also be modified to create a seal with the side surfaces of passage (312).

Figure 29:
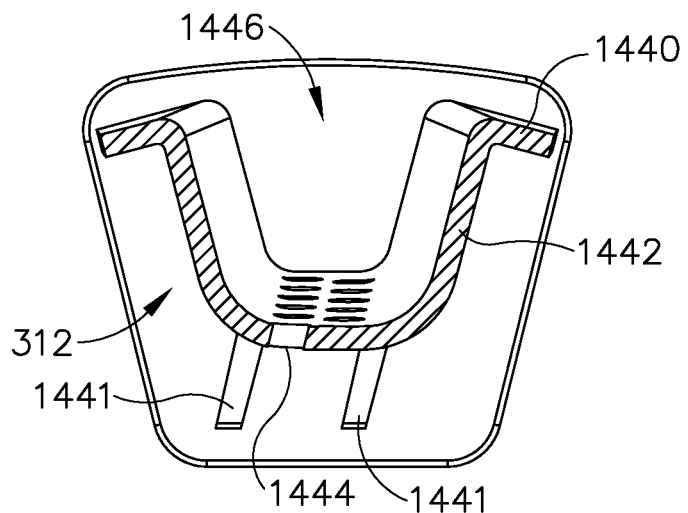
FIG. 29 depicts a cross-sectional view of another exemplary tray of a tissue sample tray within a manifold chamber.
Figure 30:
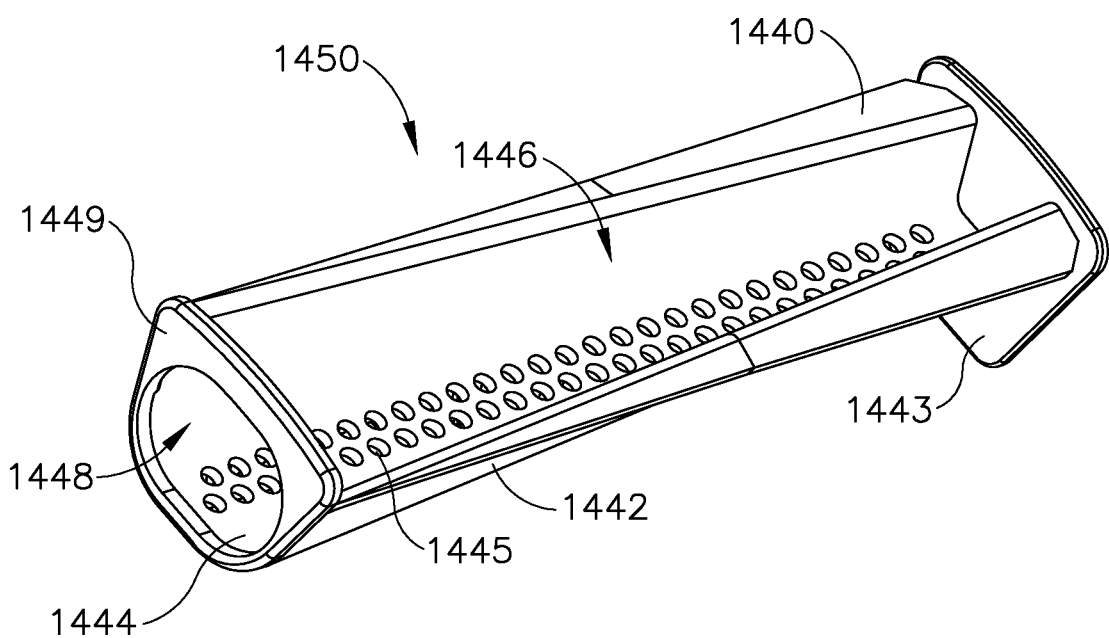
FIG. 30 depicts a perspective view of the tray of FIG. 29.

FIGS. 29-30 show exemplary strips (1450) with wings (1440) that engage the side surfaces of passage (312). Strip (1450) is similar to strip (1350), except that side walls (1442) of strip (1450) do not extend as high from floor (1444) as side walls (1342) of strip (1350). Wings (1440) of strip (1450) extend outwardly from a top portion of side walls (1442) along substantially the length of side walls (1442). Wings (1440) extend further outwardly from side walls (1442) than wings (1340) of strip (1350) such that wings (1440) engage the side surfaces of passage (312) of manifold (310), as shown in FIG. 29. Accordingly, wings (1440) create a seal around the top/outer portion of each chamber (1446) within passage (312) of manifold (310), such that openings (1445) provide the only fluid communication passage for chamber (1446).

4. Exemplary Accessory Chamber and Plug

Figure 20:
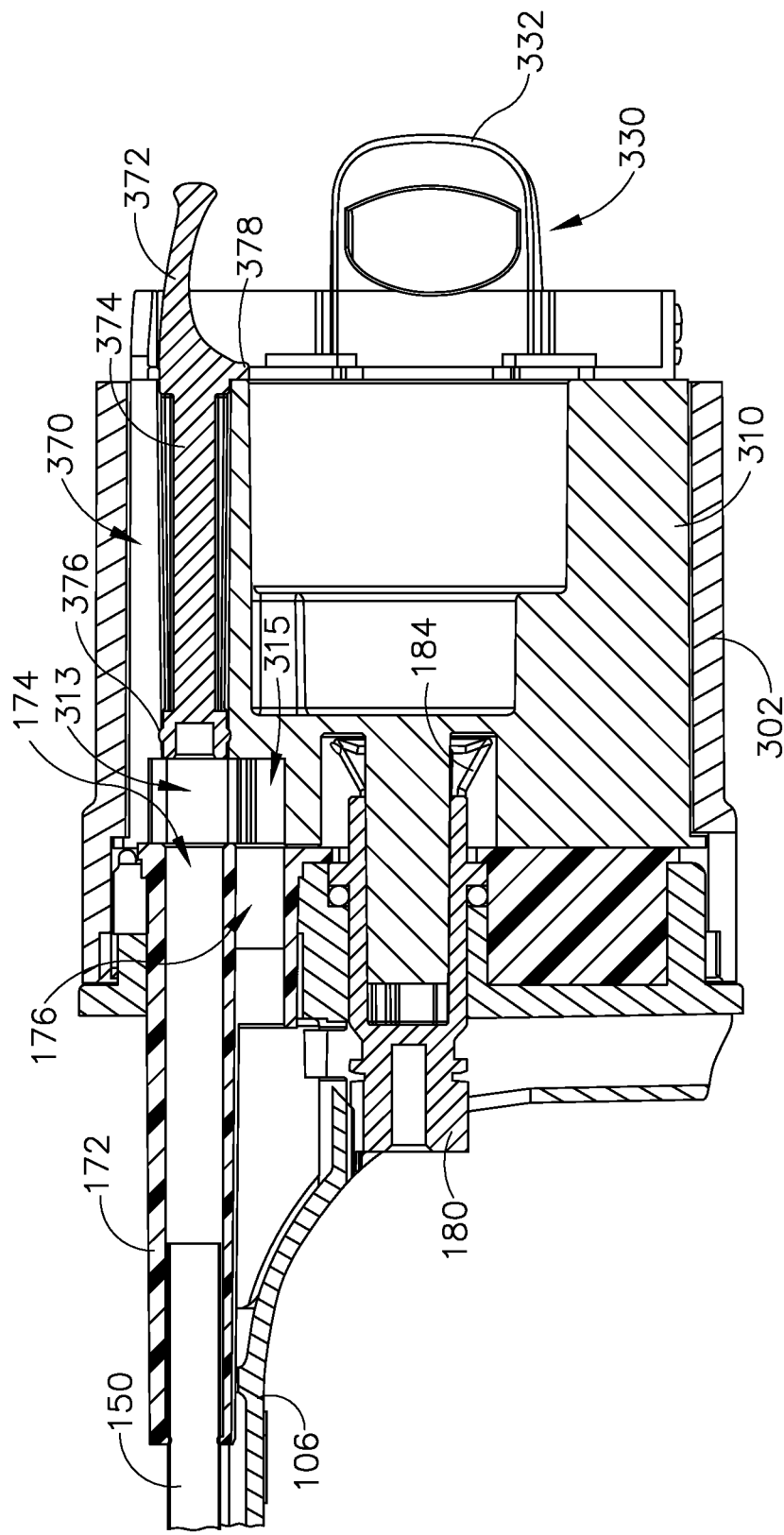
FIG. 20 depicts a side cross-sectional view of the tissue sample holder assembly of FIG. 9, with a plug aligned with the cutter.

As best seen in FIGS. 12 and 20 and as noted above, tissue sample holder (300) of the present example includes a plug (370) that is received in a dedicated passage (313) of manifold (310). Plug (370) includes a grip (372) and a longitudinally extending body (374). Body (374) extends through part of the length of passage (313), distally terminating at the longitudinal position corresponding with the proximal end of recess (315). Plug (370) includes a pair of seals (376, 378) that seal against the interior of passage (313) when plug (370) is fully inserted in passage (313). Seals (376, 378) thus keep passage (313) fluid tight when plug (370) is inserted in passage (313). Passage (313) is configured to receive the shaft of a biopsy site marker applier. Passage (313) may also receive an instrument for delivering medicine, etc. to a biopsy site. By way of example only, passage (313) may receive an adapter configured to provide an interface between passage (313) and a conventional medicine delivery device. An example of such an adapter and other uses/configurations for a passage like passage (313) are described in U.S. Pat. Pub. No. 2008/0221480, the disclosure of which is incorporated by reference herein. Plug (370) and/or passage (313) may also be configured and operable in accordance with at least some of the teachings of U.S. Non-Provisional patent application Ser. No. 13/205,189, the disclosure of which is incorporated by reference herein. Still other suitable configurations will be apparent to those of ordinary skill in the art in view of the teachings herein. In some other versions, plug (370) and/or passage (313) are simply omitted.

5. Exemplary Parking Pawl

Figure 21:
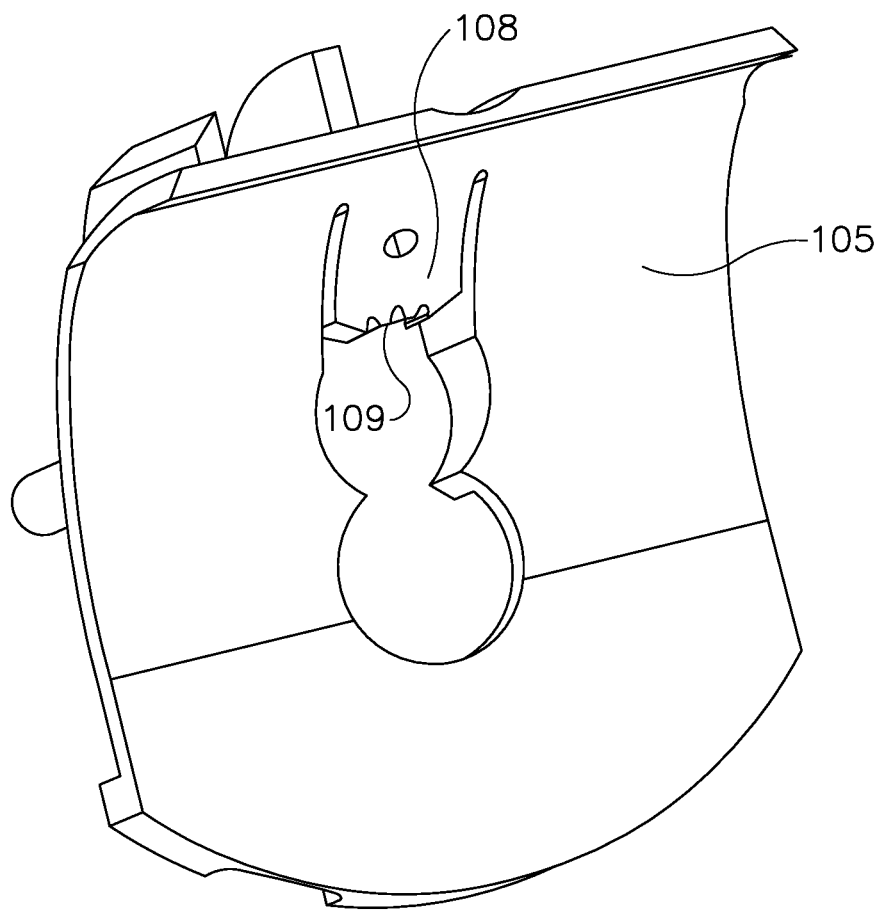
FIG. 21 depicts a perspective view of a component of the probe of FIG. 4 including a parking pawl.

As best seen in FIGS. 3 and 21, a rear plate (105) is provided at the proximal end of chassis (106). Rear plate (105) includes a pawl (108) having teeth (109) that are configured to engage the splines of gear (182) of tissue sample holder (300). Pawl (108) is resiliently biased to urge teeth (109) into engagement with the splines of gear (182). This engagement prevents gear (182) from rotating, thereby substantially securing the rotational position of manifold (310). As shown in FIGS. 3 and 23-24, holster (200) includes a cam (209) that is configured to disengage teeth (109) from the splines of gear (182) when probe (100) is coupled with holster (200). Manifold (310) is thus free to rotate under the influence of drive gear (240) when probe (100) is coupled with holster (200). Still other suitable ways in which the rotational position of manifold (310) may be selectively fixed will be apparent to those of ordinary skill in the art in view of the teachings herein.

IV. Exemplary Tissue Sample Imaging System

Figure 31:
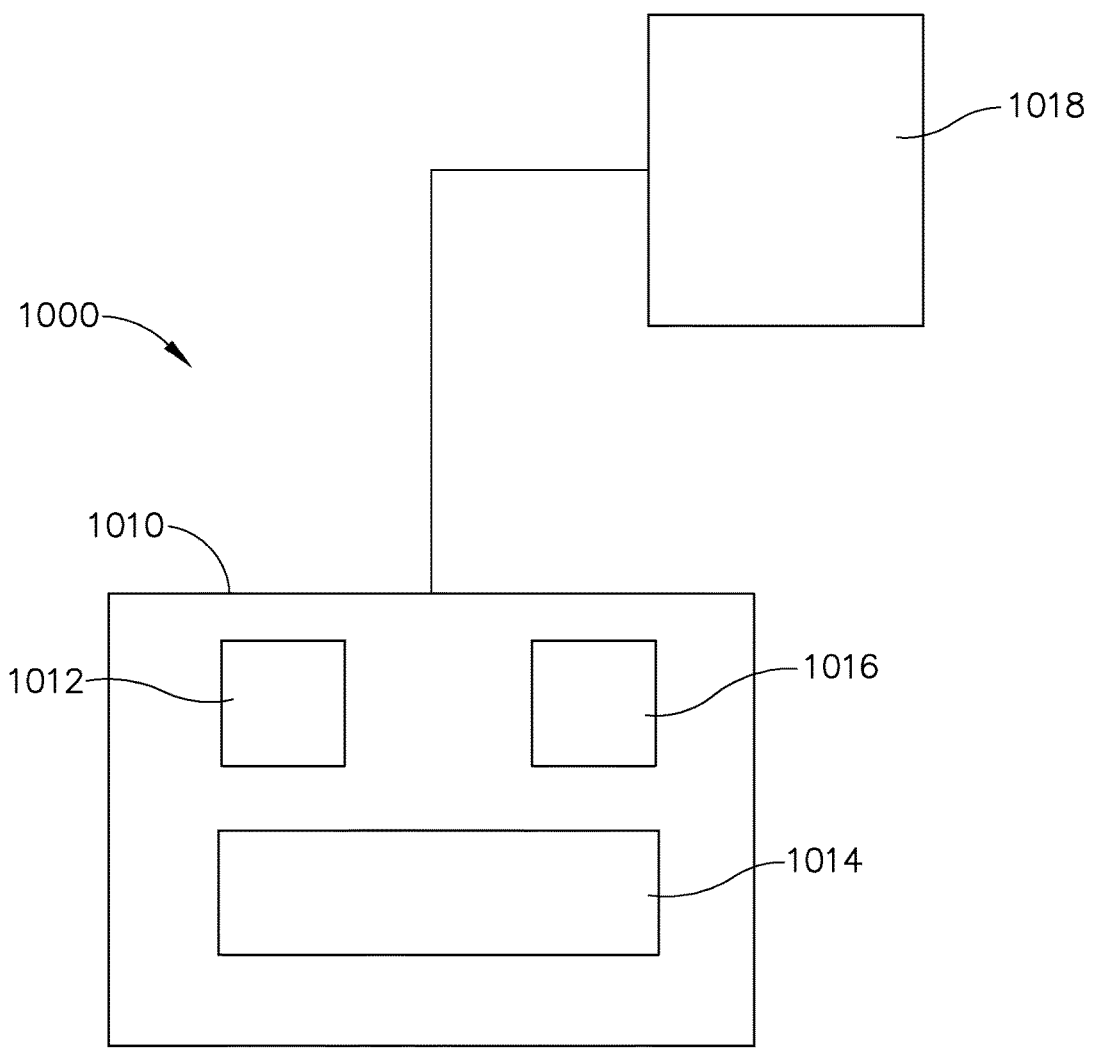
FIG. 31 depicts a schematic of an exemplary tissue sample imaging system.

After a tissue sample is collected by device (10), it may be desirable to image such tissue samples. FIG. 31 shows an exemplary imaging system (1000) that may be used to provide imaging of such tissue samples. Imaging system (1000) comprises an imaging control module (1010) coupled with a display (1018). Imaging control module (1010) includes a slot (1014) configured to receive the tissue samples collected by device (10). In some versions, slot (1014) directly insertingly receives tissue sample trays (330, 350, 1350) or manifold (310). In some other versions, slot (1014) includes a drawer or tray that slides into and out of imaging control module (1010), such that tissue sample trays (330, 350, 1350) or manifold (310) may be placed in the drawer or on the tray, with the drawer or tray then retracting back into imaging control module (1010) for imaging the tissue samples. Imaging control module (1010) further comprises an imaging device (1012) and a data processor (1016).

Imaging device (1012) may be configured to perform x-ray imaging of the tissue samples using an x-ray source (not shown) to emit x-rays, and an x-ray imaging sensor (not shown). In particular, the source may be mounted to an upper portion of the imaging control module (1010) and may radiate electromagnetic radiation in the form of x-rays towards tissue samples in tissue sample receiving trays (330) loaded into slot (1014). The radiation may then pass through the tissue sample at an angle approximately perpendicular to the longitudinal axis of each tissue sample contained in the tissue sample trays (330). The radiation may then strike the x-ray imaging sensor mounted to the bottom of imaging control module (1010), thereby providing an image of each tissue sample. Although the present example may use x-ray imaging, it should be understood that other imaging methods may be used such as Tomosynthesis, magnetic resonance, Positron Emission Tomography, etc. Moreover, the source and the x-ray imaging sensor may be oriented at different angles relative to each tissue sample contained in tissue sample trays (330) (e.g., source and x-ray imaging sensor mounted to opposing sidewalls of imaging control module (1010)). The images are then processed by data processor (1016) and communicated to display (1018). Display (1018) then provides an image of the tissue samples to a user for analyzing. In some versions, imaging system (1000) may comprise a CoreVision Specimen Radiography System manufactured by Faxitron of Tucson, Az, although any other imaging system (1000) may be used as will be apparent to those of ordinary skill in the art in view of the teachings herein.

A. Exemplary Tissue Sample Tray Containers

As noted above, slot (1014) of imaging system (1000) may receive tissue sample trays (330, 350, 1330) to image the tissue samples within trays (330, 350, 1330). Trays (330, 350, 1330) may thereby be removed from manifold (310) and placed within a container that is received by slot (1014). Below are merely illustrative examples of tissue sample tray containers that may be used with an imaging system (1000). It should be understood that any of the containers described herein may be configured to receive formalin or a similar liquid. It should also be understood that such liquid may be readily contained in a manner that avoids contact between the liquid and any component of imaging system. By way of example only, any of the containers herein may be provided with formalin or a similar liquid before a tissue sample tray (330, 350, 1330) is added. In some other versions, a container as described herein includes a port that allows the addition of formalin or a similar liquid into the container before or after a tissue sample tray (330, 350, 1330) is added to the container. Various other suitable ways in which formalin or a similar liquid may be used in conjunction with a container as described herein will be apparent to those of ordinary skill in the art in view of the teachings herein.

Figure 32A:
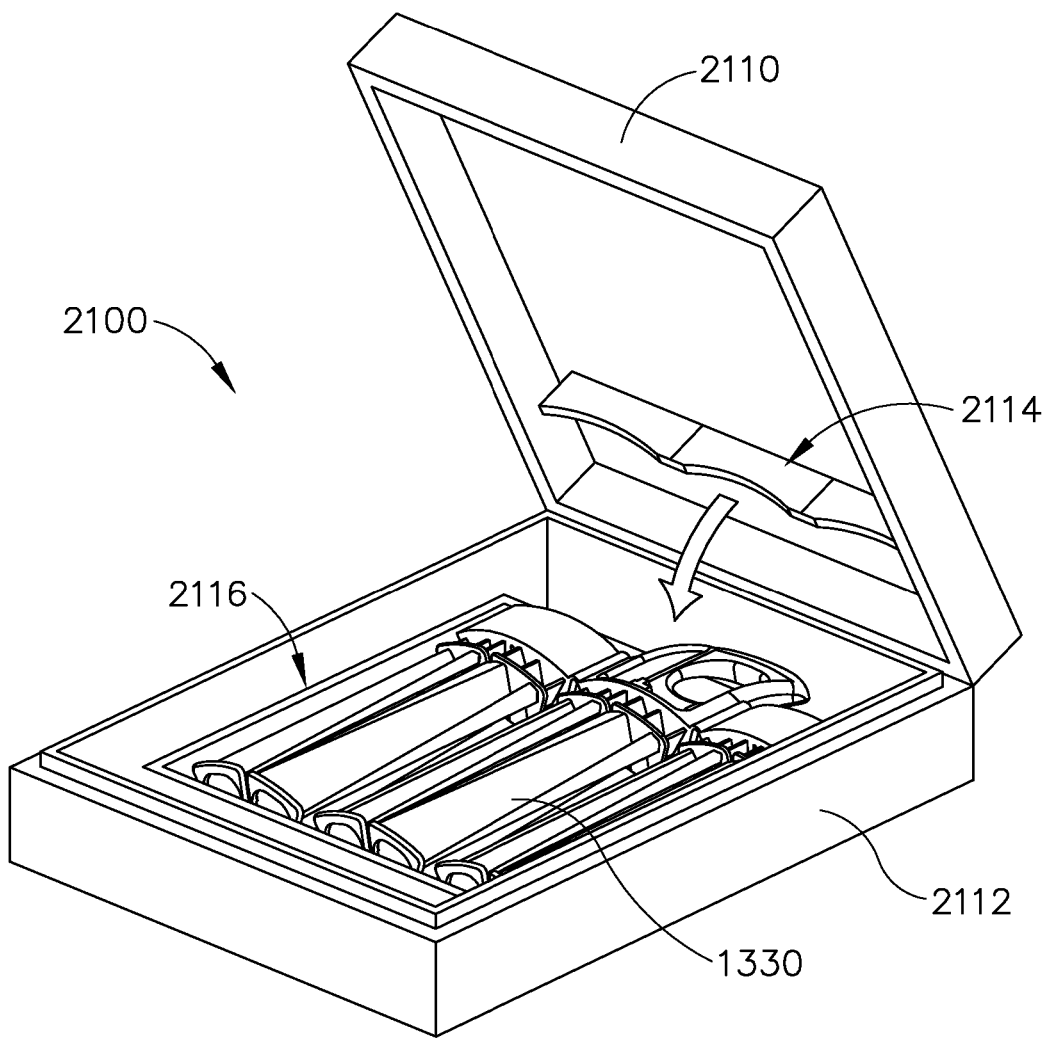
FIG. 32A depicts a perspective view of an exemplary tissue sample tray container, holding the tissue sample tray of FIG. 22 in an open position.
Figure 32B:
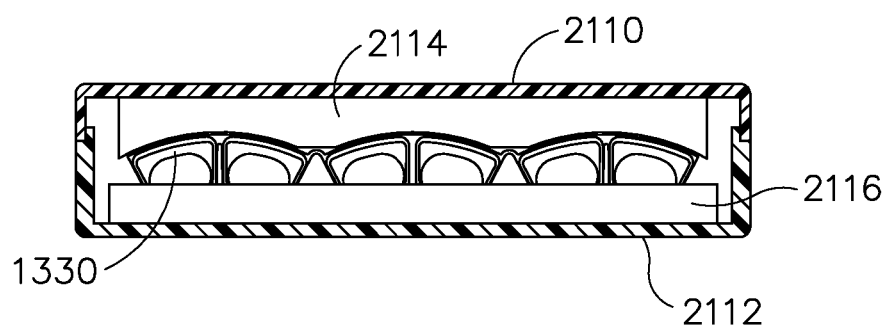
FIG. 32B depicts a front view of the container of FIG. 32A in a closed position.

FIGS. 32A-32B show an exemplary tissue sample tray container (2100). Container (2100) comprises a base (2112) and a cover (2110). In the present example, base (2112) includes a guide (2116) with walls extending from the bottom surface of base (2112) that are sized to receive tray (1330) in a flattened configuration. Cover (2110) is coupled with base (2112) such that cover (2110) is pivotable relative to base (2112). Accordingly, cover (2110) may be opened relative to base (2112) to allow base (2112) to receive tray (1330), as shown in FIG. 32A, and cover (2110) may then be closed relative to base (2112) to enclose tray (1330) within container (2100) for imaging, as shown in FIG. 32B. Alternatively, cover (2110) may be decoupled from base (2112) to insert tray (1330) within base (2112). Cover (2110) comprises a tab (2114) extending within container (2100). As shown in FIG. 32B, tab (2114) is configured to engage tray (1330) when cover (2110) is closed relative to base (2112). Tab (2114) thereby maintains tray (1330) in the flattened configuration for imaging. In the present example, the end portion of tab (2114) has an arcuate configuration to align with strips (1350) of tissue sample tray (1330). Cover (2110) and/or base (2112) may further be made of a transparent material to allow for imaging of the tissue samples within tray (1330).

Accordingly, tray (1330) is inserted within container (2100) when container (2100) is in the open configuration, as shown in FIG. 32A. Tray (1330) is in the flattened configuration and is maintained within guide (2116) of base (2112). Cover (2110) is then pivoted relative to base (2112) to close container (2100), as shown in FIG. 32B. Tab (2114) thereby engages tray (1330) to maintain tray (1330) in the flattened configuration. Container (2100) may be inserted within slot (1014) of imaging system (1000) such that the tissue samples within tray (1330) may be imaged by imaging system (1000).

Figure 33A:
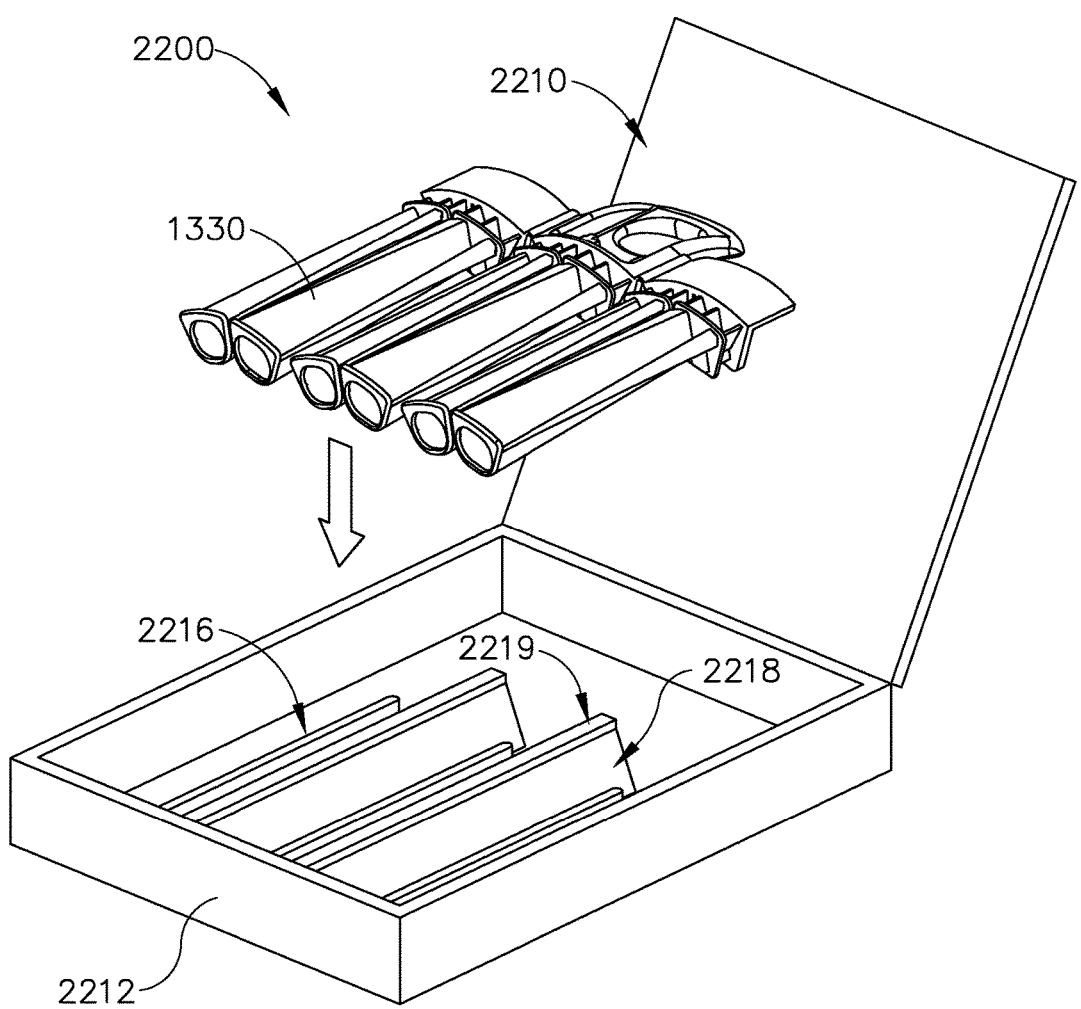
FIG. 33A depicts a perspective view of another exemplary tissue sample tray container, holding the tissue sample tray of FIG. 22 in an open position.
Figure 33B:
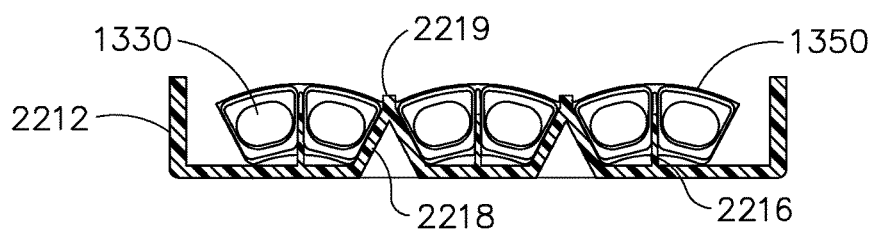
FIG. 33B depicts a front view of the container of FIG. 33A in a closed position.

FIGS. 33A-33B show another exemplary tissue sample tray container (2200), similar to container (2100), except that container (2200) comprises dividing tabs (2216, 2218) instead of guide (2116). Tabs (2216, 2218) extend upwardly from the bottom surface of base (2214). A first tab (2216) is configured as a substantially vertical wall that is positioned between strips (1350) of tray (1330) when tray (1330) is inserted within container (2200). A second tab (2218) includes walls that extend outwardly to align with strips (1350) of tray (1330) between living hinges (1336). Tabs (2216, 2218) thereby maintain tray (1330) in a flattened configuration, as shown in FIG. 33B. Second tabs (2218) further comprises locking tabs (2219) extending outwardly from second tabs (2218). Locking tabs (2219) are configured extend over a portion of tray (1330) when tray (1330) is inserted within container (2200) to lock tray (1330) within container (2200). Locking tabs (2219) may be configured such that tray (1330) is snap fit between tabs (2216, 2218). Grip (1332) of tray (1330) may thus be used insert and/or remove tray (1330) from container (2200). Other suitable locking configurations will be apparent to one with ordinary skill in the art in view of the teachings herein.

Accordingly, tray (1330) is inserted within container (2200) when container (2200) is in the open configuration, as shown in FIG. 33A. Tray (1330) is in the flattened configuration and positioned between tabs (2216, 2218). As shown in FIG. 33B, first tabs (2216) are positioned between strips (1350) of tray (1330) and second tabs (2218) are positioned between living hinges (1336) of tray (1330) to maintain tray (1330) in the flattened configuration. Locking tabs (2219) extend over a portion of tray (1330) to lock tray (1330) within container (2200). Cover (2210) is then pivoted relative to base (2212) to close container (2200). Container (2200) may be inserted within slot (1014) of imaging system (1000) such that the tissue samples within tray (1330) may be imaged by imaging system (1000).

Figure 34A:
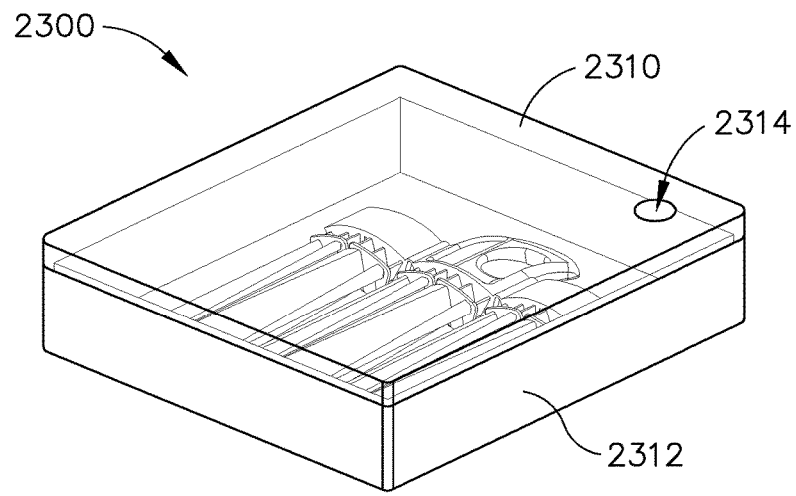
FIG. 34A depicts a perspective view of another exemplary tissue sample tray container, holding the tissue sample tray of FIG. 22 in a closed position.
Figure 34B:
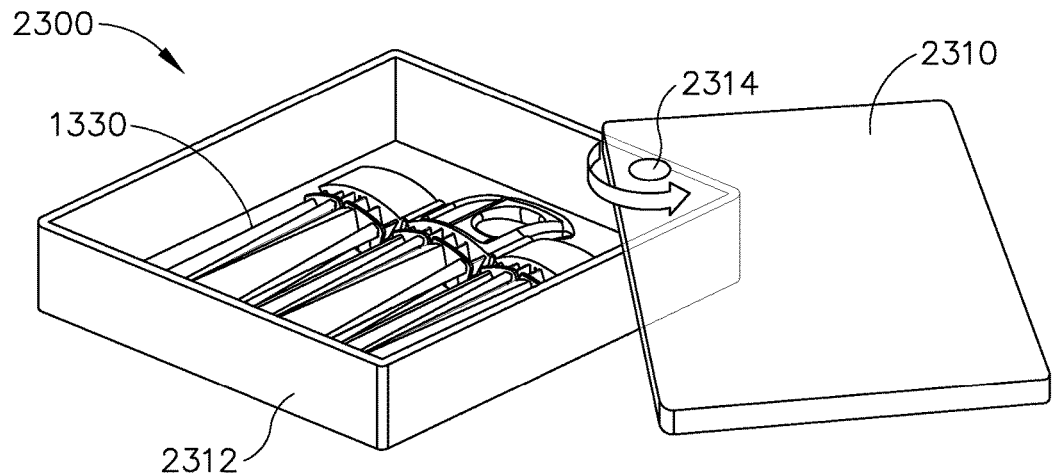
FIG. 34B depicts a perspective view of the container of FIG. 34A in an open position.

FIGS. 34A-34B show another exemplary tissue sample tray container (2300), similar to container (2100), except that container (2300) comprises a rotatable cover (2310). Cover (2310) is coupled to base (2312) via a pin (2314). In the present example, pin (2314) is positioned in a corner portion of container (2300) such that cover (2310) may be rotated relative to base (2312) to substantially uncover base (2312). As shown in FIG. 34A, cover (2310) is in a closed position such that cover (2310) is positioned over base (2312). Cover (2310) is then rotated relative to base (2312) via pin (2314) to uncover base (2312), as shown in FIG. 34B. A tissue sample tray (1330) is then inserted within base (2312) of container (2300) in the flattened configuration. Cover (2310) is then rotated back to the closed position in FIG. 34A. Cover (2310) may continue to rotate in the same direction such that cover (2310) rotates 360 degrees to close container (2300), or cover (2310) may rotate in the opposing direction to return to the closed position. Once cover (2310) is in the closed position, container (2300) may be inserted within slot (1014) of imaging system (1000) such that the tissue samples within tray (1330) may be imaged.

Figure 35:
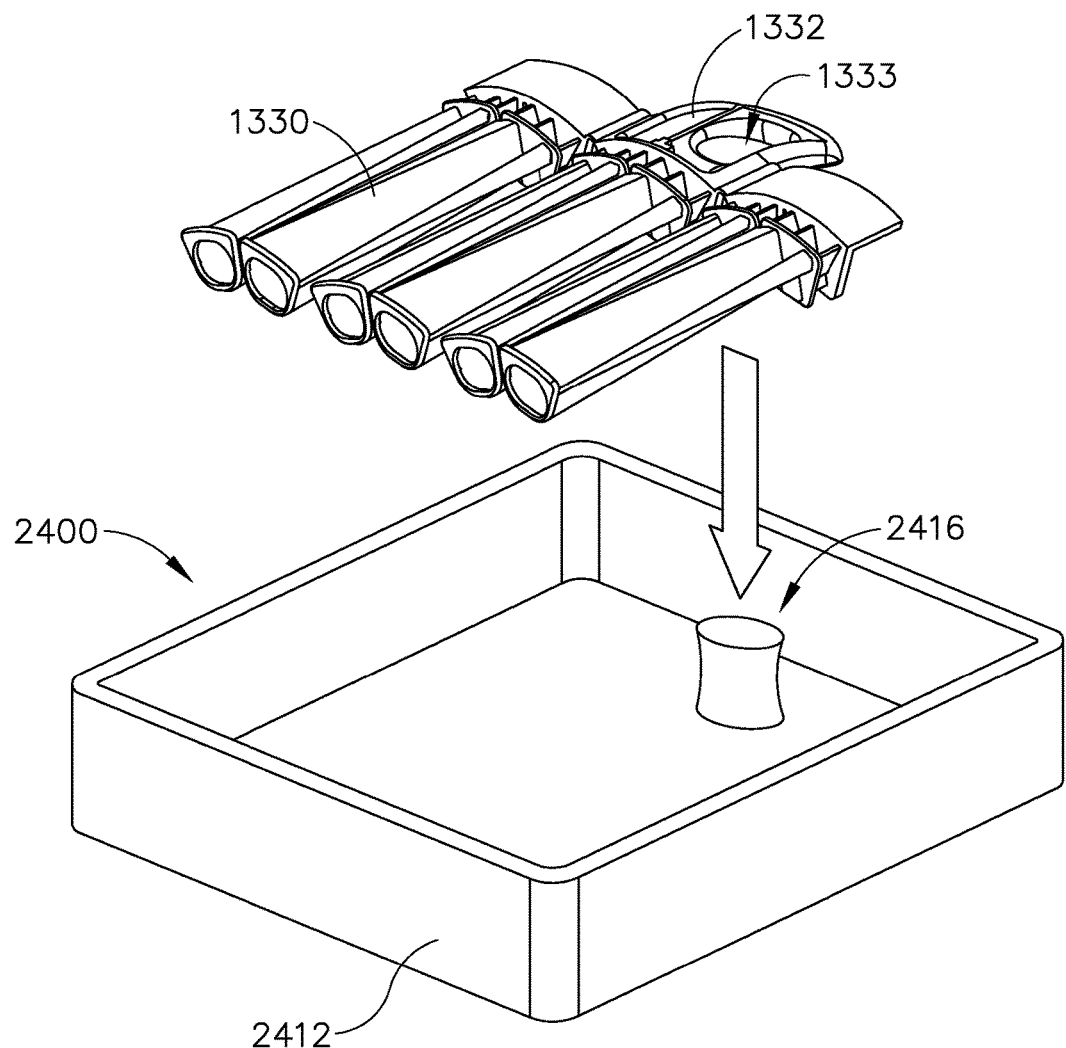
FIG. 35 depicts a perspective view of another exemplary tissue sample tray container, receiving the tissue sample tray of FIG. 22.

In some versions, tissue sample tray container (2400) comprises a protrusion (2416) to receive tray (1330), as shown in FIG. 35. Container (2400) is similar to container (2100), except that container (2400) comprises protrusion (2416) extending upwardly from the bottom surface of base (2412). Grip (1332) of tray (1330) defines an opening (1333) to receive protrusion (2416) of base (2412). Protrusion (2416) thereby maintains the position of tray (1330) within container (2400). Protrusion (2416) may be configured to snap fit with opening (1333) of tray (1330) to lock tray (1330) within base (2412), but other locking configurations may be used. In the present example, tray (1330) is inserted within container (2400) in the flattened configuration, as shown in FIG. 35. Protrusion (2416) inserts within opening (1333) of tray (1330) to maintain tray (1330) within base (2412). Container (2412) may then be inserted within slot (1014) of imaging system (1000) to image the tissue samples within tray (1330). In the present example, container (2400) does not include a cover, which is merely optional.

Figure 36A:
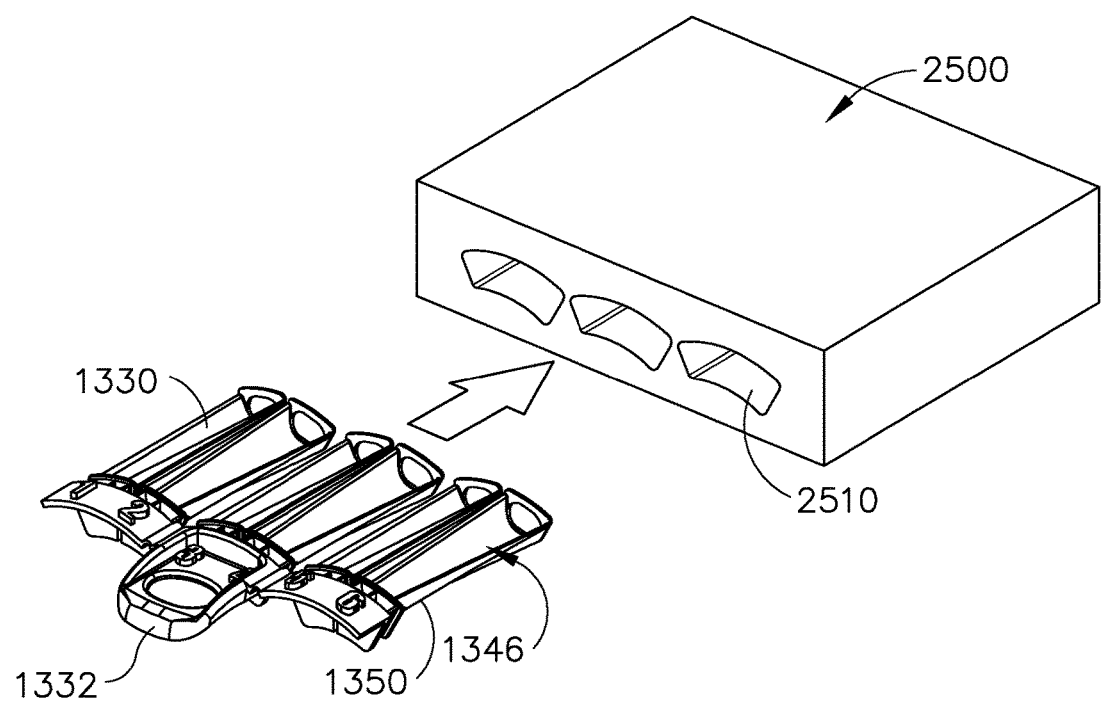
FIG. 36A depicts a perspective view of another exemplary tissue sample tray container, receiving the tissue sample tray of FIG. 22.
Figure 36B:
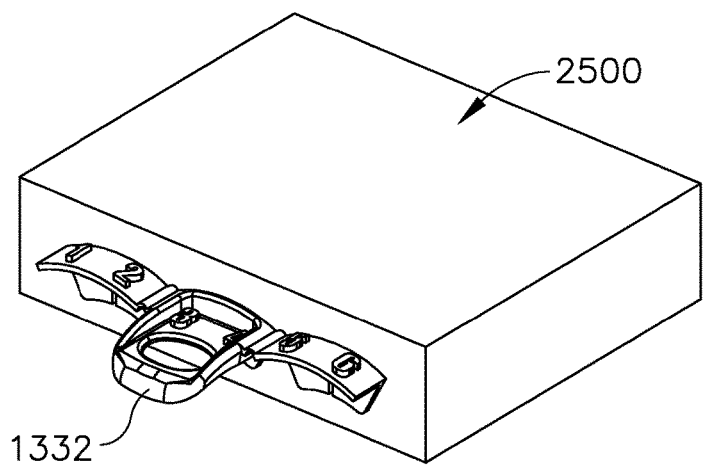
FIG. 36B depicts a perspective view of the container of FIG. 36A, with the tissue sample tray of FIG. 22 inserted within the container.
Figure 37:
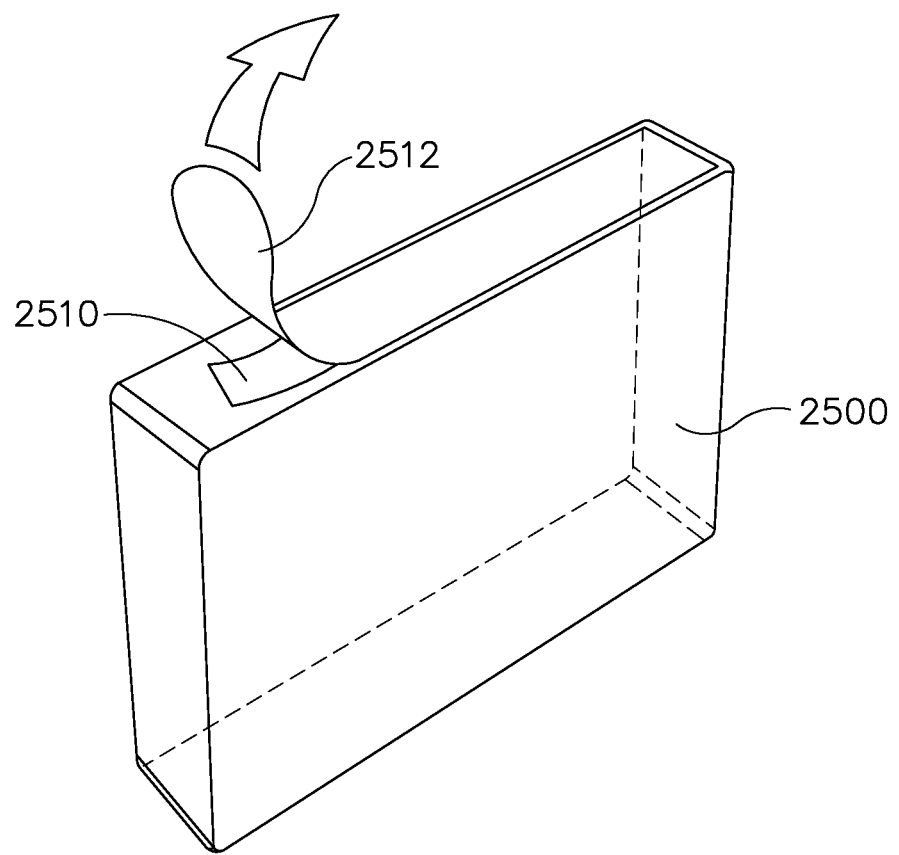
FIG. 37 depicts a perspective view of the container of FIG. 36A with a peelable closure.

In some versions, a tissue sample tray container (2500) contains slots (2510) to receive strips (1350) of tray (1330), as shown in FIGS. 36A-36B. Container (2500) is similar to container (2100), except that container (2500) is a unitary piece with a hollow interior and comprises a plurality of slots (2510) positioned on a side surface of container (2500). Slots (2510) are sized to receive each strip (1350) of tray (1330) positioned between living hinges (1336). Alternatively, slots (2510) may be sized to receive each strip (1350) individually, or container (2500) may have one slot (2510) to receive all of strips (1350) in slot (2510). Tray (1330) is inserted within container (2500) until proximal wall (1334) of tray (1330) contacts the side surface of container (2500). Accordingly, tray (1330) is inserted within container (2500), as shown in FIGS. 36A-36B. Container (2500) is then placed within slot (1014) of imaging system (1000) to image the tissue samples within tray (1330). In the present example, container (2500) does not have a cover. However, in some versions, a top surface or a side surface of container (2500) may pivot relative to container (2500) such that the top surface or side surface of container (2500) opens to allow access to tray (1330) when tray (1330) is inserted within container (2500). In some other versions, container (2500) comprises a peelable label (2512) placed over slots (2510), as shown in FIG. 37. Label (2512) covers slots (2510) and is peeled away from container (2500) to uncover slots (2510) when container (2500) is ready for use. Container (2500) may also have a labeling surface such that patient information is provided on the labeling surface of container (2500).

Figure 38A:
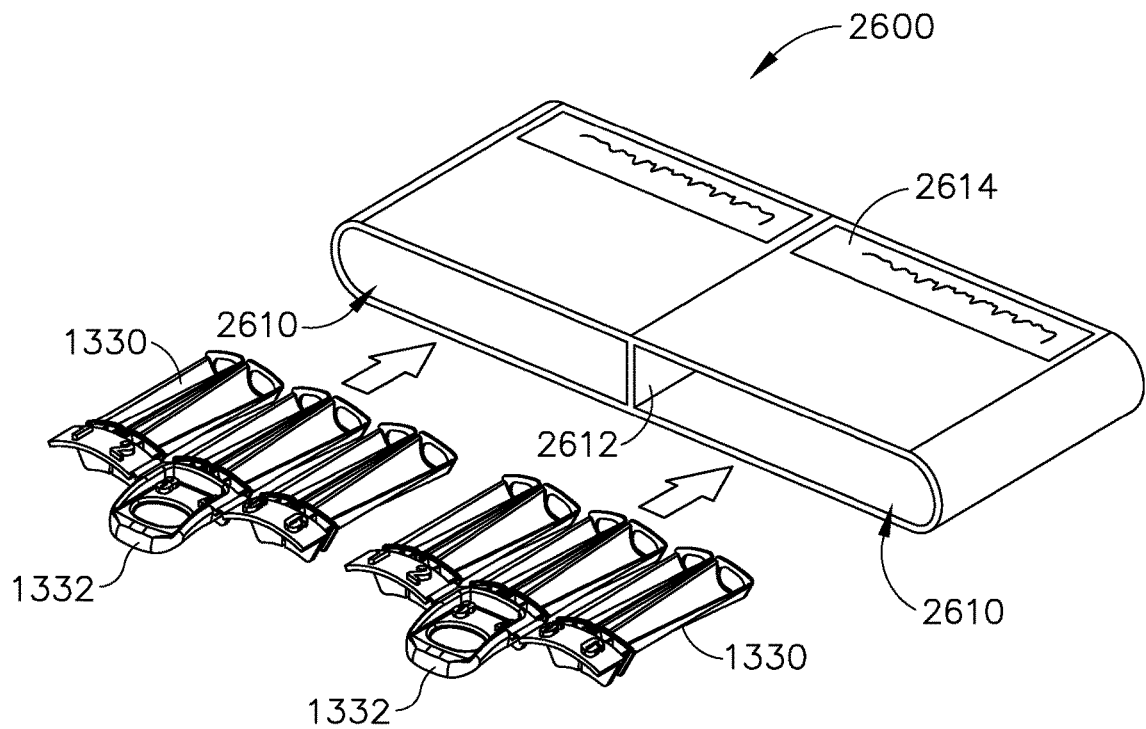
FIG. 38A depicts a perspective view of another exemplary tissue sample tray container, receiving the tissue sample tray of FIG. 22.
Figure 38B:
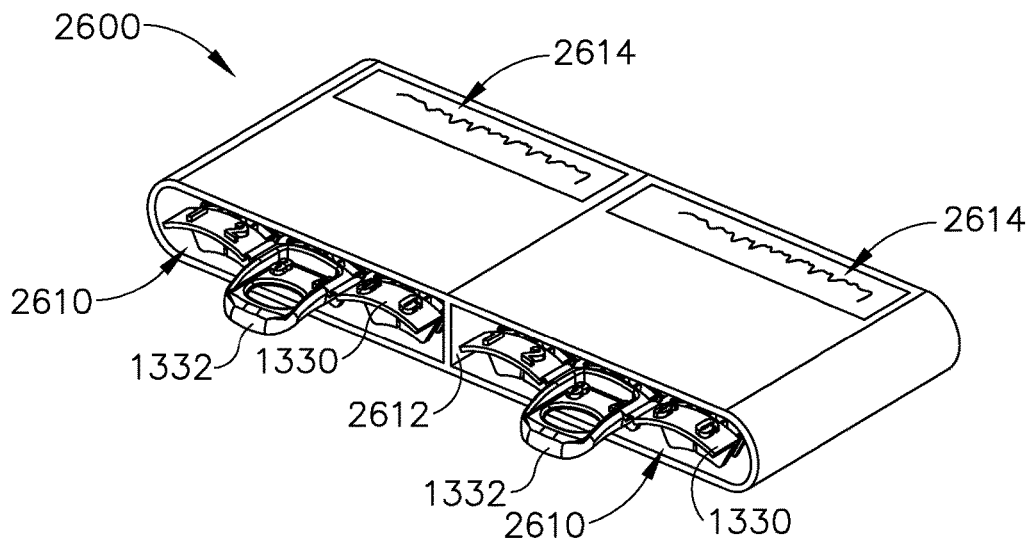
FIG. 38B depicts a perspective view of the container of FIG. 38A, with the tissue sample tray of FIG. 22 inserted within the container.

In some versions, a tissue sample tray container (2600) is configured to receive a plurality of tissue sample trays (1330), as shown in FIGS. 38A-38B. Container (2600) is similar to container (2100), except that container (2600) comprises a pair of openings (2610) that are each configured to receive a tray (1330). In the present example, openings (2610) are positioned on a side surface of container (2600) such that trays (1330) are positioned side by side within container (2600), but openings (2610) may also be configured on a top surface of container (2600). A wall (2612) extends between openings (2610) to separate trays (1330). Container (2600) further comprises a labeling surface (2614) for each tray (1330) such that patient information may be placed on labeling surfaces (2614). Accordingly, a tray (1330) is inserted distally within each opening (2610), as shown in FIGS. 38A-38B. Container (2600) is then placed within slot (1014) of imaging system (1000) to image the tissue samples within trays (1330). In the present example, grips (1332) of trays (1330) extend outwardly from openings (2610) when trays (1330) are inserted within container (2600), as shown in FIG. 38B. Alternatively, container (2600) may be configured to receive trays (1330) such that trays (1330) are fully positioned within container (2600). Container (2600) of the present example also does not have a cover. In some versions, a cover is coupled with container (2600) to selectively cover openings (2610). Although two openings (2610) are shown in the present example, container (2600) may comprise any other suitable number of openings (2610).

Figure 39:
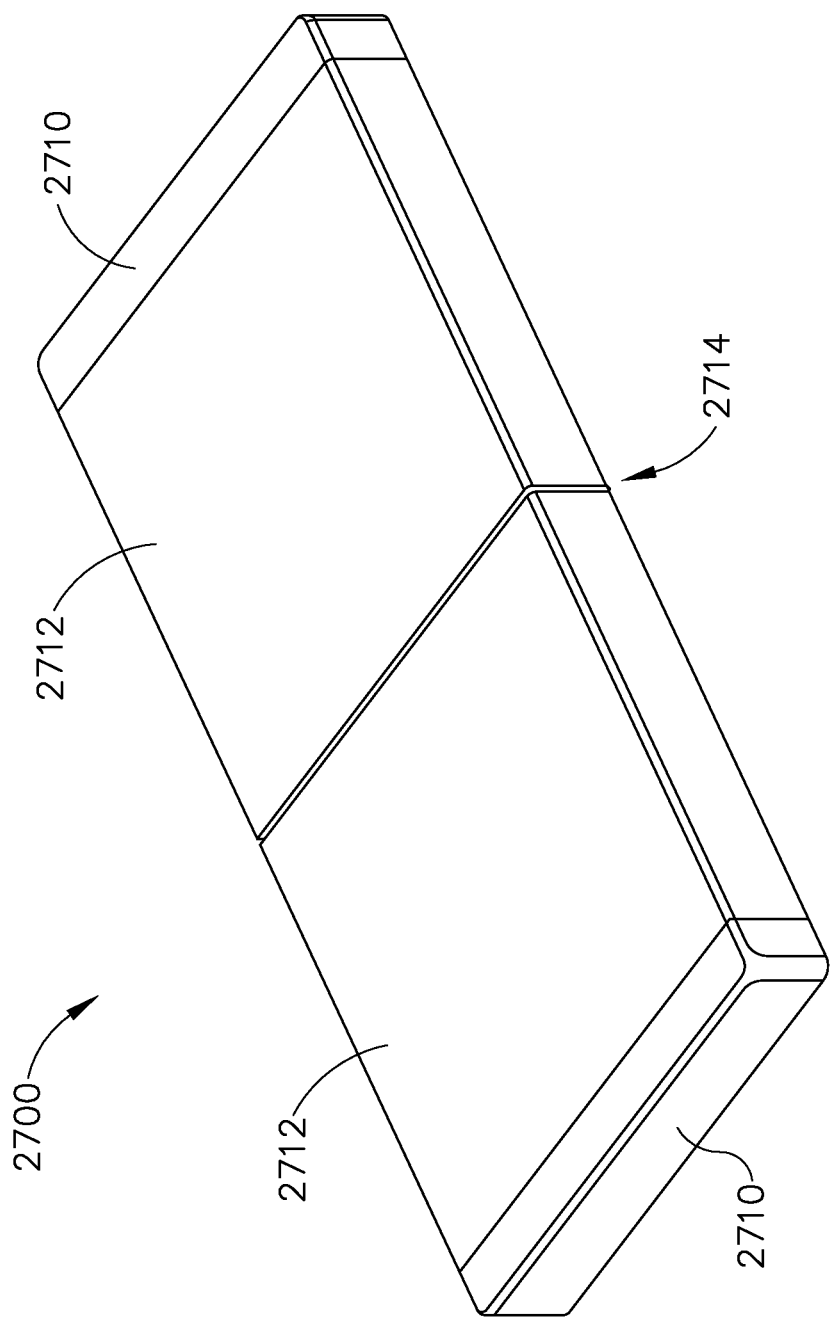
FIG. 39 depicts a perspective view of another exemplary tissue sample tray container to hold the tissue sample tray of FIG. 22.

FIG. 39 shows another exemplary tissue sample tray container (2700), similar to container (2600), except that container (2700) comprises two chambers (2712) that are pivotable relative to each other to allow container (2700) to fold in half. Container (2700) comprises two chambers (2712), positioned end to end, that are each configured to receive a tray (1330). Chambers (2712) are coupled by a living hinge (2714) such that chambers (2712) are pivotable relative to each other. Container (2700) further comprises a cover (2710) positioned over each chamber (2712), although covers (2710) are merely optional. Covers (2710) may be removable from chambers (2712) or covers (2710) may be pivotable relative to chambers (2712) to selectively open and close chambers (2710). Although two chambers (2712) are shown in FIG. 39, any other suitable number of chambers (2712) may be used.

Figure 40A:
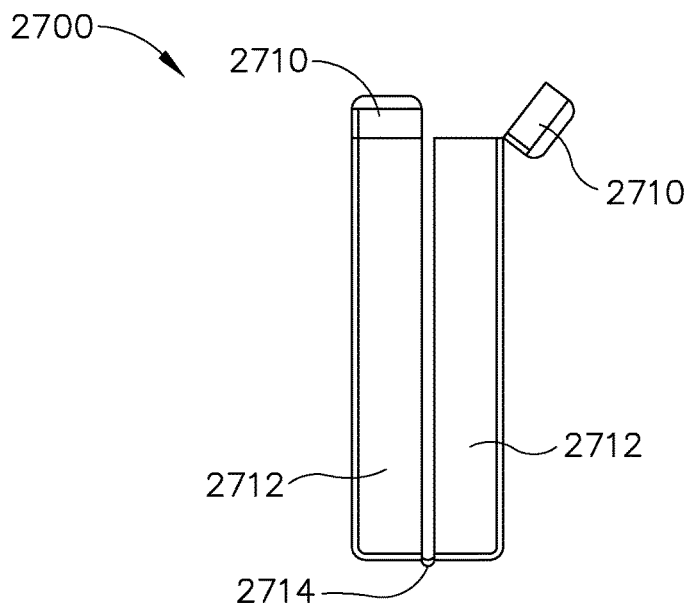
FIG. 40A depicts a side elevational view of the container of FIG. 39 in a first position.
Figure 40B:
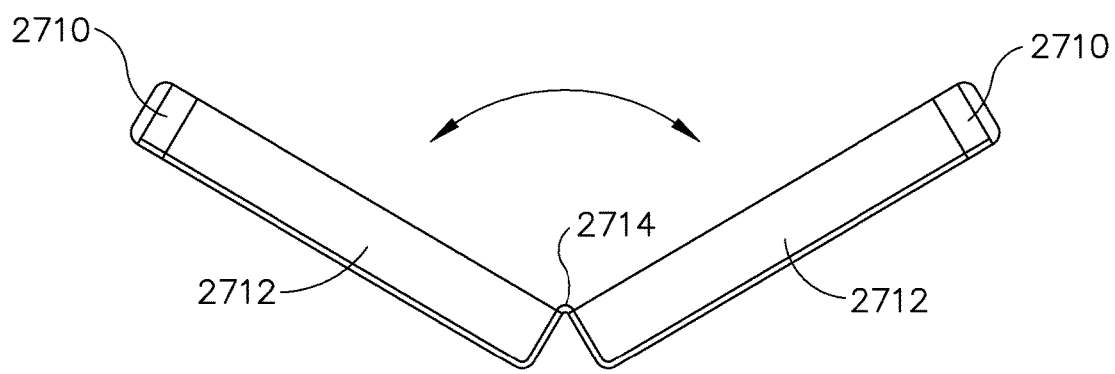
FIG. 40B depicts a side elevational view of the container of FIG. 39 in a second position.
Figure 40C:
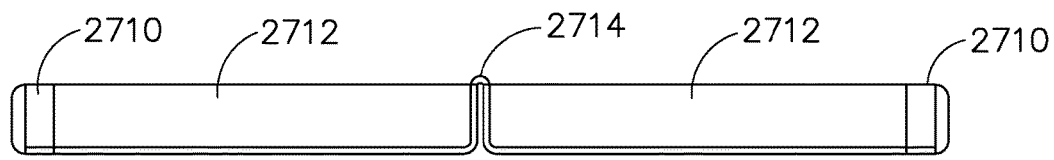
FIG. 40C depicts a side elevational view of the container of FIG. 39 in a third position.

As shown in FIG. 40A, chambers (2712) are in a folded configuration. Chambers (2712) may be configured to lock in this position via resilient tabs or other suitable locking methods apparent to one with ordinary skill in the art in view of the teachings herein. Covers (2710) are pivoted open relative to chambers (2712) to allow a tray (1330) to be inserted within each chamber (2710). Once trays (1330) are inserted within chambers (2712), covers (2710) are then pivoted to close chambers (2712). Chambers (2712) are then pivoted away from each other to an unfolded position via living hinge (2714), as shown in FIG. 40B. Container (2700) is then in a flattened position, as shown in FIG. 40C. Container (2700) is then placed within slot (1014) of imaging system (1000) to image the tissue samples within trays (1330).

Figure 41A:
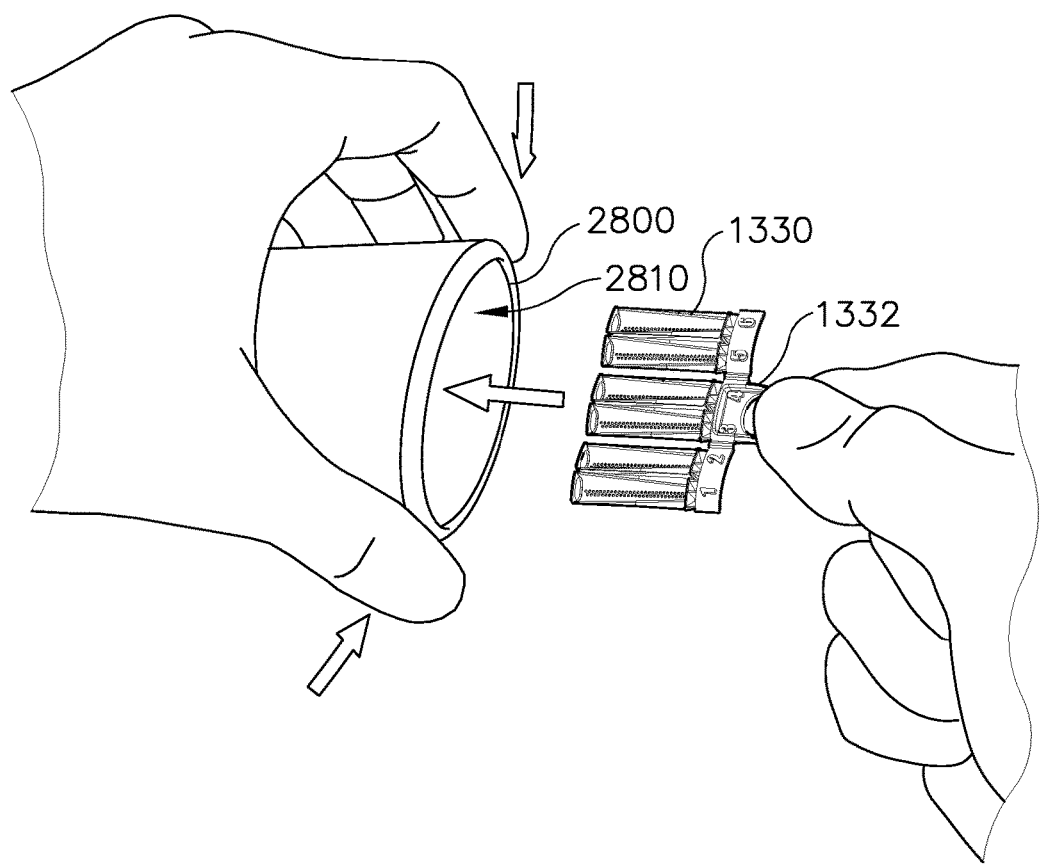
FIG. 41A depicts a perspective view of another exemplary tissue sample tray container, receiving the tissue sample tray of FIG. 22.
Figure 41B:
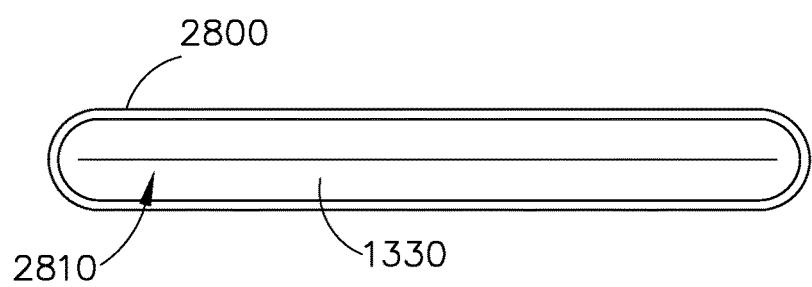
FIG. 41B depicts a front view of the container of FIG. 41A, with the tissue sample tray of FIG. 22 inserted within the container.

FIGS. 41A-41B show another exemplary tissue sample tray container (2800), similar to container (2100), except that container (2800) is resiliently biased to a flattened configuration. Container (2800) comprises an opening (2810) on a side surface of container (2800). Container (2800) is flexible and is biased to the flattened position shown in FIG. 41B. Accordingly, a user may squeeze container (2800), as shown in FIG. 41A, to widen opening (2810) of container (2800). The user may then insert a tissue sample tray (1330) within opening (2810) of container (2800) while tray (1300) is in the arcuate position. The user may then release container (2800) to allow container (2800) to bias back to the flattened position, shown in FIG. 41B. When container (2800) returns to the flattened position, container (2800) thereby flattens tray (1330) within container (2800). Container (2800) is then inserted within slot (1014) of imaging system (1000) to image the tissue samples within tray (1330).

Figure 42C:
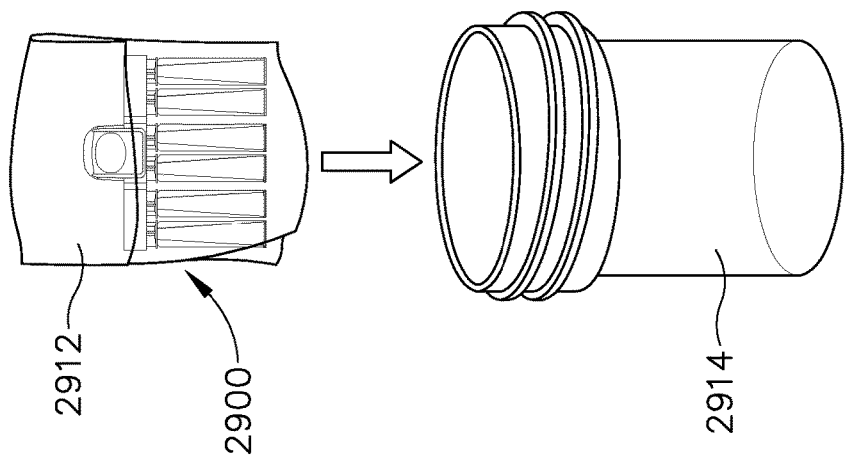
FIG. 42C depicts a perspective view of the container of FIG. 42A, with the container being inserted into a formalin container.
Figure 42A:
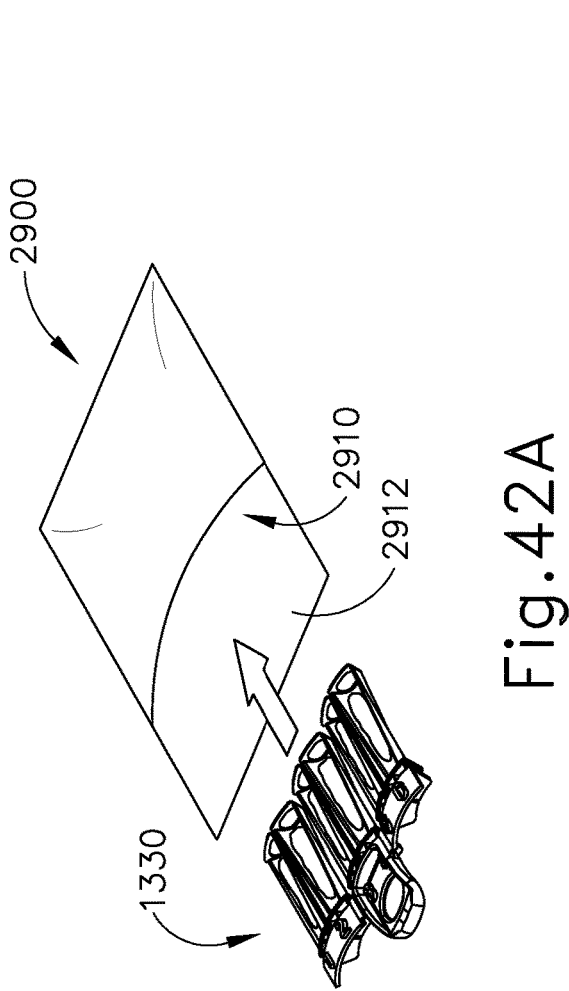
FIG. 42A depicts a perspective view of another exemplary tissue sample tray container, receiving the tissue sample tray of FIG. 22.
Figure 42B:
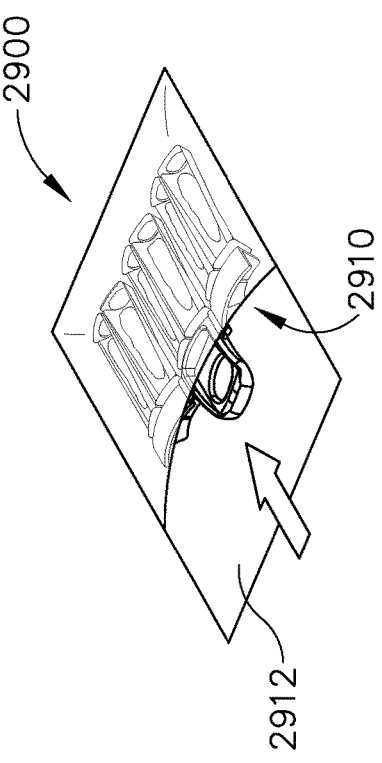
FIG. 42B depicts a perspective view of the container of FIG. 42A, with the tissue sample tray of FIG. 22 inserted within the container.

FIGS. 42A-42C show another exemplary tissue tray container (2900), similar to container (2800), except that container (2900) is a flexible pouch without a resilient bias. As will be described in greater detail below, container (2900) is sized for insertion into a formalin container (2914). Container (2900) comprises an opening (2910) on a side surface of container (2900). Opening (2910) has a flap (2912) which extends from opening (2910). Container (2900) is comprised of a radiotranslucent woven synthetic material suitable to be submerged in formalin without degrading or leaching in to a tissue sample held within container (2900). By way of example only, the woven material of container (2900) may be a nylon fiber having a filter rating of 150 microns and an open area of 35%, designated as "8-TT" manufactured by SAATITech of Somers, N.Y. Of course, other suitable materials may be used such as polyester, other forms of nylon, or any other suitable material as may be apparent to those of ordinary skill in the art in view of the teachings herein. Moreover, the fiber weave may have a filter rating ranging between approximately 125-165 microns and an open area ranging between approximately 25 to 45% or any other values as may be apparent to those of ordinary skill in the art in view of the teachings here.

Container (2900) is flexible such that it may be opened by a user to widen opening (2910). Accordingly, a user may open container (2900) and insert a tissue sample tray (1330) through opening (2910) and into container (2900). Once tray (1330) is inserted into container (2900), a user may fold flap (2912) to enclose tray (1330) within container (2900), as can be seen in FIG. 42B. The user may then insert container (2900) into formalin container (2914), as shown in FIG. 42C. Container (2900) may allow formalin inside formalin container (2914) to pass through to thereby soak the tissue samples. Thus, container (2900) is permeable or semi-permeable. Formalin container (2914) may then be imaged with an imaging system (not shown) similar to imaging system (1000) or be stored for later examination. Of course, in other examples, container (2900) with inserted tissue sample tray (1330) may first be imaged with the imaging system and then placed in formalin container (2914) for storage. Formalin container (2914) may be comprised of any suitable material compatible with formalin such as polypropylene, polyethylene, and/or etc. It should be understood that container (2900) may relatively tight fit relative to tissue sample tray (1330), thus maintaining the tissue samples in their respective chambers in tray (1330). In other examples, container (2900) may be more or less tight relative to tissue sample tray (1330).

B. Exemplary Tissue Sample Manifolds

Instead of receiving tissue sample tray containers (2100, 2200, 2300, 2400, 2500, 2600, 2700, 2800), slot (1014) of imaging system (1000) may receive a manifold (310) to image the tissue samples within trays (330, 350, 1330). Manifold (310) is thereby inserted within imaging system (1000) with trays (330, 350, 1330) still inserted within manifold (310). Accordingly, manifold (310) may include folding features to allow manifold (310) to be flattened for insertion within imaging system (1000). Below are merely illustrative examples of tissue sample manifolds with folding features that may be used with an imaging system (1000).

Figure 43:
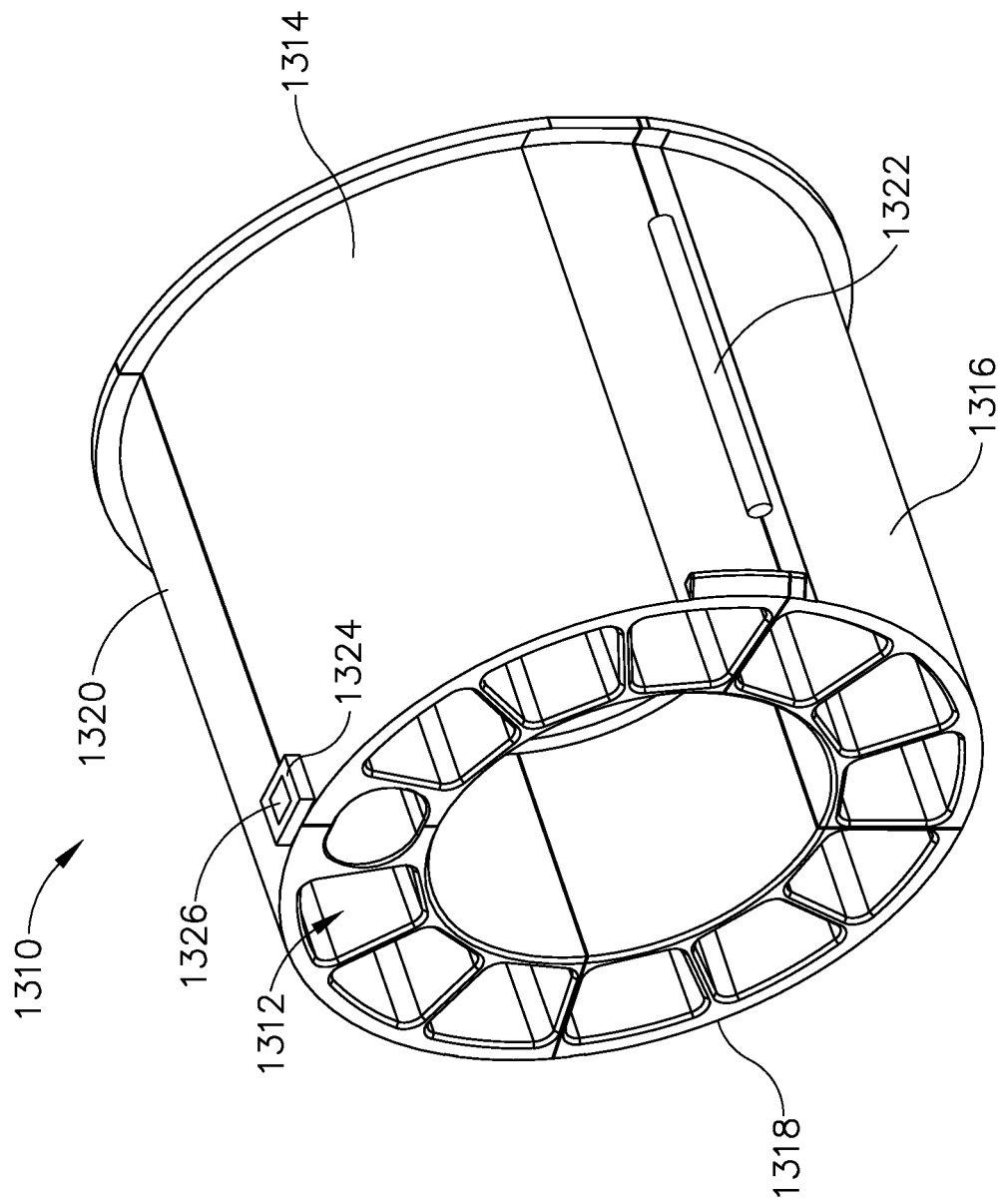
FIG. 43 depicts a perspective view of another exemplary rotatable manifold in a folded position.
Figure 44:
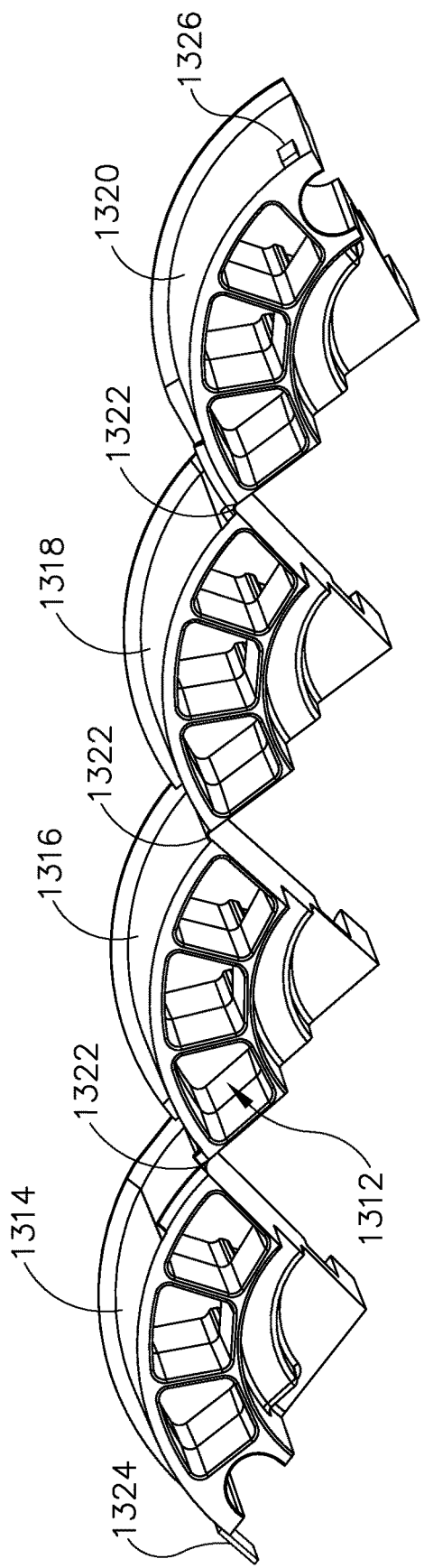
FIG. 44 depicts a perspective view of the manifold of FIG. 42 in an unfolded position.
Figure 45:
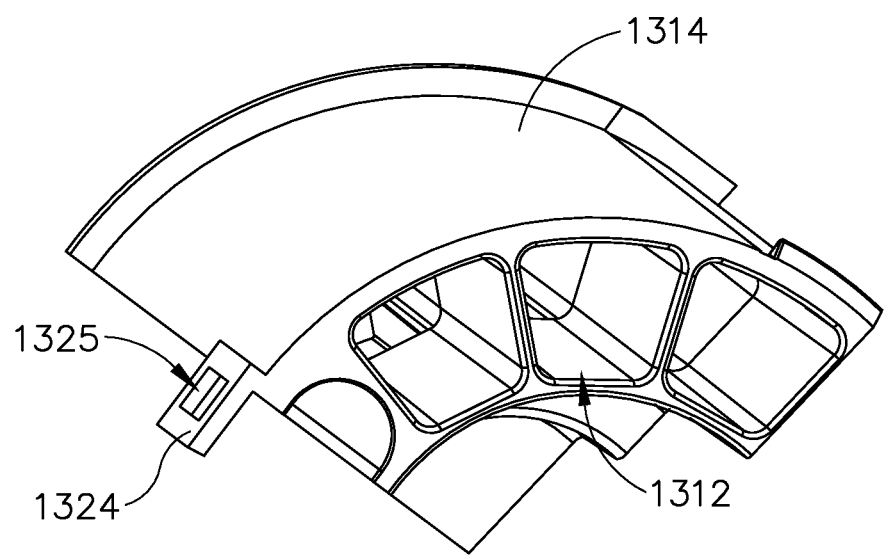
FIG. 45 depicts a perspective view of a first section of the manifold of FIG. 42.
Figure 46:
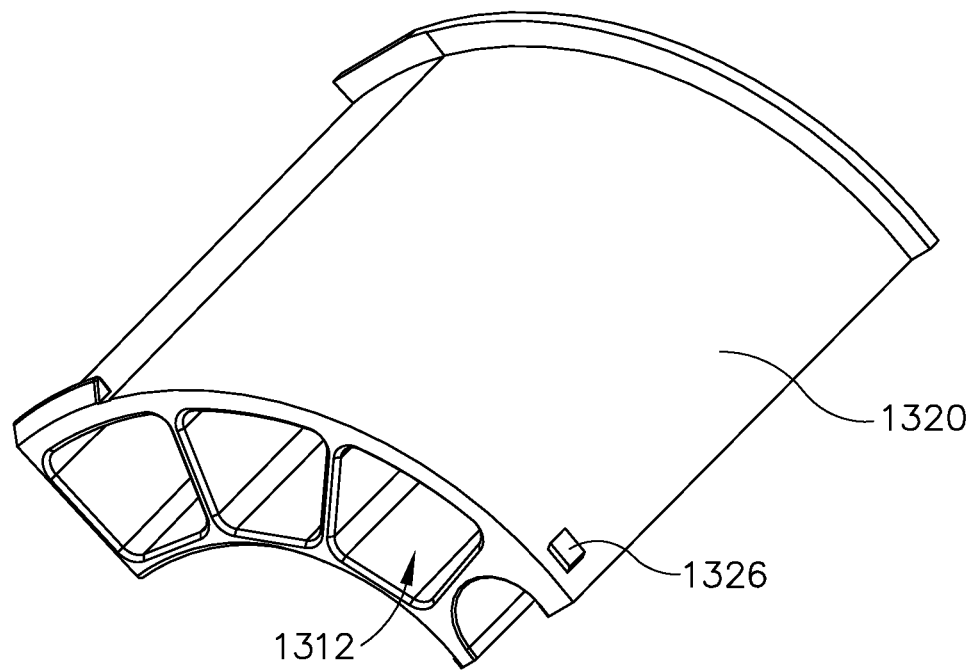
FIG. 46 depicts a perspective view of a fourth section of the manifold of FIG. 42.

FIGS. 43-46 show an exemplary manifold (1310) that is similar to manifold (310), except that manifold (1310) is comprises four folding sections (1314, 1316, 1318, 1320). Sections (1314, 1316, 1318, 1320) are coupled via living hinges (1322), as shown in FIG. 43, to allow sections (1314, 1316, 1318, 1320) to pivot relative to each other. Sections (1314, 1316, 1318, 1320) are thereby pivoted to an unfolded configuration, as shown in FIG. 44. Although the present example includes four sections (1314, 1316, 1318, 1320), any other number of sections (1314, 1316, 1318, 1320) may be used. First section (1314) comprises a tab (1324) extending from first section (1314) with an opening (1325), as shown in FIG. 45. Fourth section (1320) comprises a protrusion (1326) extending from fourth section (1320), as shown in FIG. 46. Protrusion (1326) is configured to be inserted within opening (1325) of tab (1324) to thereby lock sections (1314, 1316, 1318, 1320) in the folded configuration. Accordingly, manifold (1310) is inserted within biopsy device (10) to collect tissue samples in the folded configuration shown in FIG. 43. Once the samples are collected, manifold (1310) is removed from device (10). Tab (1324) of first section (1314) is lifted to release protrusion (1326) of fourth section (1320). Manifold (1310) is then unfolded to the flattened configuration shown in FIG. 44 and placed within slot (1014) of imaging system (1000) to image the tissue samples within manifold (1310).

Figure 47A:
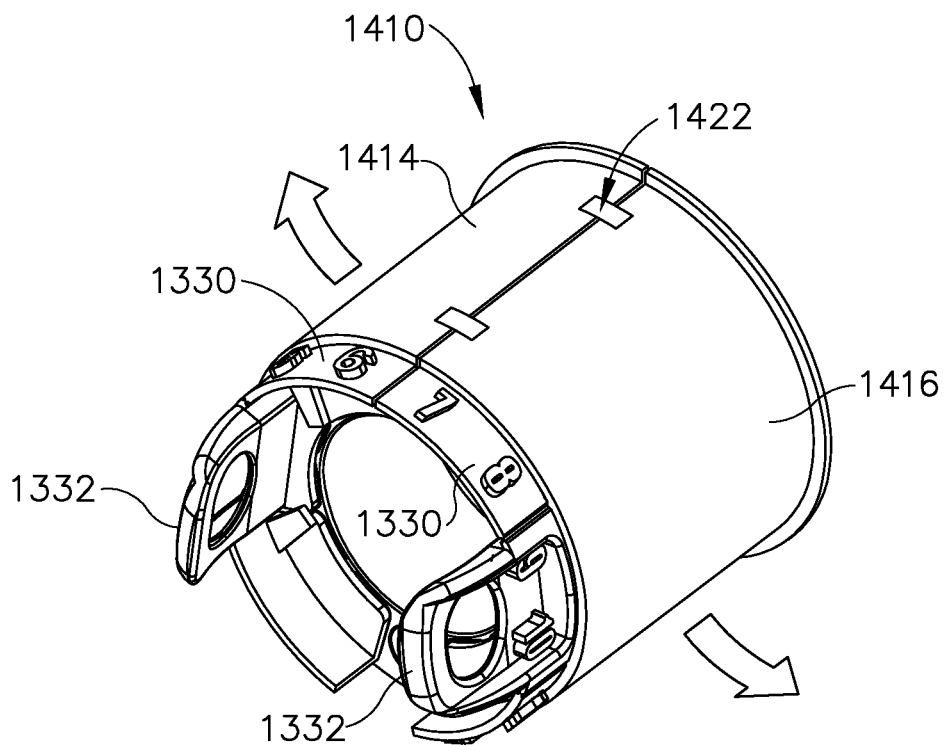
FIG. 47A depicts a perspective view of the another exemplary rotatable manifold in a folded position.
Figure 47B:
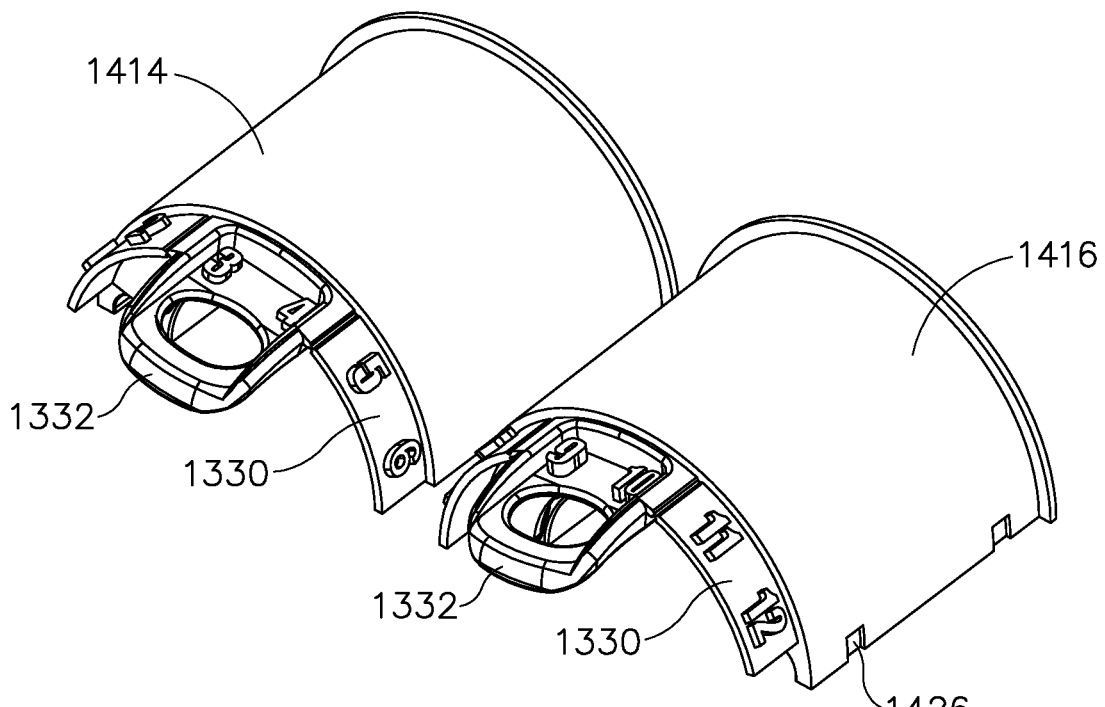
FIG. 47B depicts a perspective view of the manifold of FIG. 46A in an unfolded position.

FIGS. 47A-47B show another exemplary foldable manifold (1410). Manifold (1410) is similar to manifold (1310), except that manifold (1410) comprises two folding sections (1414, 1416). Each section (1414, 1416) is configured to hold a tray (1330). Sections (1414, 1416) are coupled via a living hinge (not shown) such that sections (1414, 1416) are pivotable relative to each other. Sections (1414, 1416) are thus positioned side by side in the unfolded configuration. First section (1414) comprises two tabs (1422) extending from first section (1414) that are configured to engage protrusions (1426) of second section (1416) to lock sections (1414, 1416) in the folded configuration. Although two tabs (1422) are shown in the present example, any other number of tabs (1422) may be used. Accordingly, manifold (1410) is inserted within biopsy device (10) to collect tissue samples in the folded configuration shown in FIG. 47A. Once the samples are collected, manifold (1410) is removed from device (10). Tab (1422) of first section (1414) is lifted to release protrusion (1426) of second section (1416). Manifold (1410) is then unfolded to the flattened configuration shown in FIG. 47B and placed within slot (1014) of imaging system (1000) to image the tissue samples within manifold (1410).

Figure 48A:
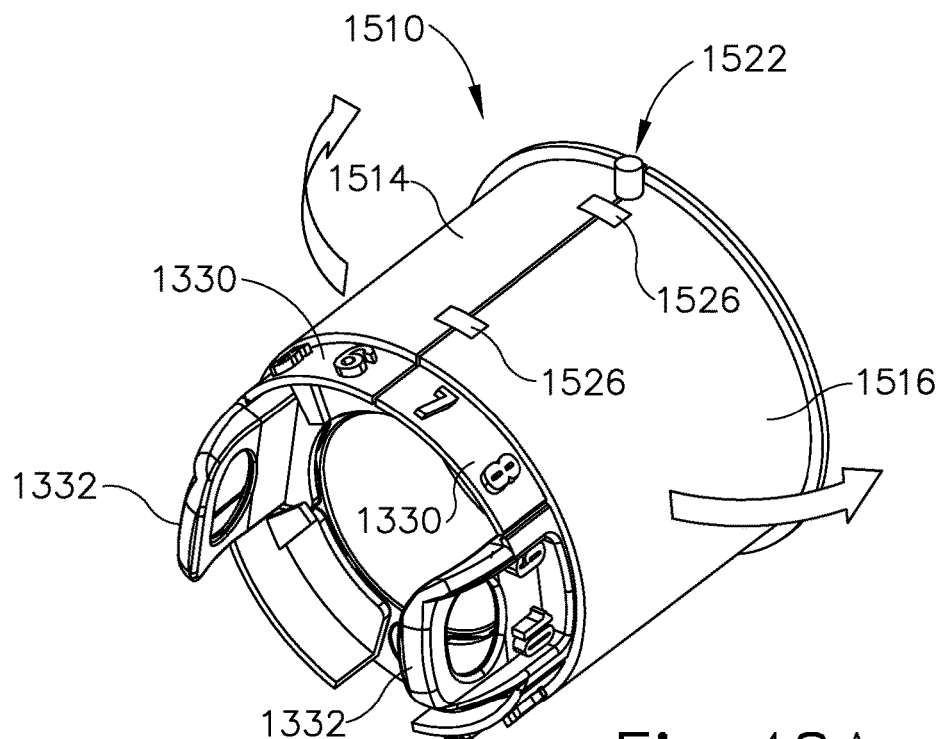
FIG. 48A depicts a perspective view of the another exemplary rotatable manifold in a folded position.
Figure 48B:
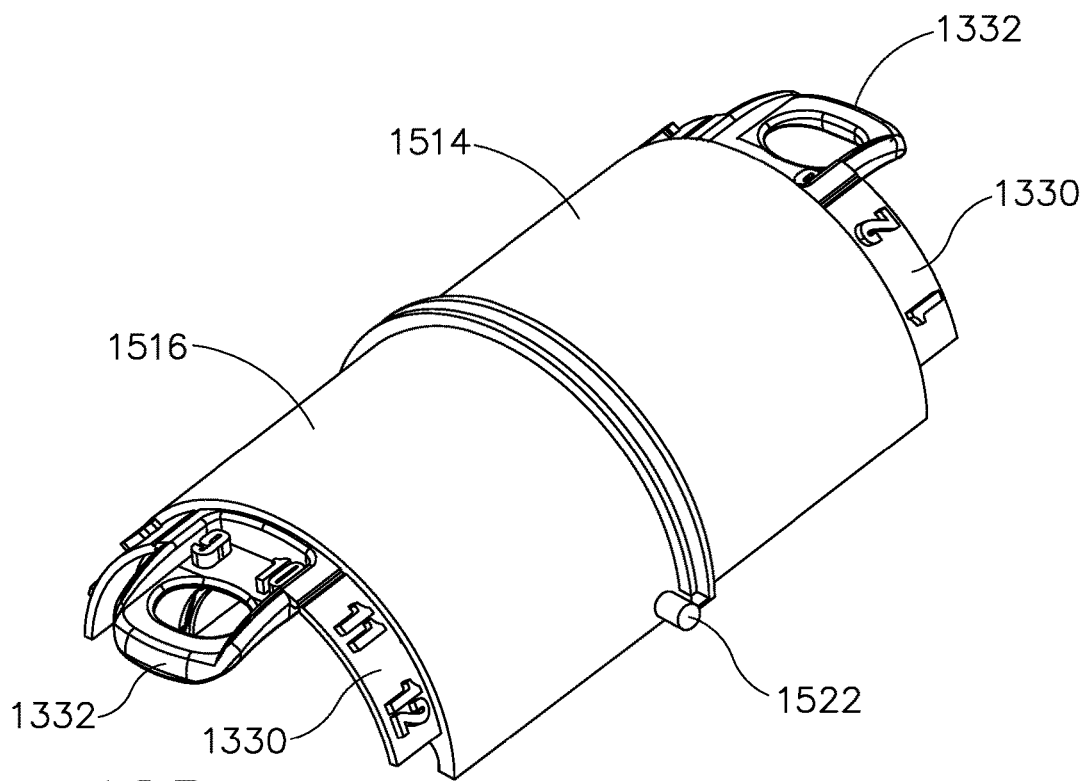
FIG. 48B depicts a perspective view of the manifold of FIG. 47A in an unfolded position.

FIGS. 48A-48B show another exemplary folding manifold (1510) that is similar to manifold (1410), except that sections (1514, 1516) of manifold (1510) are pivotable relative to each other via a pin (1522). Pin (1522) is positioned on a distal end of sections (1514, 1516). A pin (1522) may be provided on each opposing side of manifold (1510). Pin (1522) thereby allows sections (1514, 1516) to be pivoted such that sections (1514, 1516) are unfolded to position sections (1514, 1516) end to end. Accordingly, manifold (1510) is inserted within biopsy device (10) to collect tissue samples in the folded configuration shown in FIG. 48A. Once the samples are collected, manifold (1510) is removed from device (10). Tabs (1526) of first section (1514) are lifted to release second section (1516). Manifold (1510) is then unfolded to the flattened configuration shown in FIG. 48B and placed within slot (1014) of imaging system (1000) to image the tissue samples within manifold (1510).

Figure 49A:
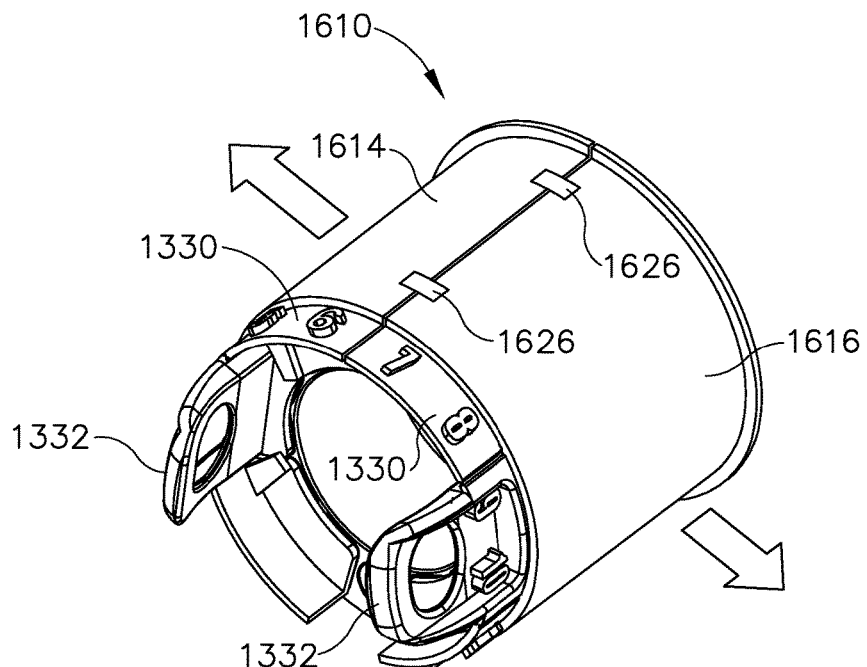
FIG. 49A depicts a perspective view of the another exemplary rotatable manifold in a folded position.
Figure 49B:
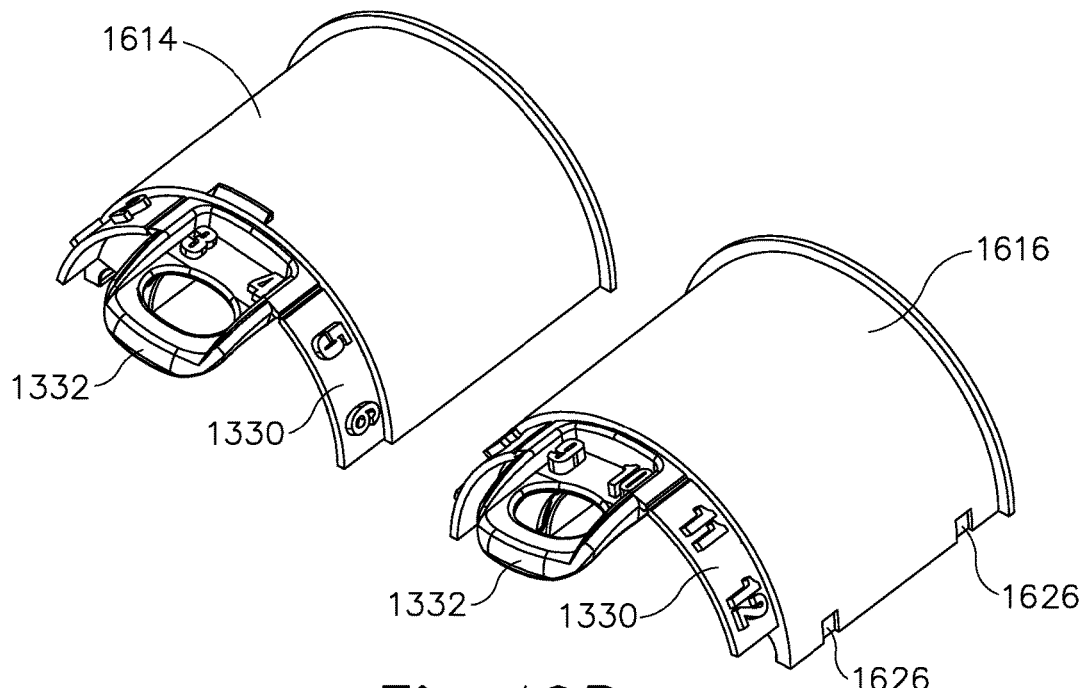
FIG. 49B depicts a perspective view of the manifold of FIG. 48A in an unfolded position.

In some versions, a manifold (1610) comprises sections (1614, 1616) that are removably coupled with each other. FIGS. 49A-49B show an exemplary manifold (1610), similar to manifold (1410), except that manifold (1610) comprises removable sections (1614, 1616) that separate instead of folding relative to each other. First and second sections (1614, 1616) are joined by a pair of locking tabs (1626) on each end of sections (1614, 1616). Although two tabs (1626) are shown in the present example, any other suitable number of tabs (1626) may be used. Accordingly, manifold (1610) is inserted within biopsy device (10) to collect tissue samples in the joined configuration shown in FIG. 49A. Once the samples are collected, manifold (1610) is removed from device (10). Tabs (1626) are lifted to release sections (1614, 1616). Sections (1614, 1616) of manifold (1610) are then decoupled to the configuration shown in FIG. 49B and placed within slot (1014) of imaging system (1000) to image the tissue samples within sections (1614, 1616) of manifold (1610). Sections (1614, 1616) may both be placed within slot (1014) of imaging system (1000) to be imaged together, or sections (1614, 1616) may be placed independently within slot (1014) to be imaged separately.

Figure 50A:
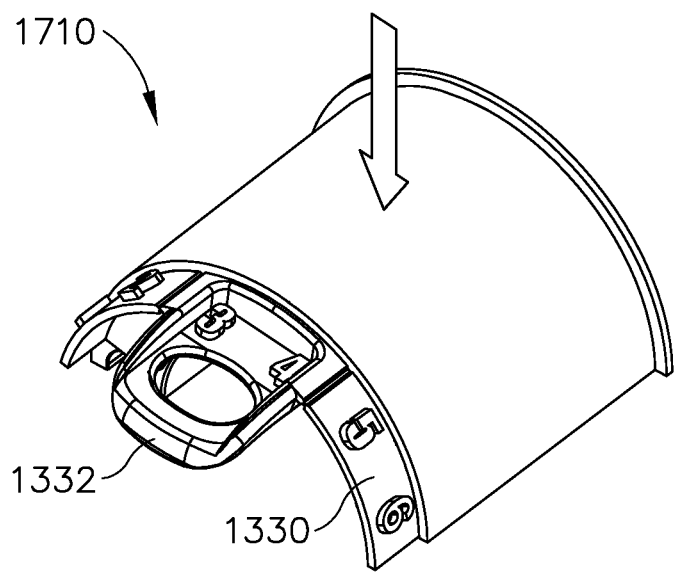
FIG. 50A depicts a perspective view of the another exemplary rotatable manifold in a folded position.
Figure 50B:
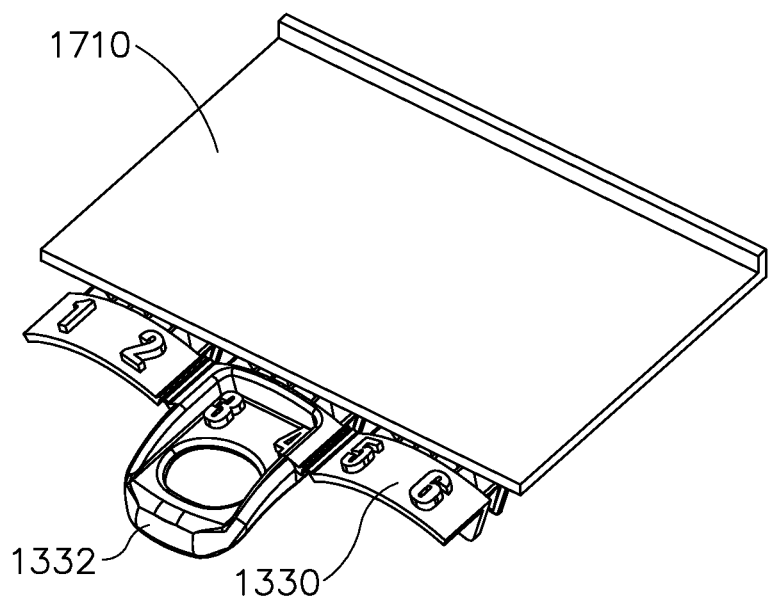
FIG. 50B depicts a perspective view of the manifold of FIG. 49A in an unfolded position.

FIGS. 50A-50B show another exemplary manifold section (1710) that is similar to a section (1614, 1616) of manifold (1610), except that manifold section (1710) has a flexible configuration or is otherwise deformable to a flattened state. FIG. 50A shows section (1710) in an arcuate configuration after section (1710) has been removed from device (10) with tissue samples collected in tray (1330) inserted within section (1710). The top portion of section (1710) is then pressed to flex section (1710) to the flattened configuration, as shown in FIG. 50B. As section (1710) flexes outwardly to the flattened configuration, section (1710) thereby pushes tray (1330) to a flattened configuration within section (1710). Section (1710) is then placed within slot (1014) of imaging system (1000) to be imaged.

Figure 51:
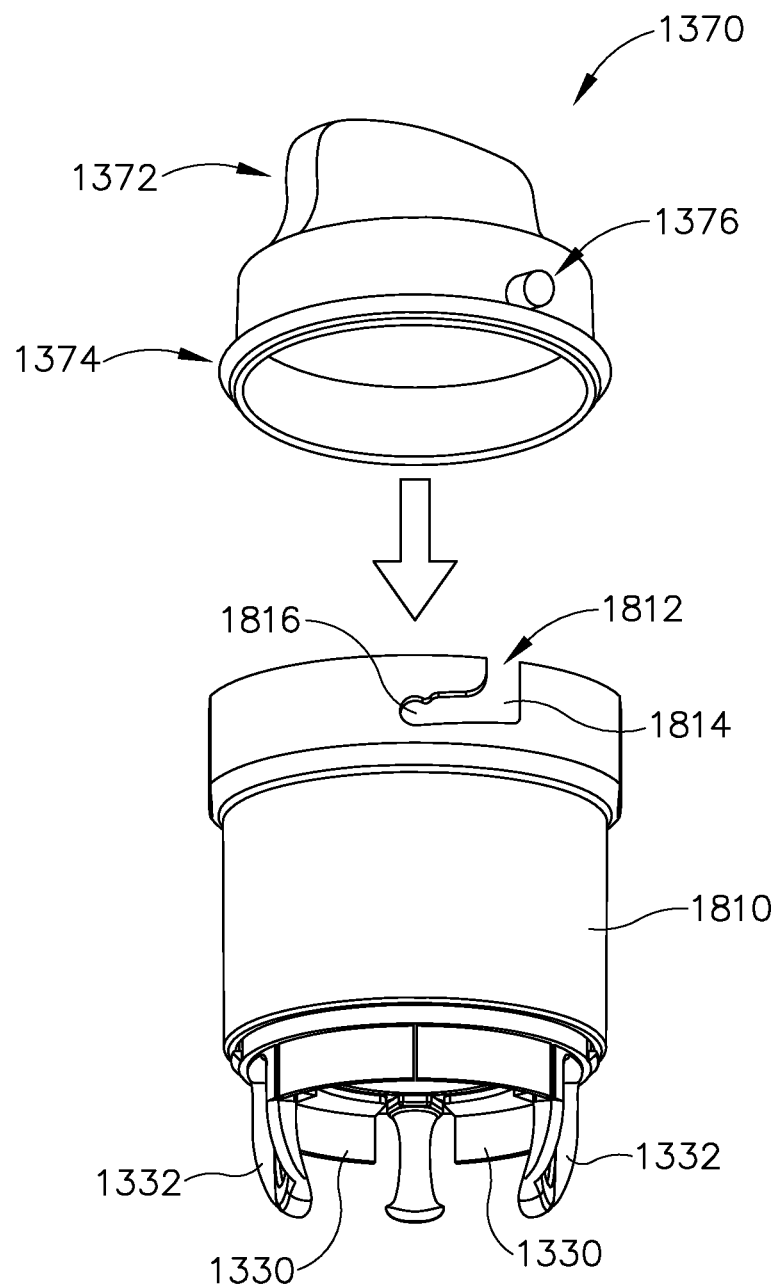
FIG. 51 depicts a perspective view of another exemplary rotatable manifold.

In some versions, a cap (1370) is placed over a distal end of a manifold (1810) when manifold (1810) is removed from biopsy device (10). FIG. 51 shows an exemplary cap (1370) with manifold (1810). Cap (1370) comprises a knob (1372) extending outwardly from cap (1370), a seal (1374) on the opposing end of cap (1370), and a protrusion (1376) extending outwardly from a side wall of cap (1370). Seal (1374) is positioned between cap (1370) and the distal end of manifold (1810) to provide a fluid tight seal between cap (1370) and manifold (1810) when cap (1370) is coupled with manifold (1810). Seal (1374) may be rubber, plastic, or other suitable material. Protrusion (1376) is configured to couple with manifold (1810) to secure cap (1370) with manifold (1810). Manifold (1810) is similar to manifold (310), except that manifold (1810) comprises a recess (1812) to receive protrusion (1376) of cap (1370). Recess (1812) includes a first portion (1814) extending within manifold (1810) and a second portion (1816) extending transversely to first portion (1814). Accordingly, cap (1370) may be positioned on manifold (1810) to align protrusion (1376) with first portion (1814) and pushed such that protrusion (1376) is inserted within first portion (1814). Knob (1372) may then be used to rotate cap (1370) relative to manifold (1810) such that protrusion (1376) enters second portion (1816) of recess (1812). This thereby secures cap (1370) with manifold (1810) with a bayonet style fitting. Manifold (1810) may then be placed within slot (1014) of imaging system (1000) with cap (1370) coupled with manifold (1810) to image the tissue samples within manifold (1810). In some instances, formalin or a similar fluid may be added to manifold (1810) before cap (1370) is secured to manifold (1810).

C. Exemplary Image Devices

As noted above, imaging system (1000) receives tissue samples to image through a slot (1014) of image control module (1010). Slot (1014) may be configured to receive a manifold (310, 1310, 1410, 1510, 1610, 1710, 1810), a tissue sample tray container (2100, 2200, 2300, 2400, 2500, 2600, 2700, 2800), or the tissue samples directly. Below are merely illustrative examples of image control modules (1010) with various slot (1014) configurations that may be incorporated with an imaging system (1000).

Figure 52:
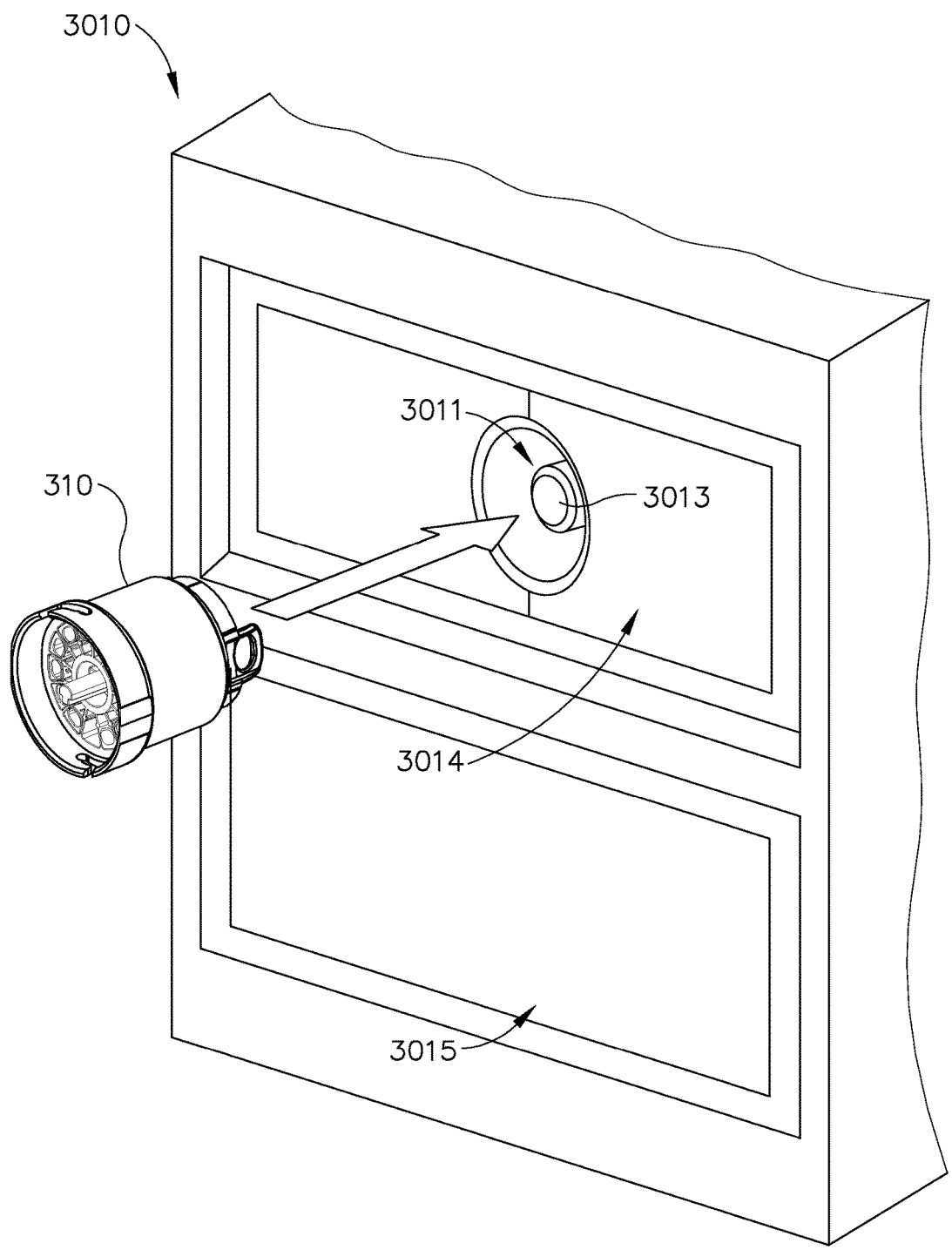
FIG. 52 depicts a perspective view of an exemplary imaging device of the imaging system of FIG. 31, receiving a manifold.

FIG. 52 shows an exemplary image control module (3010) with a slot (3014) configured to receive a tissue sample manifold (310). Slot (3014) comprises a recess (3011), a protrusion (3013), and a cover (3015). Recess (3011) is sized and configured to receive manifold (310) such that the proximal end of manifold (310) is inserted within recess (3011). Protrusion (3013) extends within recess (3011) and is configured to insert within an opening of manifold (310) to align manifold (310) within slot (3014). Recess (3011) may be configured to rotate manifold (310) within recess (3011) to align each tissue sample within manifold (310) with imaging device (1012) within control module (3010). Cover (3015) is configured to slide along control module (3010) such that cover (3015) selectively covers slot (3014). Slot (3014) may also be removably coupled with control module (3010) such that slot (3014) may be sterilized and/or replaced. A new slot (3014) may be inserted within control module (3010) to accommodate various sizes of manifolds (310).

In an exemplary use, cover (3015) of control module (3010) is slid relative to control module (3010) to uncover slot (3014). A manifold (310) containing tissue samples is inserted within recess (3011) of slot (3014), as shown in FIG. 52. In the present example, the proximal end of manifold (310) is inserted within recess (3011) to position protrusion (3013) within a central opening of manifold (310). The distal end of manifold (310) may optionally be covered by a cap (1370) when manifold (310) is inserted within slot (3014). A first tissue sample within manifold (310) is then imaged by imaging device (1012) within control module (3010). The image is processed by data processor (1016) and displayed on display (1018) to allow a user to analyze the first tissue sample. Slot (3014) may then rotate manifold (310) within slot (3014) to align a second tissue sample within manifold (310) with imaging device (1012). Imaging device (1012) may then image the second tissue sample within slot (3014) and control module (3010) may process the image through data processor (1016) and display the image on display (1018). Control module (3010) may repeat this process until all of the tissue samples contained within manifold (310) have been imaged. Manifold (310) may then be removed from slot (3014). Another manifold (310) may then be inserted within slot (3014) to image additional tissue samples, or slot (3014) may be decoupled from control module (3010) such that another slot (3014) may be inserted within control module (3010). After imaging is complete, cover (3015) may again be slid relative to control module (3010) in the opposing direction to cover slot (3014).

Figure 53:
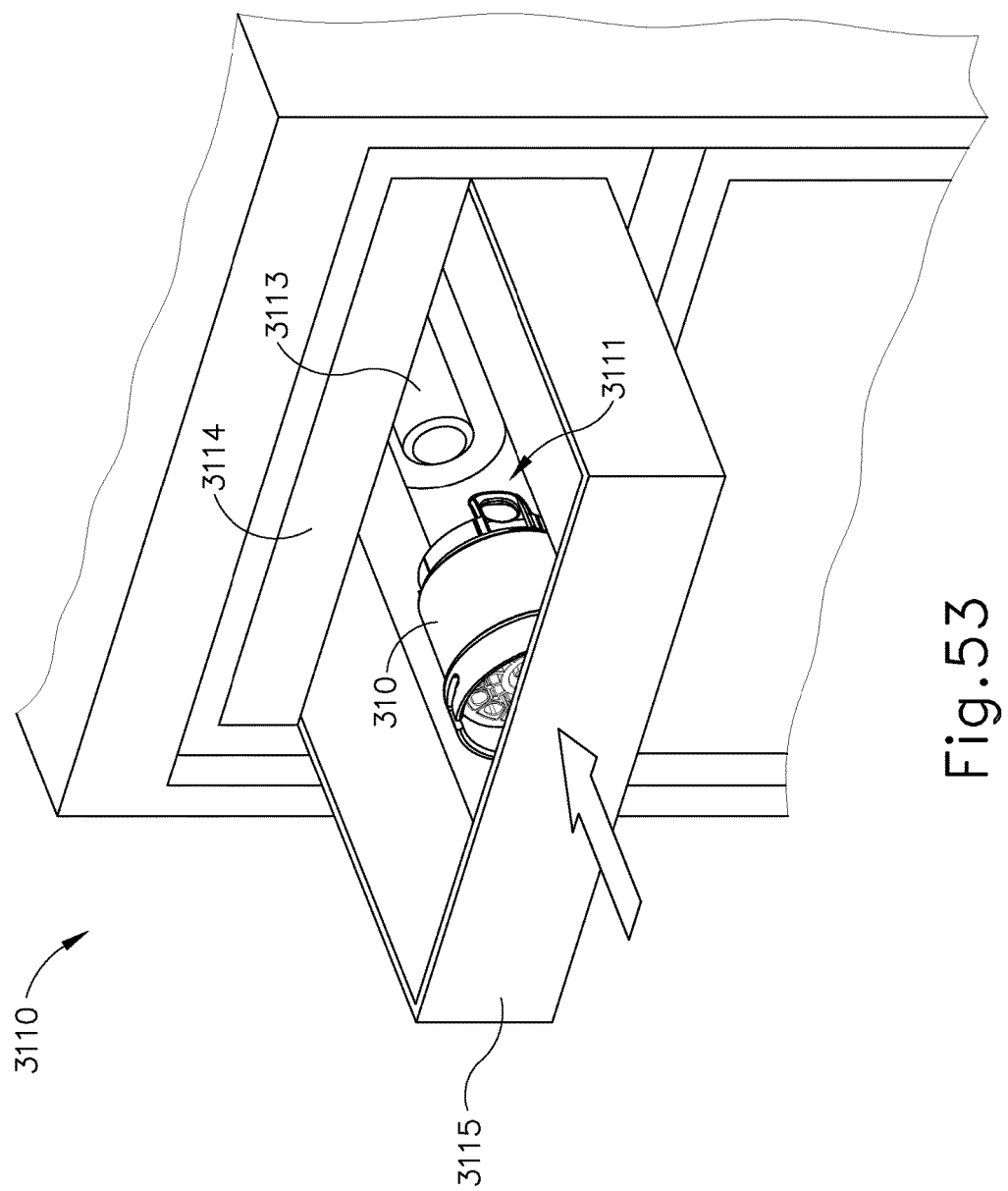
FIG. 53 depicts a perspective view of another exemplary imaging device of the imaging system of FIG. 31, receiving a manifold.

FIG. 53 shows another exemplary imaging control module (3110) that is similar to control module (3010), except that slot (3114) of control module (3110) comprises a drawer (3115). Drawer (3115) is configured to translate relative to control module (3110) such that drawer (3115) is selectively opened and/or closed. Drawer (3115) comprises a channel (3111) extending within drawer (3115) that is configured to receive a manifold (310). A protrusion (3113) extends within slot (3114) such that when drawer (3115) is closed, protrusion (3113) inserts within a central opening of manifold (310) to maintain the position of manifold (310) within slot (3114). Accordingly, drawer (3115) of control module (3110) is translated relative to control module (3110) to open drawer (3115). A manifold (310) containing tissue samples is inserted within channel (3111) of drawer (3115), as shown in FIG. 53. Drawer (3115) is then translated within slot (3114) of control module (3110) to close drawer (3115). As drawer (3115) closes, manifold (310) is positioned on protrusion (3113). A first tissue sample within manifold (310) is then imaged by imaging device (1012) within control module (3110). The image is processed by data processor (1016) and displayed on display (1018) to allow a user to analyze the first tissue sample. Manifold (310) may then be rotated, such as by rotating protrusion (3113), to align a second tissue sample within manifold (310) with imaging device (1012). Imaging device (1012) may then image the second tissue sample within slot (3114) and control module (3110) may process the image through data processor (1016) and display the image on display (1018). Control module (3110) may repeat this process until all of the tissue samples contained within manifold (310) have been imaged. Drawer (3115) may then be opened to remove manifold (310) from slot (3114). Another manifold (310) may then be inserted within drawer (3115) to image additional tissue samples, or drawer (3115) may be decoupled from control module (3110) such that another drawer (3115) may be inserted within control module (3110).

Figure 54:
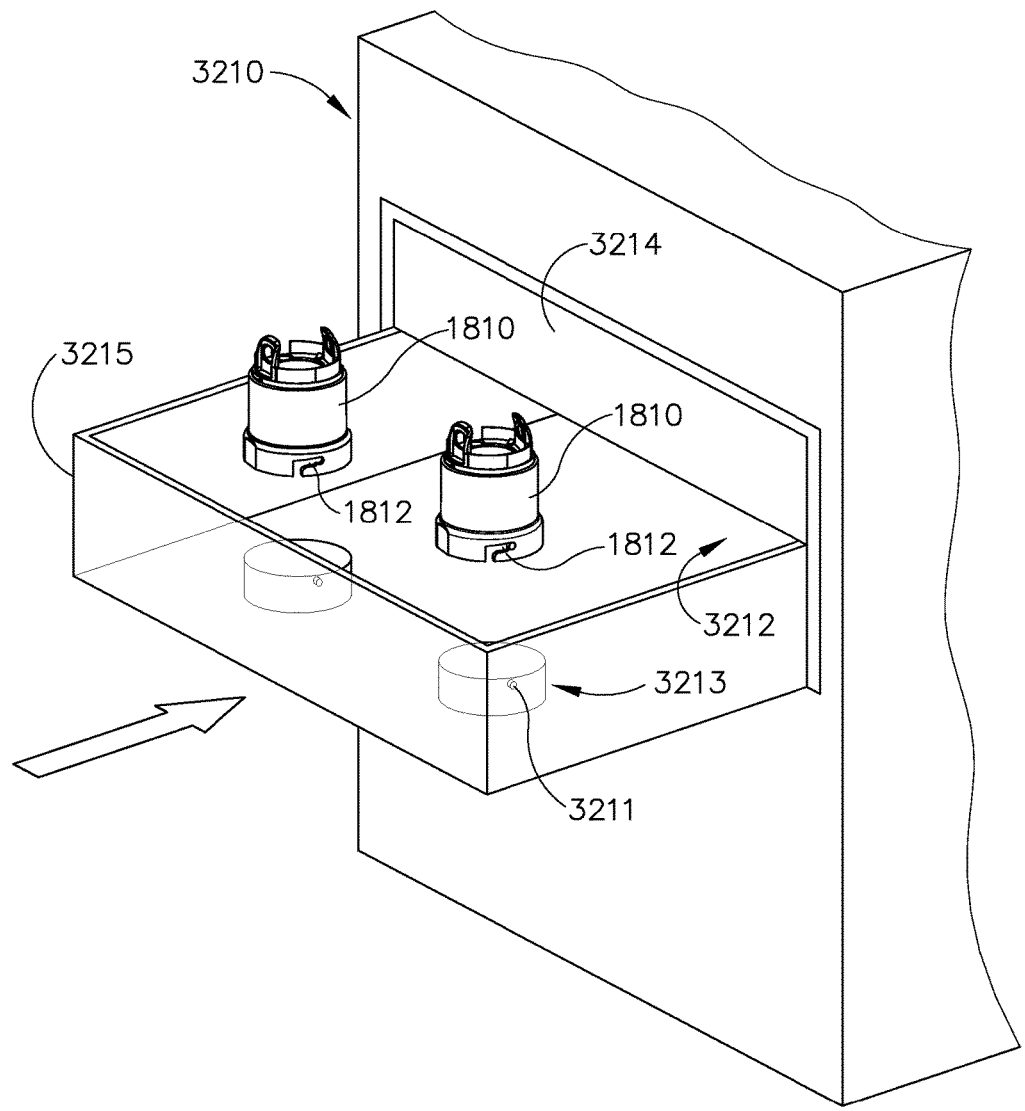
FIG. 54 depicts a perspective view of another exemplary imaging device of the imaging system of FIG. 31, receiving a manifold.

In some versions, a manifold (1810) is positioned transversely within a drawer (3215) of an imaging control module (3210). FIG. 54 shows another exemplary imaging control module (3210) that is similar to control module (3110), except that drawer (3215) of control module (3210) comprises protrusions (3213) extending upwardly within drawer (3215) to receive manifolds (1810) transversely within drawer (3215). In the present example, two protrusions (3213) are shown such that drawer (3215) is configured to receive two manifolds (1810). However, any other number of protrusions (3213) may be used to receive any number of manifolds (1810) within drawer (3215). Protrusions (3213) of drawer (3215) include tabs (3211) extending outwardly from protrusions (3213). Tabs (3211) are inserted within recesses (1812) of manifolds (1810) to lock manifolds (1810) relative to protrusions (3213). As described above, imaging control module (3210) may utilize x-ray imaging to image the tissue samples contained within manifold (1810). Because manifolds (1810) are positioned transversely within drawer (3215), the x-ray source of imaging device (3212) may be positioned at an end of drawer (3215). Likewise, the x-ray imaging sensor may be positioned at an opposing end of drawer (3215). Of course, in other examples, the x-ray source and x-ray imaging sensor may be positioned on opposing sides of drawer (3215), above and below drawer (3215), or in any other configuration as will be apparent to those of ordinary skill in the art in view of the teachings herein.

Accordingly, drawer (3215) of control module (3210) is translated relative to control module (3210) to open drawer (3215). A plurality of manifolds (1810) containing tissue samples are positioned on protrusions (3213) of drawer (3215), as shown in FIG. 54. Manifolds (1810) are then rotated such that tabs (3211) of protrusions (3213) insert within recesses (1812) of manifolds (1810) in a bayonet fitting to secure manifolds (1810) relative to protrusions (3213). Drawer (3215) is then translated within slot (3214) of control module (3210) to close drawer (3215). A first tissue sample within manifold (1810) is then imaged by imaging device (3212) within control module (3210). The image is processed by data processor (1016) and displayed on display (1018) to allow a user to analyze the first tissue sample. Slot (3214) may then rotate manifolds (1810) within slot (3214) to align a second tissue sample within manifold (1810) with imaging device (3212). Imaging device (3212) may then image the second tissue sample within slot (3214) and control module (3210) may process the image through data processor (1016) and display the image on display (1018). Control module (3210) may repeat this process until all of the tissue samples contained within manifolds (1810) have been imaged. Drawer (3215) may then be opened to remove manifolds (1810) from slot (3214). Additional manifolds (1810) may then be inserted within drawer (3215) to image additional tissue samples, or drawer (3215) may be decoupled from control module (3210) such that another drawer (3215) may be inserted within control module (3210).

Figure 55:
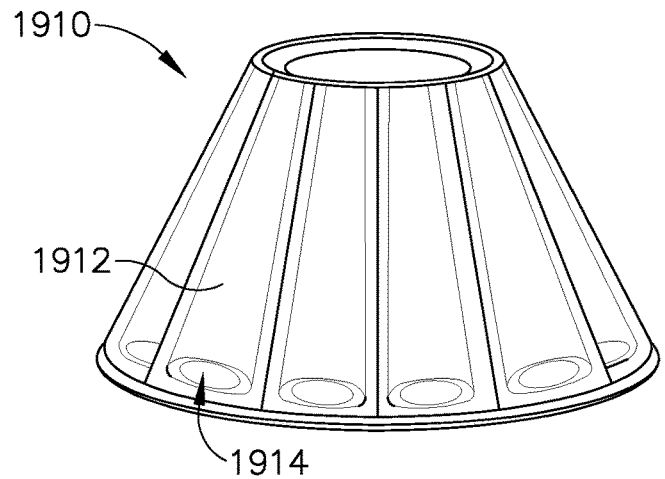
FIG. 55 depicts a perspective view of an exemplary conical tissue sample holder.
Figure 56:
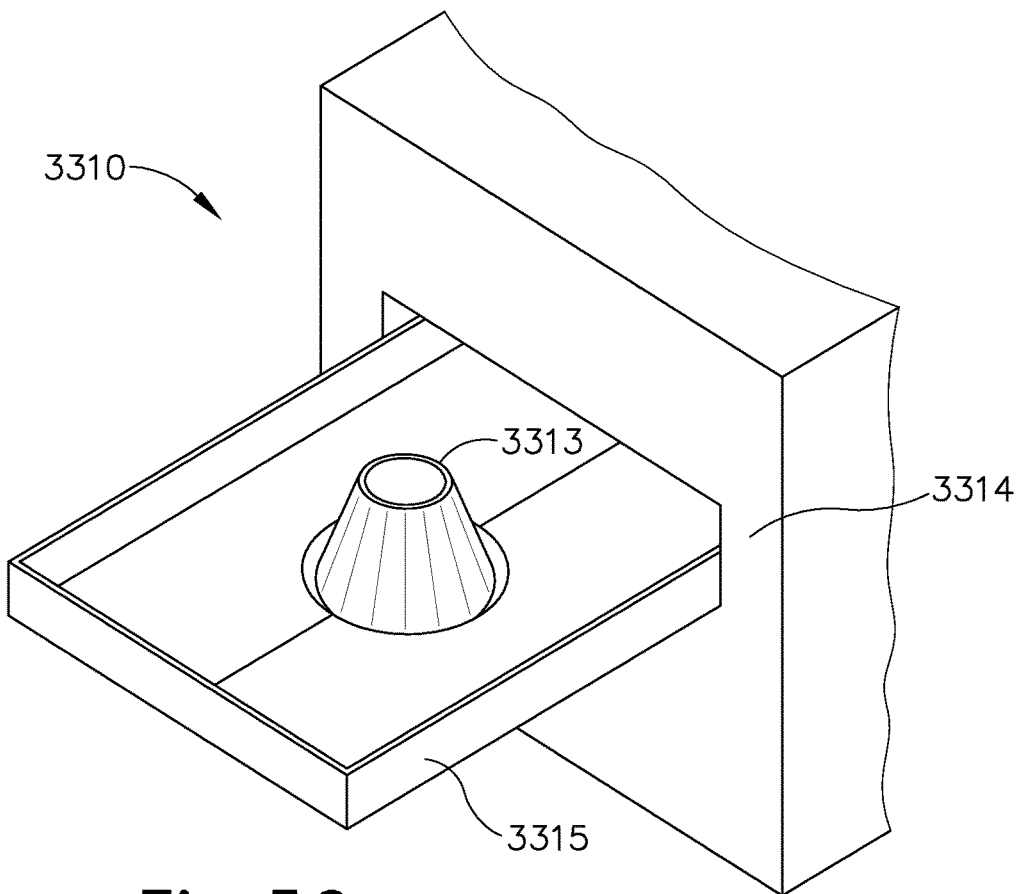
FIG. 56 depicts a perspective view of another exemplary imaging device of the imaging system of FIG. 31 for use with the tissue sample holder of FIG. 54.

FIG. 56 shows another exemplary imaging control module (3310) that is similar to control module (3210), except that control module (3310) comprises a drawer (3315) having a conical protrusion (3313). Protrusion (3313) is configured to receive a conical shaped tissue sample holder (1910), as shown in FIG. 55. Tissue sample holder (1910) comprises a plurality of chambers (1912) that are configured to receive tissue samples through openings (1914) of chambers (1912). Chambers (1912) are longitudinally aligned within tissue sample holder (1910). Accordingly, tissue samples collected by device (10) may be removed from device (10) and placed within tissue sample holder (1910), or manifold (310) of device (10) may be modified to have a conical shape to receive protrusion (3313) of drawer (3315). The conical shape of tissue sample holder (1910) allows control module (3310) to image the tissue samples within tissue sample holder (1910) from a top view.

Accordingly, drawer (3315) of control module (3310) is translated relative to control module (3310) to open drawer (3315). Tissue sample holder (1910) containing tissue samples is positioned on protrusion (3313) of drawer (3315) such that tissue sample holder (1910) extends outwardly along protrusion (3313). Drawer (3315) is then translated within slot (3314) of control module (3310) to close drawer (3315). A first tissue sample within tissue sample holder (1910) is then imaged by imaging device (1012) within control module (3310). The image is processed by data processor (1016) and displayed on display (1018) to allow a user to analyze the first tissue sample. Slot (3314) may then rotate tissue sample holder (1910) within slot (3314) to align a second tissue sample within tissue sample holder (1910) with imaging device (3312). Imaging device (1012) may then image the second tissue sample within slot (3314) and control module (3310) may process the image through data processor (1016) and display the image on display (1018). Control module (3310) may repeat this process until all of the tissue samples contained within tissue sample holder (1910) have been imaged. Drawer (3315) may then be opened to remove tissue sample holder (1910) from slot (3314). Additional tissue sample holders (1910) may then be inserted within drawer (3315) to image additional tissue samples, or drawer (3315) may be decoupled from control module (3310) such that another drawer (3315) may be inserted within control module (3310).

Figure 57:
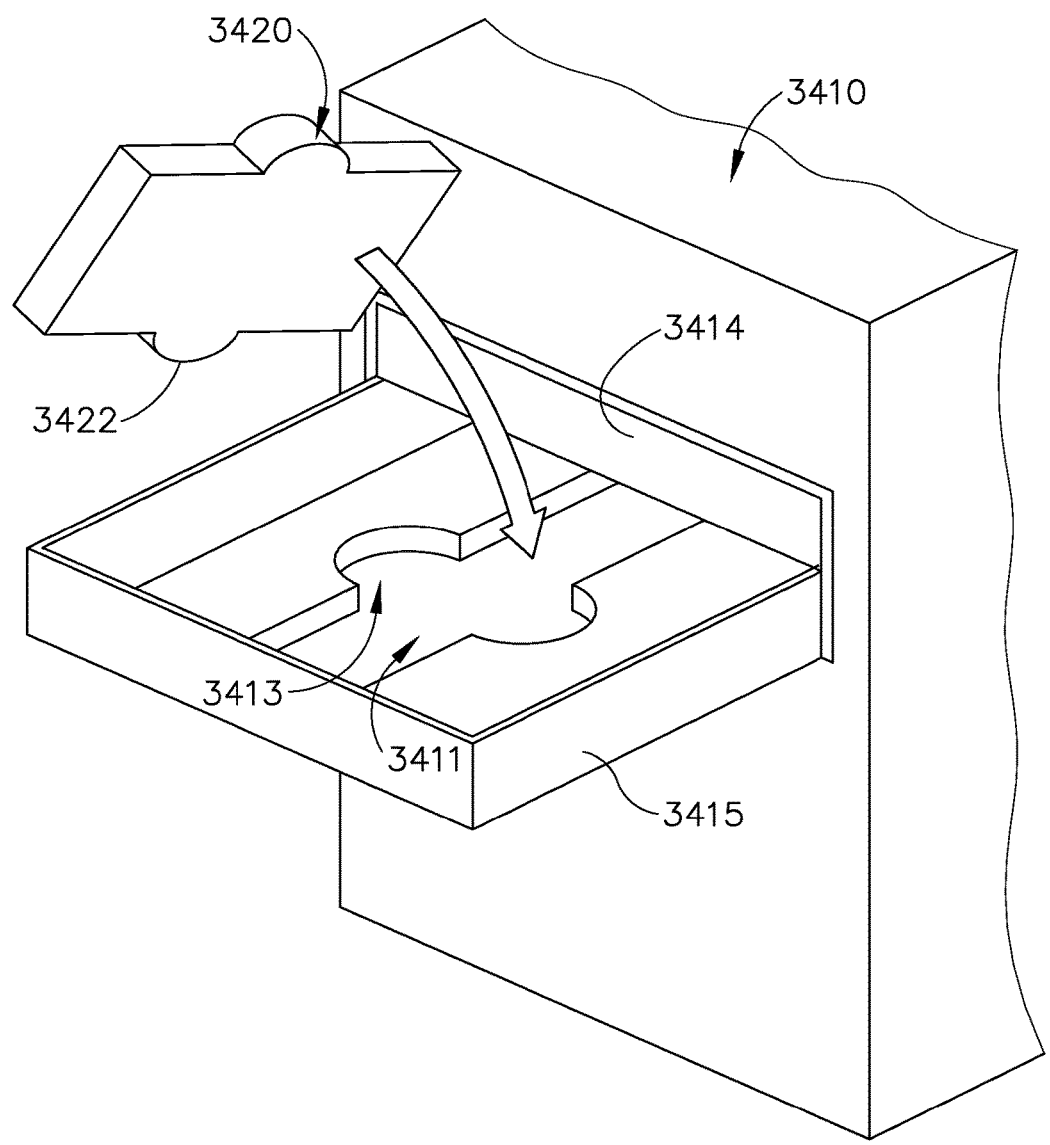
FIG. 57 depicts a perspective view of another exemplary imaging device of the imaging system of FIG. 31.

In some versions, imaging control module (3410) is configured to receive a tissue sample tray container (3420) instead of a manifold (310). FIG. 57 shows an exemplary control module (3410) that is configured to receive a tissue sample tray container (3420). Control module (3410) is similar to control module (3110), except that drawer (3415) of control module (3410) defines a recess (3411) to receive tissue sample tray container (3420). In the present example, recess (3411) defines channels (3413) extending from recess (3411). Channels (3413) are configured to receive extensions (3422) extending outwardly from container (3420) to maintain the longitudinal position of container (3420) within recess (3411). Alternatively, recess (3411) may be shaped to correspond to a container (3420) inserted within recess (3411). In an exemplary use, drawer (3415) of control module (3410) is translated relative to control module (3410) to open drawer (3415). Container (3420) is positioned within recess (3411) of drawer (3415) such that openings (3413) of recess (3411) receive extensions (3422) of container (3420). Drawer (3415) is then translated within slot (3414) of control module (3410) to close drawer (3415). A first tissue sample within container (3420) is then imaged by imaging device (1012) within control module (3410). The image is processed by data processor (1016) and displayed on display (1018) to allow a user to analyze the first tissue sample. Because container (3420) aligns the tissue samples laterally within slot (3414), imaging device (1012) may image all of the tissue samples simultaneously. Alternatively, slot (3414) may translate container (3420) within slot (3414) to align a second tissue sample with imaging device (3312). Imaging device (1012) may then image the second tissue sample within slot (3414) and control module (3410) may process the image through data processor (1016) and display the image on display (1018). Control module (3410) may repeat this process until all of the tissue samples contained within container (3420) have been imaged. Drawer (3415) may then be opened to remove container (3420) from slot (3414). Additional containers (3420) may then be inserted within drawer (3415) to image additional tissue samples, or drawer (3415) may be decoupled from control module (3410) such that another drawer (3415) may be inserted within control module (3410).

Figure 58:
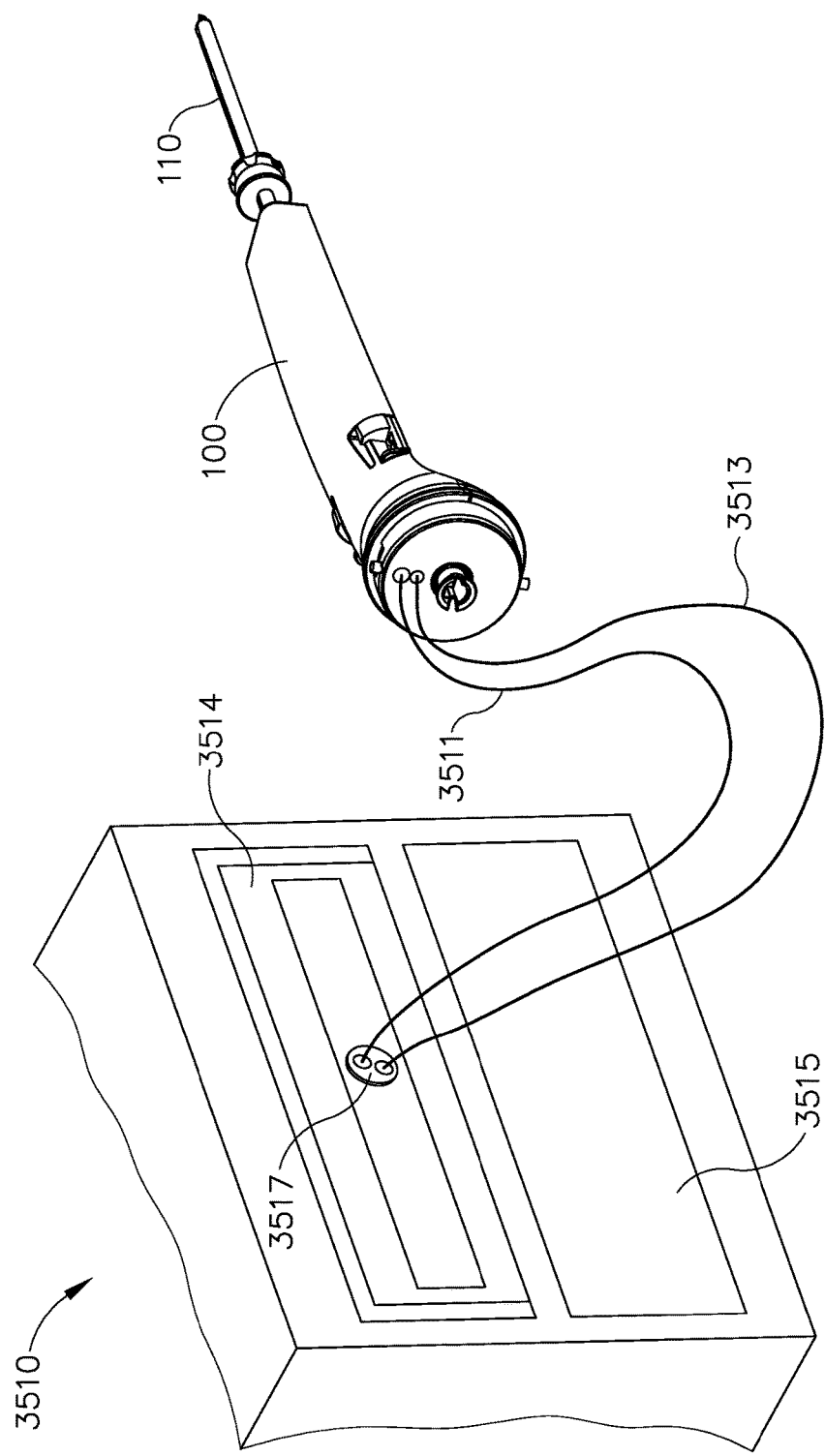
FIG. 58 depicts a perspective view of another exemplary imaging device of the imaging system of FIG. 31, coupled with a biopsy device.
Figure 59:
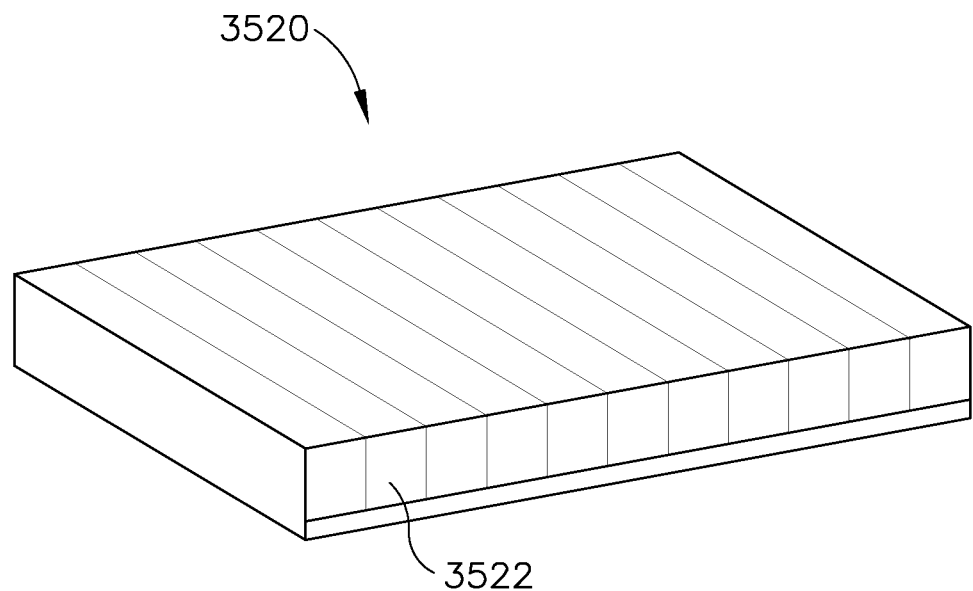
FIG. 59 depicts a perspective view of a tissue sample holder of the imaging device of FIG. 57.
Figure 60:
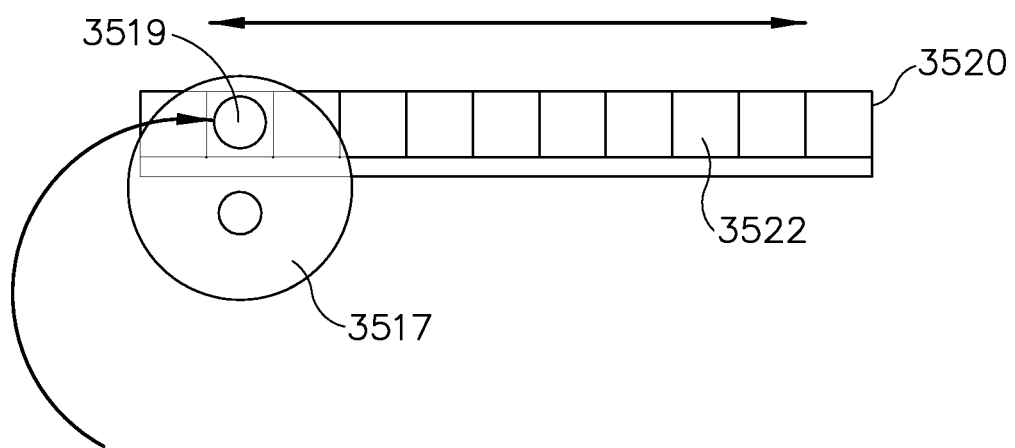
FIG. 60 depicts a front view of the tissue sample holder of FIG. 58.

In some versions, tissue samples may be directly deposited within an imaging control module (3510). FIG. 58 shows an exemplary control module (3510) that is couplable with a probe (100) such that control module (3510) directly receives tissue samples collected by probe (100). Probe (100) is coupled with slot (3514) of control module (3510) via cables (3511, 3513). Control module (3510) is similar to control module (3010), except that control module (3510) comprises a tissue sample holder (3520) within slot (3514). As shown in FIGS. 59-60, tissue sample holder (3520) comprises a plurality of chambers (3522) such that probe (100) directly deposits a tissue sample within a chamber (3522) of tissue sample holder (3520). Cable (3511) couples passageway (312) of manifold (310) with a chamber (3522) of tissue sample holder (3520) through an opening (3519) of plate (3517) within slot (3514), as shown in FIG. 60. A chamber (3522) is thereby aligned with passageway (312) of manifold (310). Once a chamber (3522) receives a tissue sample, control module (3510) laterally translates tissue sample holder (3520) within slot (3514) to index an adjacent chamber (3522) with opening (3519) of plate (3517) to receive the next tissue sample collected by probe (100). Control module (3510) is thereby operable to image each tissue sample when the tissue sample is collected by probe (100). Alternatively, control module (3510) may image the tissue samples after a plurality of tissue samples have been collected.

V. Exemplary Alternative Needle Assemblies

It may be desirable to enhance the visibility of needle assembly (110) under an imaging device (e.g. ultrasound, x-ray, etc.) during positioning of needle assembly (110) for collection of a tissue sample, to thereby facilitate positioning of needle assembly (110) in relation to a targeted tissue area for sampling. Accordingly, needle assembly (110) may include imaging features such that lateral aperture (114) is more readily visible relative to needle assembly (110) under an imaging device, such as an ultrasound imaging device, during a biopsy procedure. Below are merely illustrative examples of needle assemblies (110) that contain echogenic features to enhance visualization of lateral aperture (114).

Figure 61:
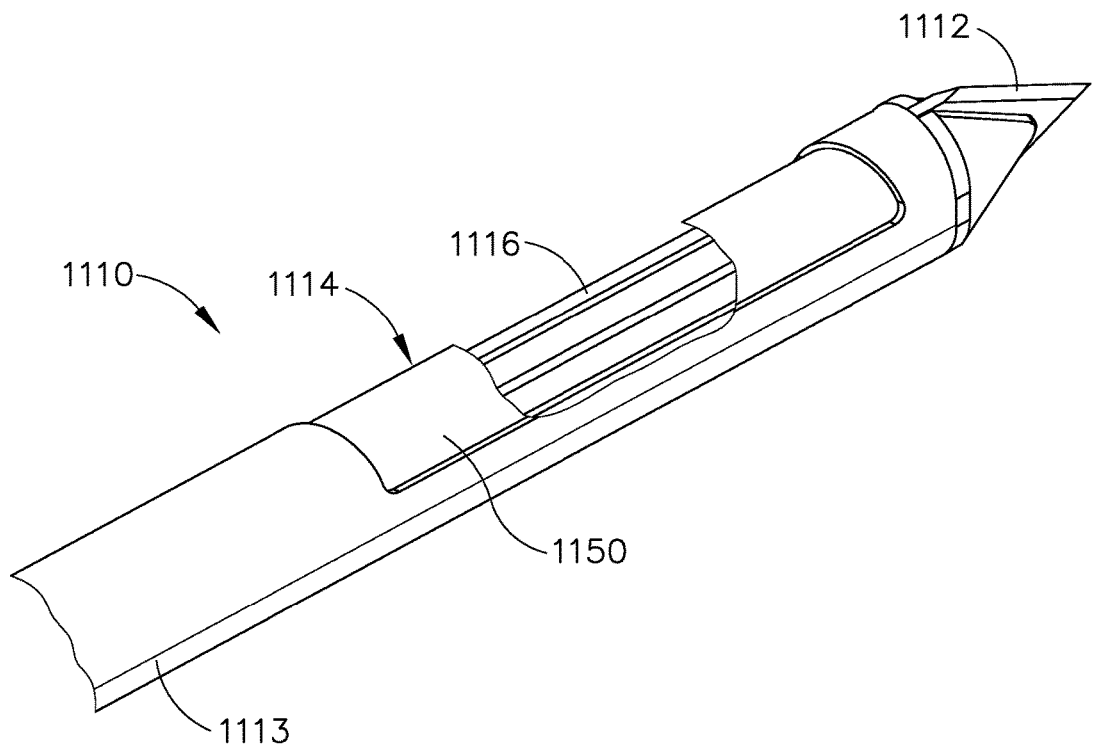
FIG. 61 depicts a perspective view of an exemplary needle assembly for use with the probe of FIG. 4, with a first insert.
Figure 62:
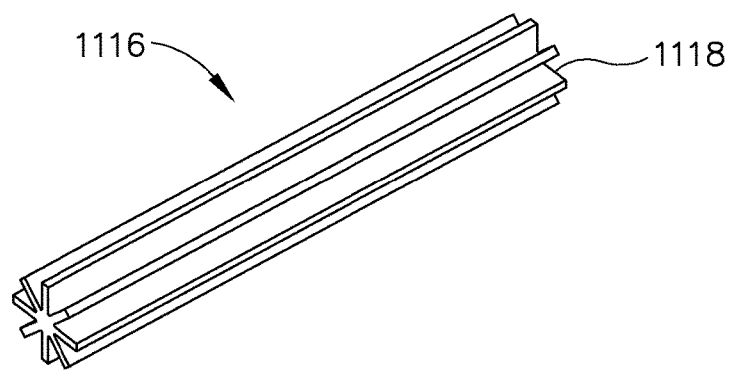
FIG. 62 depicts a perspective view of the first insert of FIG. 61.

FIGS. 61-62 show an exemplary needle assembly (1110) that is similar to needle assembly (110), comprising a tissue piercing tip (1112), a cannula (1113), a lateral aperture (1114), and a cutter (1150). Unlike needle assembly (110), needle assembly (1110) comprises an insert (1116). In particular, insert (1116) is inserted into cutter (1150). In FIG. 61, cutter (1150) is shown with a cut-away view so that insert (1116) is visible therein. Thus, cutter (1150) is in a position that is fully distal within needle assembly (1110). In this configuration, needle assembly (1110) may be inserted into a patient using tissue piercing tip (1112). Once inserted, cutter (1150) may be translated proximally within needle assembly (1110), exposing insert (1116). Insert (1116) may then be visualized by an imaging methodology such as ultrasound thus allowing a physician to approximate the location of the lateral aperture (1114) within the patent. Insert (1116) may be inserted into, and likewise retracted from, cutter (1150) by means of an elongate member (not shown) attached to a proximal end of insert (1116).

As shown in FIG. 62, insert (1116) comprises a plurality of splines extending outwardly from insert (1116) such that the shape of insert (1116) is readily identifiable under ultrasound. Insert (1116) may be made from metal and/or any other suitable material. Insert (1116) is positioned within needle assembly (1110) adjacent to lateral aperture (1114) such that the position of lateral aperture (1114) is visible under ultrasound imaging. In the present example, insert (1116) is substantially the length of lateral aperture (1114), but other lengths of insert (1116) may be used. Accordingly, needle assembly (1110) is inserted within tissue such that the position of lateral aperture (1114) is identifiable under ultrasound through insert (1116).

Figure 63:
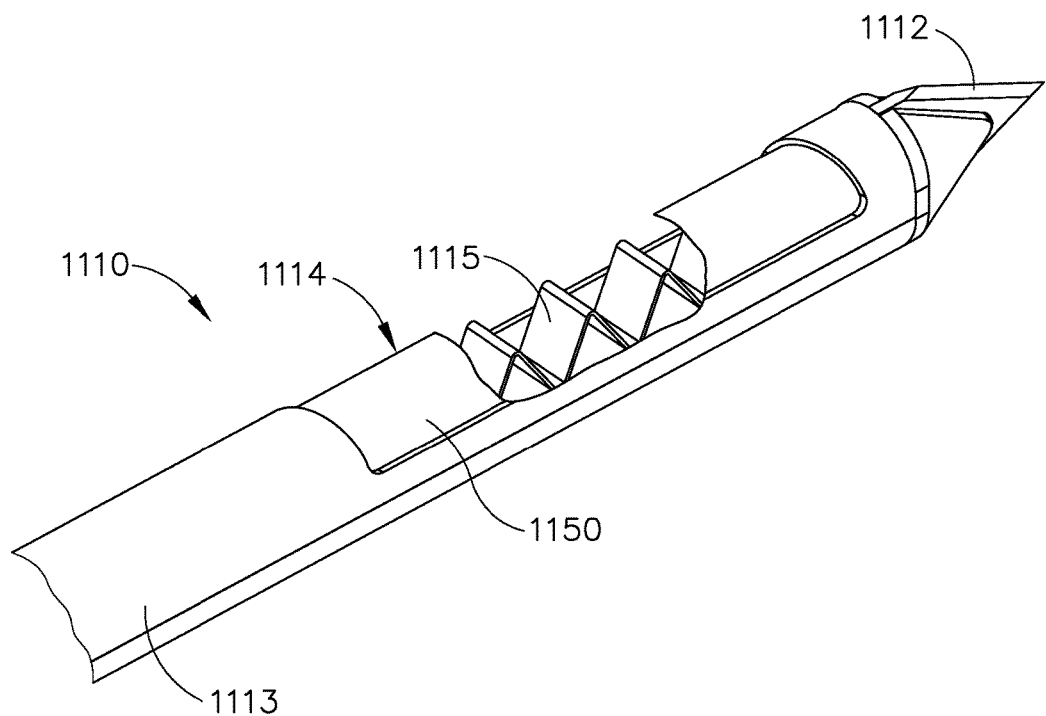
FIG. 63 depicts a perspective view of the needle assembly of FIG. 61, with a second insert.
Figure 64:
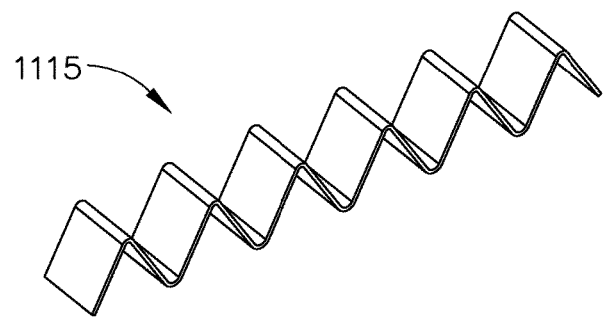
FIG. 64 depicts a perspective view of the second insert of FIG. 63.
Figure 65:
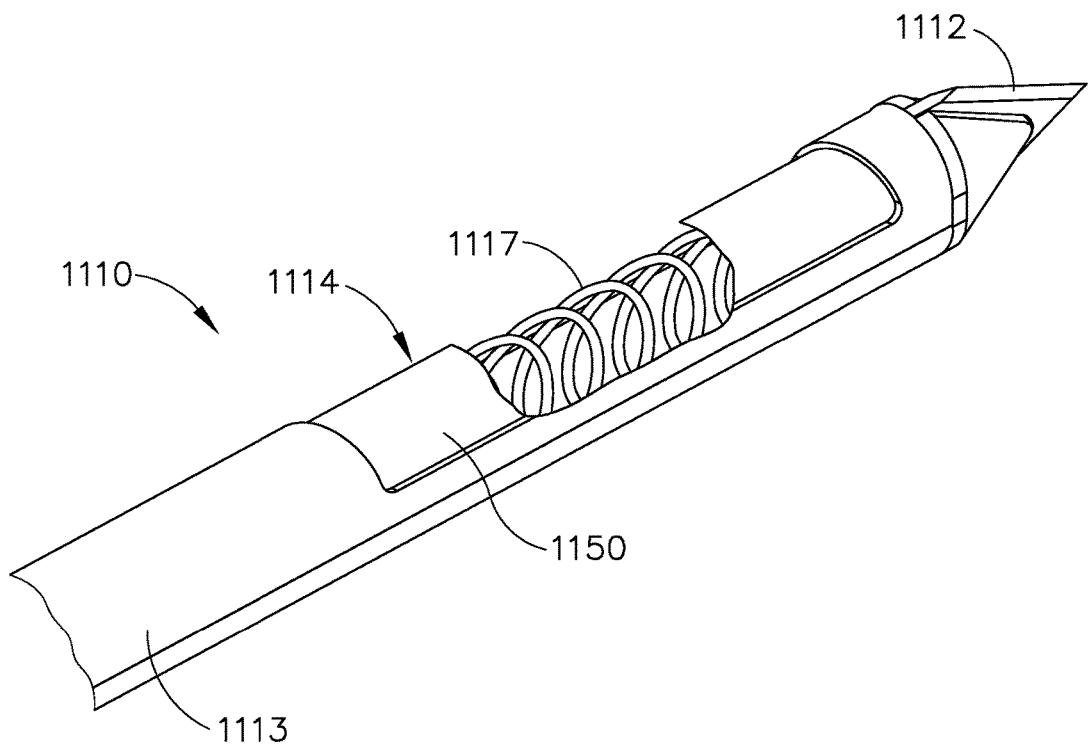
FIG. 65 depicts a perspective view of the needle assembly of FIG. 61, with a third insert.
Figure 66:
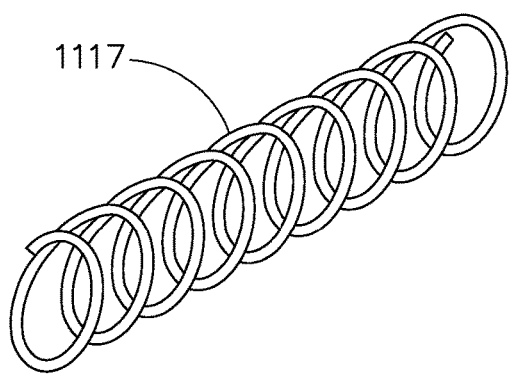
FIG. 66 depicts a perspective view of the third insert of FIG. 65.

Insert (1116) may also be provided with various configurations that are detectable by ultrasound. For instance, FIGS. 63-64 show another exemplary insert (1115) positioned within needle assembly (1110). Insert (1115) is similar to insert (1116), except that insert (1115) comprises a plurality of folds positioned adjacent to lateral aperture (1114). Like with insert (1116) insert (1115) may be attached to an elongate member (not shown) usable to translate insert (1115) relative to cutter (1150). FIGS. 65-66 show another exemplary insert (1117) positioned within needle assembly (1110) that is similar to insert (1115), except that insert (1117) has a coil configuration. Other suitable insert (1115, 1116, 1117) configurations will be apparent to one with ordinary skill in the art in view of the teachings herein.

Figure 67:
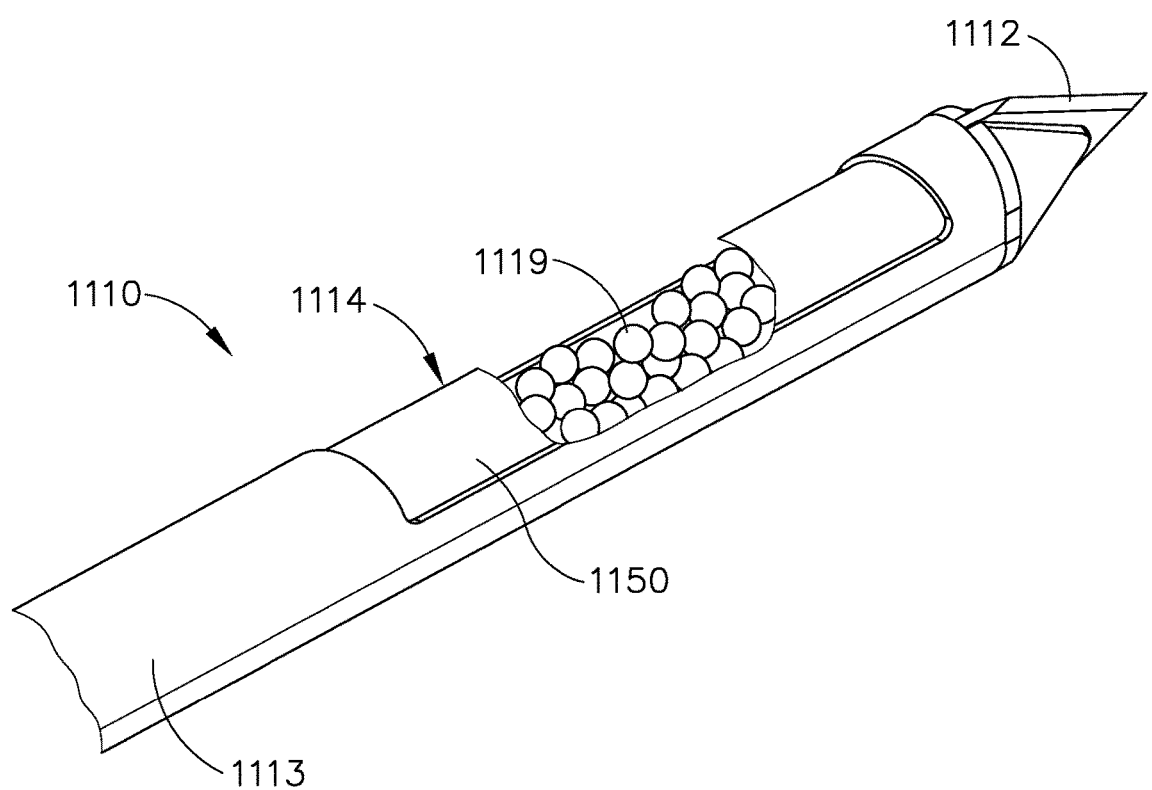
FIG. 67 depicts a perspective view of the needle assembly of FIG. 61, with a fourth insert.

Instead of an insert (1115, 1116, 1117), needle assembly (1110) may be filled with an echogenic material to visibly indicate the position of lateral aperture (1114) under ultrasound. For instance, FIG. 67 shows needle assembly (1110) filled with a plurality of beads (1119) positioned along the length of lateral aperture (1114). Beads (1119) may be made of metal and/or any other suitable material. Accordingly, beads (1119) are visible under ultrasound such that the position of lateral aperture (1114) is identifiable. Beads (1119) may be attached to one another by a flexible member (not shown) such as a string or cable. Such a flexible member may permit beads (1119) to be introduced or removed from cutter (1150) by an elongate member (not shown) as described above.

Figure 68:
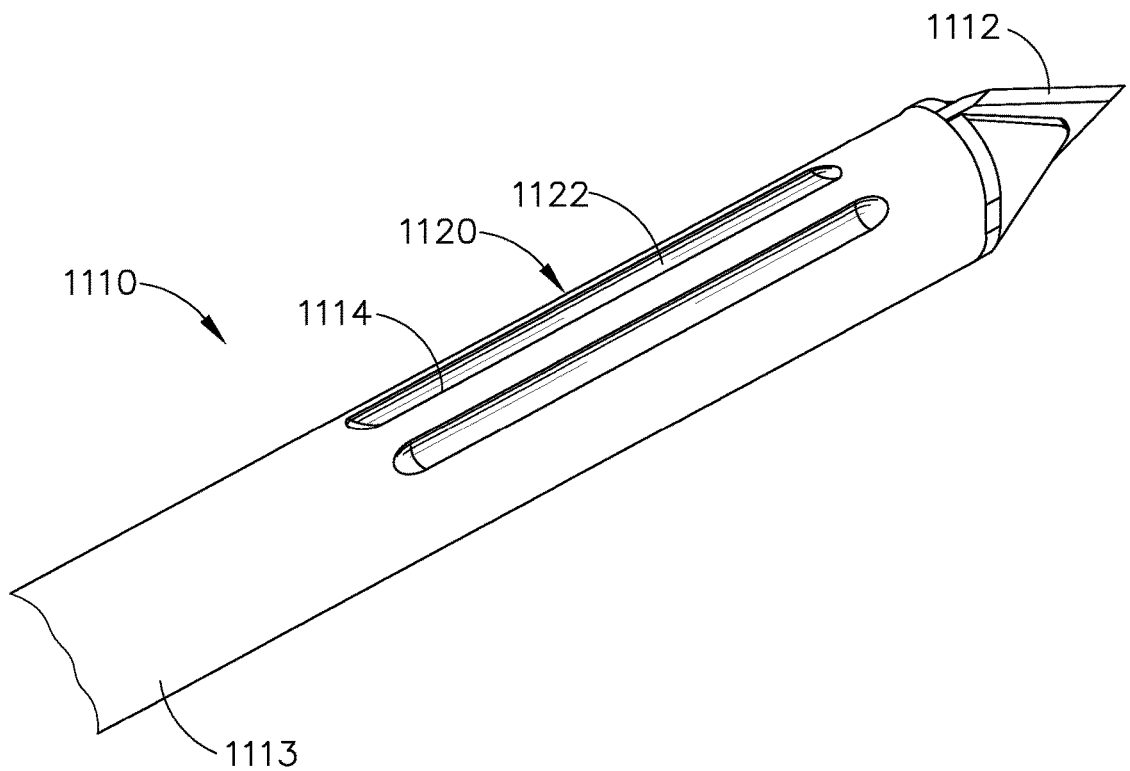
FIG. 68 depicts a perspective view of the needle assembly of FIG. 61, with a fifth insert.
Figure 69:
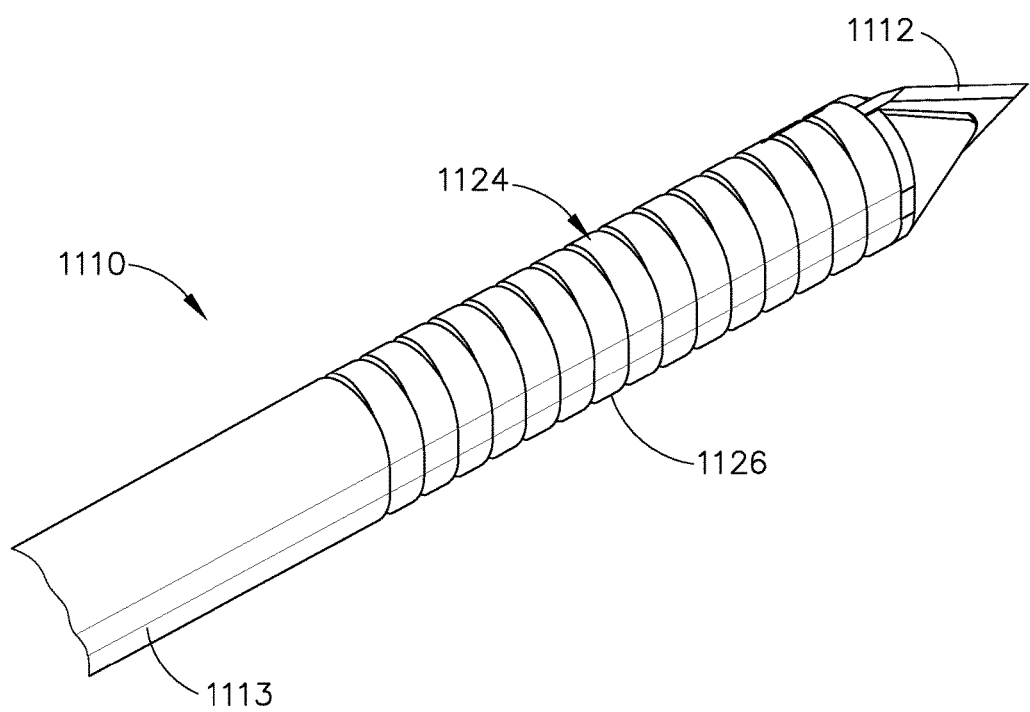
FIG. 69 depicts a perspective view of the needle assembly of FIG. 61, with a sixth insert.

Alternatively, an end portion of needle assembly (1110) may comprise a plurality of grooves to indicate the position of lateral aperture (1114). FIG. 68 shows an exemplary end portion (1120) of needle assembly (1110) with a plurality of grooves (1122) extending longitudinally along end portion (1120). In this example, grooves (1122) are on a side of needle assembly (1110) opposite from lateral aperture (1114). Thus lateral aperture (1114) is not visible in FIG. 68 as it is oriented on the other side of needle assembly (1110). FIG. 69 shows another exemplary end portion (1124) of needle assembly (1110) with a plurality of grooves (1126) extending transversely across end portion (1124) on a side opposite of lateral aperture (1114). Grooves (1122, 1126) extend along the same longitudinal region as lateral aperture (1114), such that grooves (1122, 1126) distally terminate and proximally terminate at positions corresponding to the distal and proximal boundaries of lateral aperture (1114). Grooves (1122, 1126) are thereby operable to visually indicate the position of lateral aperture (1114) of needle assembly (1110) under ultrasound.

VI. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, the biopsy device comprising at least one tissue sample holder, wherein the tissue sample holder comprises:
   (i) a plurality of strips, wherein the strips are configured to be axially received within one or more of a plurality of chambers defined by a portion of the biopsy device, wherein at least one strip is configured to receive a tissue sample, and
   (ii) a flexible member, wherein the flexible member joins at least one strip of the strips to another strip, wherein the strips are configured to pivot relative to the flexible member such that the strips are positioned flat or arcuate relative to one another; and
   wherein each strip of the plurality of strips comprises two sidewalls, a floor extending longitudinally, a back wall at a proximal end of the strip and a front wall at a distal end of the strip, wherein the sidewall, floor, back and front wall define a tissue sample chamber, wherein each sidewall comprises a wing, wherein the wing of each sidewall is configured to extend along the longitudinal length of each sidewall, wherein the wing extends laterally from the sidewall, wherein the wing of each sidewall is configured to seal against one or both of:
   (i) a sidewall of the chambers defined by the biopsy device, or
   (ii) a top portion of the chambers defined by the biopsy device, and
   wherein the sidewalls taper in height and the floor tapers in width such that the tissue sample chamber has an expanding cross sectional area as the sidewalls and floor extend longitudinally.

2. The biopsy device of claim 1, wherein the flexible member is a living hinge.

3. The biopsy device of claim 1 further comprising a tissue sample holder container, wherein the tissue sample holder container is configured to receive the plurality of strips in a flat configuration.

4. The biopsy device of claim 1, wherein the flexible member comprises at least one groove, wherein the strips are configured to pivot about the groove.

5. The biopsy device of claim 1, wherein the wings have a greater lateral extension on a distal end of the sidewall compared to a proximal end of the sidewall.

6. The biopsy device of claim 1, wherein each floor comprises at least one rib extending distally from a proximal end of the strips, wherein the rib is configured to stabilize the strip.

7. The biopsy device of claim 1, further comprising a tissue sample holder container, wherein the tissue sample holder container is configured to receive the plurality of strips in an arcuate configuration.

8. A biopsy device, the biopsy device comprising at least one tissue sample holder, wherein the tissue sample holder comprises:
   (a) a joining member, wherein the joining member comprises at least one flexible portion, wherein the at least one flexible portion permits the tissue sample holder to transition between an arcuate configuration and a flat configuration; and (b) a plurality of strips, wherein the strips are configured to be axially received within one or more of a plurality of chambers defined by a portion of the biopsy device, wherein at least one strip is configured to receive a tissue sample, wherein each strip of the plurality of strips comprises:
  (i) a pair of sidewalls,
  (ii) a floor,
  (iii) a back wall, wherein the back wall is secured to the joining member wherein each sidewall and the floor extends distally from the back wall, and
  (iv) a pair of wings, wherein each wing of the pair of wings is associated with a corresponding sidewall of the pair of sidewalls, wherein each wing of the pair of wings extends laterally and longitudinally relative to the corresponding sidewall of the pair of sidewalls, wherein the pair of wings are configured to sealingly engage a wall of a corresponding chambers of the plurality of chambers defined by the biopsy device, and wherein each wing of the pair of wings is tapered, and
  wherein the sidewalls taper in height and the floor tapers in width such that the tissue sample chamber has an expanding cross sectional area as the sidewalls and floor extend longitudinally.

9. The biopsy device of claim 8, wherein each strip of the plurality of strips further comprises an open distal end.

10. The biopsy device of claim 8, wherein the lateral extension of each wing of the pair of wings increases as each wing extends proximally relative to the corresponding sidewall.

11. The biopsy device of claim 10, wherein each side wall of the pair of sidewalls is tapered.

12. The biopsy device of claim 10, wherein the taper of each sidewall of the pair of sidewalls is defined by each sidewall being angled inwardly as each sidewall extends from the open distal end to the back wall.

13. The biopsy device of claim 12, wherein the taper of each sidewall of the pair of sidewalls corresponds to the taper of each wing such that the pair of wings define a consistent width between the open distal end and the back wall of each strip of the plurality of strips.

14. A biopsy device, the biopsy device comprising at least one tissue sample holder, wherein the tissue sample holder comprises:
(a) a joining member, wherein the joining member comprises at least one flexible portion, wherein the at least one flexible portion permits the tissue sample holder to transition between an arcuate configuration and a flat configuration; and
(b) a plurality of strips, wherein the strips are configured to be axially received within one or more of a plurality of chambers defined by a portion of the biopsy device, wherein at least one strip is configured to receive a tissue sample, wherein each strip of the plurality of strips comprises:
  (i) a pair of sidewalls, wherein each side wall of the pair of sidewalls includes a wing extending outwardly from each respective,
  (ii) a floor,
  (iii) a back wall, wherein the back wall is secured to the joining member wherein each sidewall and the floor extends distally from the back wall, and
  (iv) a front wall, wherein the front wall comprises a tissue receiving opening, wherein the pair of sidewalls and the floor extend from the back wall to the front wall to thereby defining a longitudinal length, wherein the wing of each sidewall of the pair of sidewalls extends along each respective sidewall for the longitudinal length defined by the pair of sidewalls and the floor, and
  wherein the sidewalls taper in height and the floor tapers in width such that the tissue sample chamber has an expanding cross sectional area as the sidewalls and floor extend longitudinally.

15. The biopsy device of claim 14, wherein the joining member comprises three segments, wherein each segment is joined by a corresponding flexible portion.

16. The biopsy device of claim 15, wherein each strip of the plurality of strips is associated with a corresponding segment of the joining member.

17. The biopsy device of claim 14, wherein the floor and the pair of sidewalls of each strip of the plurality of strips defines an interior and an exterior, wherein the wing of each sidewall of the pair of sidewalls is configured to seal the interior relative to the exterior.

* * * * *